United States Patent
Zhang et al.

(10) Patent No.: US 11,154,567 B2
(45) Date of Patent: Oct. 26, 2021

(54) METHOD FOR TREATING LIVER DISEASE WITH KINSENOSIDE

(71) Applicant: HUAZHONG UNIVERSITY OF SCIENCE AND TECHNOLOGY, Wuhan (CN)

(72) Inventors: Yonghui Zhang, Wuhan (CN); Ming Xiang, Wuhan (CN); Tingting Liu, Wuhan (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 0 days.

(21) Appl. No.: 16/779,686

(22) Filed: Feb. 3, 2020

(65) Prior Publication Data

US 2020/0171065 A1    Jun. 4, 2020

Related U.S. Application Data

(63) Continuation-in-part of application No. PCT/CN2018/097201, filed on Jul. 26, 2018.

(30) Foreign Application Priority Data

Aug. 2, 2017 (CN) .......................... 201710652728.6

(51) Int. Cl.
*A61K 31/7048* (2006.01)
*A61P 1/16* (2006.01)
*A61K 9/00* (2006.01)

(52) U.S. Cl.
CPC ........ *A61K 31/7048* (2013.01); *A61K 9/0053* (2013.01); *A61P 1/16* (2018.01)

(58) Field of Classification Search
None
See application file for complete search history.

(56) References Cited

U.S. PATENT DOCUMENTS

2008/0241283 A1* 10/2008 Lin .......................... A61P 35/00
424/725

OTHER PUBLICATIONS

CN102526481A, 2012, machine translation (Year: 2012).*
Mayo Clinic, Acute liver failure, internet article downloaded Dec. 1, 2020, https://www.mayoclinic.org/diseases-conditions/acute-liver-failure/symptoms-causes/syc-20352863. (Year: 2020).*
Xie, JP 2015080477, 2015, abstract and machine translation. (Year: 2015).*

* cited by examiner

*Primary Examiner* — Layla D Berry
(74) *Attorney, Agent, or Firm* — Matthias Scholl P.C.; Matthias Scholl

(57) ABSTRACT

A method for treatment of a liver disease, the method including administering kinsenoside to a patient in need thereof.

4 Claims, 70 Drawing Sheets

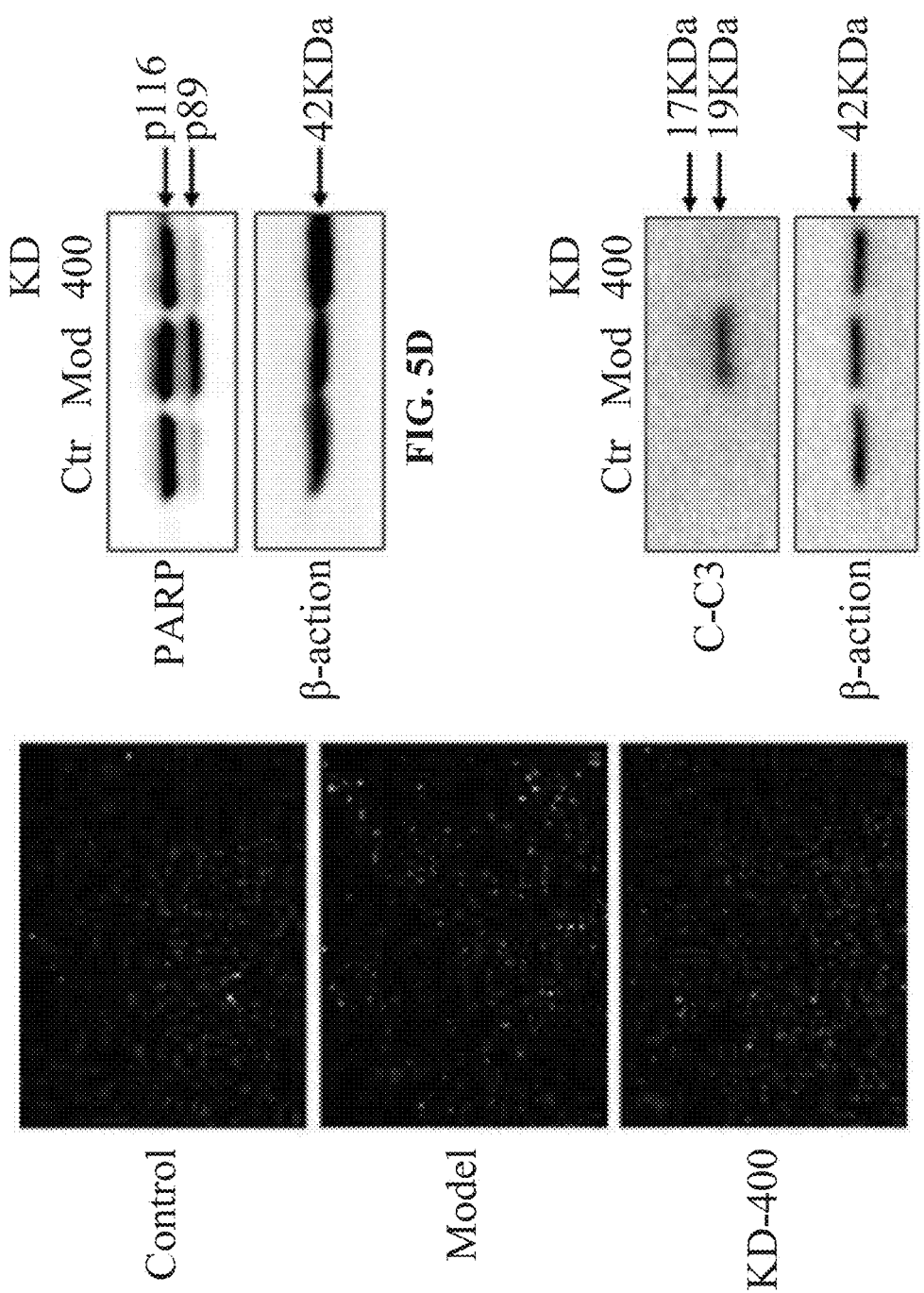

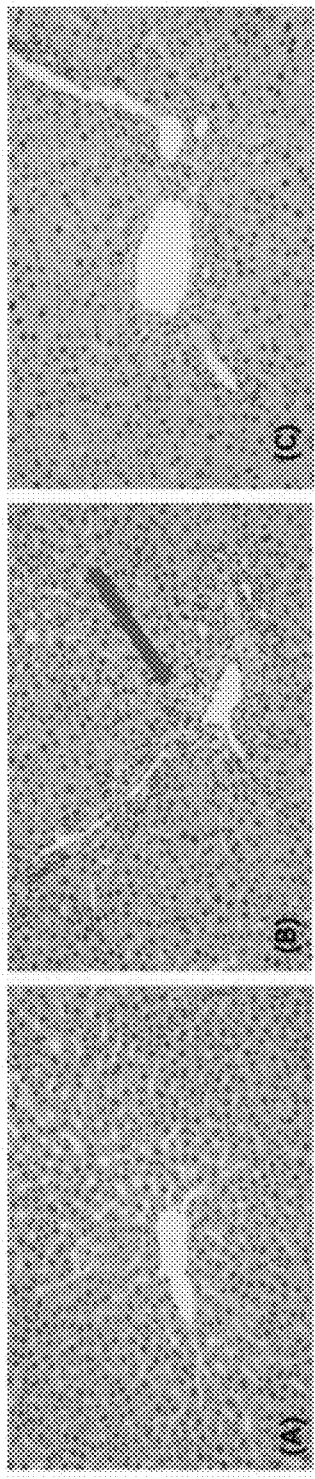
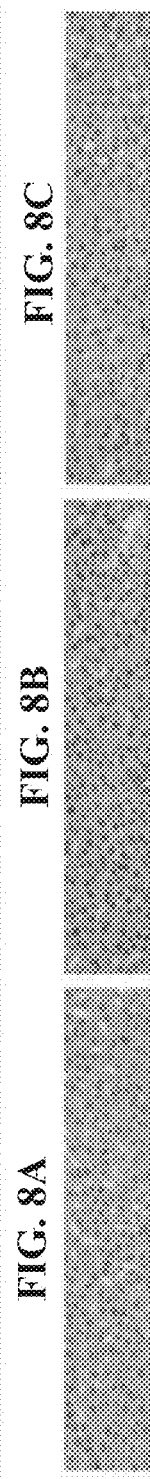
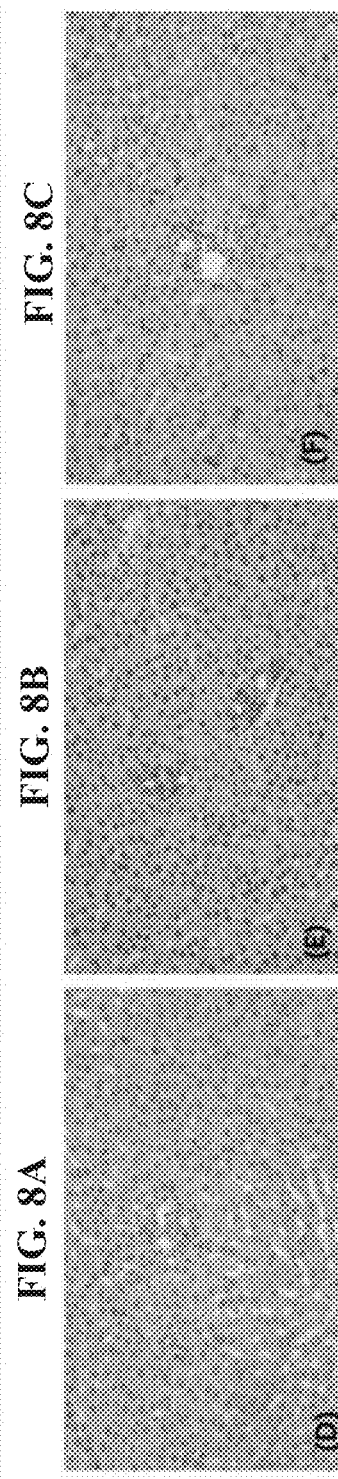
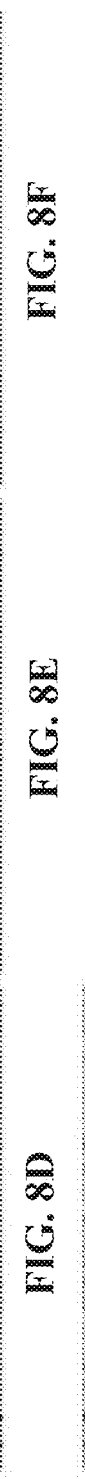
FIG. 8A  FIG. 8B  FIG. 8C  FIG. 8D  FIG. 8E  FIG. 8F  FIG. 8G

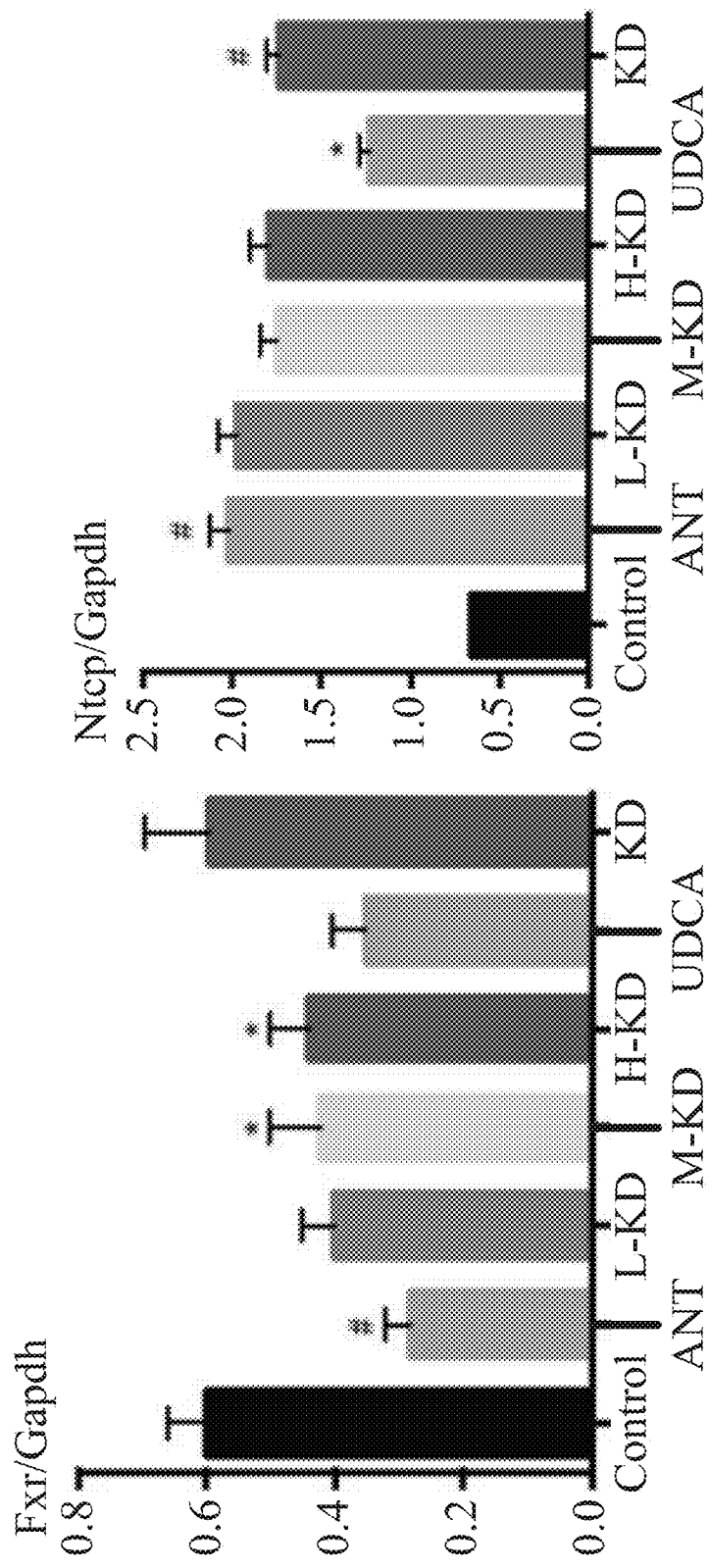

METHOD FOR TREATING LIVER DISEASE WITH KINSENOSIDE

CROSS-REFERENCE TO RELATED APPLICATIONS

This application is a continuation-in-part of International Patent Application No. PCT/CN2018/097201 with an international filing date of Jul. 26, 2018, designating the United States, now pending, and further claims priority benefits to Chinese Patent Application No. 201710652728.6 filed Aug. 2, 2017. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to the treatment of liver disease.

With the high incidence of liver disease and less choice of clinical medication, the demand for new drugs for liver disease is very urgent.

Kinsenoside (3-(R)-3-(3-D-glucopyranosyloxybutanolide) is a glycoside originally isolated from Anoectochilus.

SUMMARY

The disclosure provides a method for treatment of liver disease. Specifically, the method comprises administering kinsenoside to a patient in need thereof.

The following are examples of liver diseases: hepatic fibrosis, acute hepatic failure, cholestatic liver injury, alcoholic liver injury, and nonalcoholic fatty liver disease.

The kinsenoside has the following chemical formula and is purchased from Shanghai Tauto Biotech Co., Ltd., with a purity greater than 98.0%:

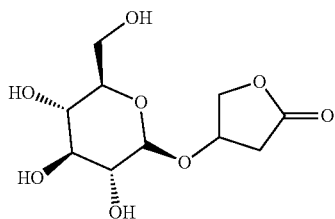

The kinsenoside is administered orally in the form of active pharmaceutical ingredients (APIs), and the follow-up preparations are oral preparations, including but not limited to tablets, capsules (including soft capsules), granules, powders, dry suspensions, etc.

From chronic to acute liver diseases, the dosage in mouse experiment is 10-400 mg/kg/d. According to the equivalent dose conversion, the predicted human dose is about 60 mg/d-3 g/d.

BRIEF DESCRIPTION OF THE DRAWINGS

FIG. 1A shows pathological damage of liver tissue; FIG. 1B shows ultrasonic detection of liver and spleen lesions; FIG. 1C shows expression of marker gene of liver fibrosis.

FIGS. 2A-2B show the indexes of liver function; FIGS. 2C-2D show the indexes of oxidative stress.

FIG. 4A shows the appearance of mouse liver; FIG. 4B shows the change of liver body ratio of mouse; FIG. 4C shows the H & E staining picture; FIGS. 4D-4E show the test of liver function with kit. FIGS. 4F-4G show oxidative stress injury. FIGS. 4H-4J show the inflammatory cytokines detected by flow cytometry kit.

FIGS. 5A-5E show the inhibitory effect of KD on hepatocyte apoptosis in liver failure measured by Western blot, transmission electron microscopy and Tunel fluorescence staining; FIG. 5A: Mitochondrial structure of mouse liver under transmission electron microscopy. FIG. 5B: Endoplasmic reticulum structure of mouse liver under transmission electron microscopy. FIG. 5C: The inhibition of hepatocyte apoptosis detected by Tunel fluorescence staining. FIGS. 5D-5E: Western blot analysis of apoptotic proteins. The results showed that apoptosis Marker protein PARP(Poly adp-ribose Polymerase) and C-C3 (Cleaved caspase-3) increased significantly after modeling, and KD could reduce abnormal apoptosis of hepatocytes and protect liver.

FIG. 6A: plasma color; FIG. 6B: body weight change; FIG. 6C: liver body ratio; FIG. 6D: bile flow rate FIG. 7A: changes of plasma alanine aminotransferase (ALT); FIG. 7B: Changes of plasma AST; FIG. 7C: Changes of plasma total bile acid (TBA); FIG. 7D: Changes of plasma alkaline phosphatase (AKP); FIG. 7E: changes of total bilirubin (TBIL) of plasma; FIG. 7F: Changes in direct bilirubin (DBIL) of plasma.

FIGS. 8A-8G are HE staining pathological sections of rat liver samples, which show the effect of KD on the pathophysiology of the liver of ANIT-induced cholestasis rats.

FIG. 9A: relative expression of Fxr mRNA; FIG. 9B: relative expression of Ntcp mRNA; FIG. 9C: relative expression of Bsep mRNA; FIG. 9D: relative expression of Mrp2 mRNA; FIG. 9E: relative expression of Mrp3 mRNA; FIG. 9F: relative expression of Mrp4 mRNA; FIG. 9G: relative expression of Cyp7a1 mRNA; FIG. 9H: relative expression of Cyp8b1 mRNA.

FIGS. 10A-10I show the effect of KD on the expression of Fxr, bile acid-related transporter and metabolic enzyme in ANIT-induced intrahepatic cholestasis rats; FIG. 10A: changes of Fxr and bile acid-related transporter and metabolic enzyme gene protein expression in rat liver; FIG. 10B: relative expression of Fxr protein; FIG. 10C: relative expression of Ntcp protein; FIG. 10D: relative expression of Bsep protein; FIG. 10E: relative expression of Mrp2 protein; FIG. 10F: relative expression of Mrp3 protein; FIG. 10G: relative expression of Mrp4 protein; FIG. 10H: relative expression of Cyp7a1 protein; FIG. 10I: relative expression of Cyp8b1 protein.

FIG. 11A: H&E staining of liver of alcoholic fatty liver (AFL) mice. The therapeutic effect of KD on alcoholic fatty liver was observed by H&E staining, and it was found that KD could reduce histopathological damage of liver and reduce fat vacuoles in liver of mice. FIG. 11B: H&E staining of liver of acute liver failure (ALF) mice. The results showed that the inflammatory cells in the KD group were reduced compared with the model group, the number of Mallory bodies was controlled, and KD could reduce ALF injury. FIG. 11C: Masson staining of liver of ALF experiment mouse. The results of Masson staining showed that for alcoholic liver fibrosis, KD treatment can significantly reduce the degree of fibrosis in mice. FIG. 11D: Biochemical kit was used to determine serum ALT of AFL and ALF mice. The results showed that KD decreased the serum alanine aminotransferase (ALT) of AFL and ALF mice and had a protective effect on liver. FIG. 11E: Biochemical kit was used to determine SOD in the liver of AFL and ALF mice. The results showed that KD increased the activity of superoxide dismutase (SOD) in the liver of AFL and ALF mice. FIGS. 11F-11G: Inflammatory cytokines in serum of AFL and ALF mice were determined by Elisa. KD inhibited the secretion of TNF and IL6 in AFL and ALF.

FIG. 12A: Liver appearance and H & E staining. In the control group (normal diet), model group (high fat and high fructose diet), low dose group (KD-L, high fat and high fructose diet+10 mg/kg KD), medium dose group (KD-M, high fat and high fructose diet+20 mg/kg KD), high dose group (KD-H, high fat and high fructose diet+30 mg/kg KD) and positive drug group (Sily, high fat and high fructose diet+silymarin 50 mg/kg), KD could significantly reduce liver lipid denaturation induced by high-fat and high-fructose diet and reduce the size and number of lipid droplets in liver; FIGS. 12B-12D: the liver function index were measured. The levels of ALT (B), AST (C), γ-GT (D) in the model group were significantly higher than those in the control group, and the therapeutic effect was better than that of silymarin; FIGS. 12E-12H: the levels of TC and TG in the liver and serum were detected by a kit; the level of total cholesterol in liver and serum of mice induced by high-fat and high-sugar diet was significantly increased, while the level of total cholesterol in liver and serum was significantly inhibited after the treatment with low, medium and high doses of KD; FIGS. 12I-12J: the level of low-density lipoprotein (LDLC) and free fatty acid (NAFE) in the serum was detected. Low dose of KD could significantly inhibit the level of serum LDL in mice, and each dose of KD could significantly inhibit the level of free fatty acids.

FIGS. 13A-13F: Flow cytometry kit was used to detect the secretion level of inflammatory cytokines in the serum of mice in each group. The results showed that the low, medium and high dose treatment of KD significantly inhibited the secretion of pro-inflammatory cytokines IL6, MCP-1, IFN-γ, TNF-α and IL-2 in the serum of mice, promoted the secretion of the anti-inflammatory cytokine IL-10; FIGS. 13G-13H: high dose KD inhibited the expression level of total macrophage marker molecule F4/80, medium and high dose KD significantly inhibited the expression level of inflammatory molecule COX-2, inhibited the expression of inflammatory M1-type macrophage molecules IL6 and IFN-γ, and promoted the expression of anti-inflammatory M2-type macrophage marker molecules CD206, ARG1 and IL1, respectively.

FIGS. 14A-14C: Simple fatty liver (NAFL) was formed after 2 weeks of modeling, and steatosis continued to worsen after 4 weeks. Fat accumulation in liver was significantly reduced in the high-dose KD group (40 mg/kg KD), the medium-dose group (20 mg/kg KD), and the low-dose group (10 mg/kg KD). The Image J software was used to analyze the lipid droplet area of the sections of each group at 8 w, and it was found that the fat accumulation in the liver could be significantly reduced in each dose of KD group, and the effect of the high-dose KD group was even better than that of the positive group. The liver index was the ratio of liver to body weight of mice. Compared with mice in the normal group, the liver index of the mice in the model group increased, indicating the accumulation of liver fat, while each KD group could reduce liver fat and normalize the liver index; FIGS. 14D-14E: after modeling, the serum aminotransferase level of the mice was significantly increased, and the AST and ALT levels were decreased in each dose group of KD, and the liver function was improved; FIGS. 14F-14I: the contents of fat TG and TC in serum and liver homogenate of mice were determined by biochemical kit. The results showed that the fat content in the liver of NASH mice induced by MCD was significantly decreased and the lipid content was slightly increased in all groups of KD.

FIG. 15A: HE staining results showed that nonalcoholic fatty liver (NAFL) was formed 2 weeks after modeling, inflammatory lesions began to develop at 4 weeks, and steatohepatitis (NASH) was formed at 6 weeks. The KD group could inhibit the inflammatory infiltration of liver. FIG. 15N: Immunohistochemical staining was used to investigate the expression of apoptosis marker protein Cleaved Caspase3 (CC3) in the liver. Compared with the normal group, CC3 expression increased in the model group, suggesting that the liver cell apoptosis in the model mice was severe. The KD group at different doses could reduce the liver cell apoptosis to varying degrees, thus reducing the expression of liver CC3 protein.

FIGS. 16A-16K: the results of Masson staining showed that the liver fibrosis of mice fed with MCD began to develop from Nash to liver fibrosis after 8 weeks, and the number of blue stained fibers in the liver of model group increased, and KD could reduce the generation of fibers in varying degrees; Image J software was used to analyze the fiber area of each section on the $8^{th}$ week. The results showed that the fiber area of the model group increased significantly. After KD treatment, the liver fiber content decreased, and the effect of KD was even better than that of the positive drug group; FIGS. 16C-16F: the index of "four items of liver fibrosis" in the serum was determined by ELISA. The results showed that the serum HA, LN, C -IV, PCIII of the model mice were significantly increased, and KD group could significantly reduce the content of HA and LN, which had a certain inhibitory effect on liver fibrosis; FIG. 16G: qPCR was used to detect the expression of fibrosis marker genes in liver tissues. The results showed that, KD could effectively inhibit the expression of α-smooth muscle actin (α-SMA), collagen I (Col I), tissue inhibitor of metalloproteinase-1 (TIMP-1) and transforming growth cytokine-β (TGF-β) in the liver of the mice, and increase the expression of matrix metalloproteinase-13 (MMP-13); FIG. 16H: the hardness of the mouse liver was measured by ultrasonic transient shear technique. The higher the shear rate, the harder the mouse's liver was; FIG. 16I: Image J software was used to quantify the hardness of livers in each group in H diagram. Compared with the normal group, the liver hardness of the model group increased, indicating severe fibrosis hyperplasia, while the liver hardness of the KD group decreased, indicating that KD could inhibit the progression of liver fibrosis in NASH mice; FIGS. 16J-16K: Western blot and immunohistochemistry were used to detect the expression of the marker protein α-SMA of hepatic fibrosis. The results showed that KD could reduce the expression of α-SMA and inhibit liver fibrosis.

DETAILED DESCRIPTION OF THE EMBODIMENTS

To further illustrate, embodiments detailing a method for treatment of hepatic disease are described below. It should be noted that the following embodiments are intended to describe and not to limit the disclosure.

EXAMPLE 1

Treatment of Hepatic Fibrosis using Kinsenoside

The kinsenoside (KD) was purchased from Shanghai Tauto Biotech Co., Ltd., with a purity greater than 98.0%.

Figure 1A:
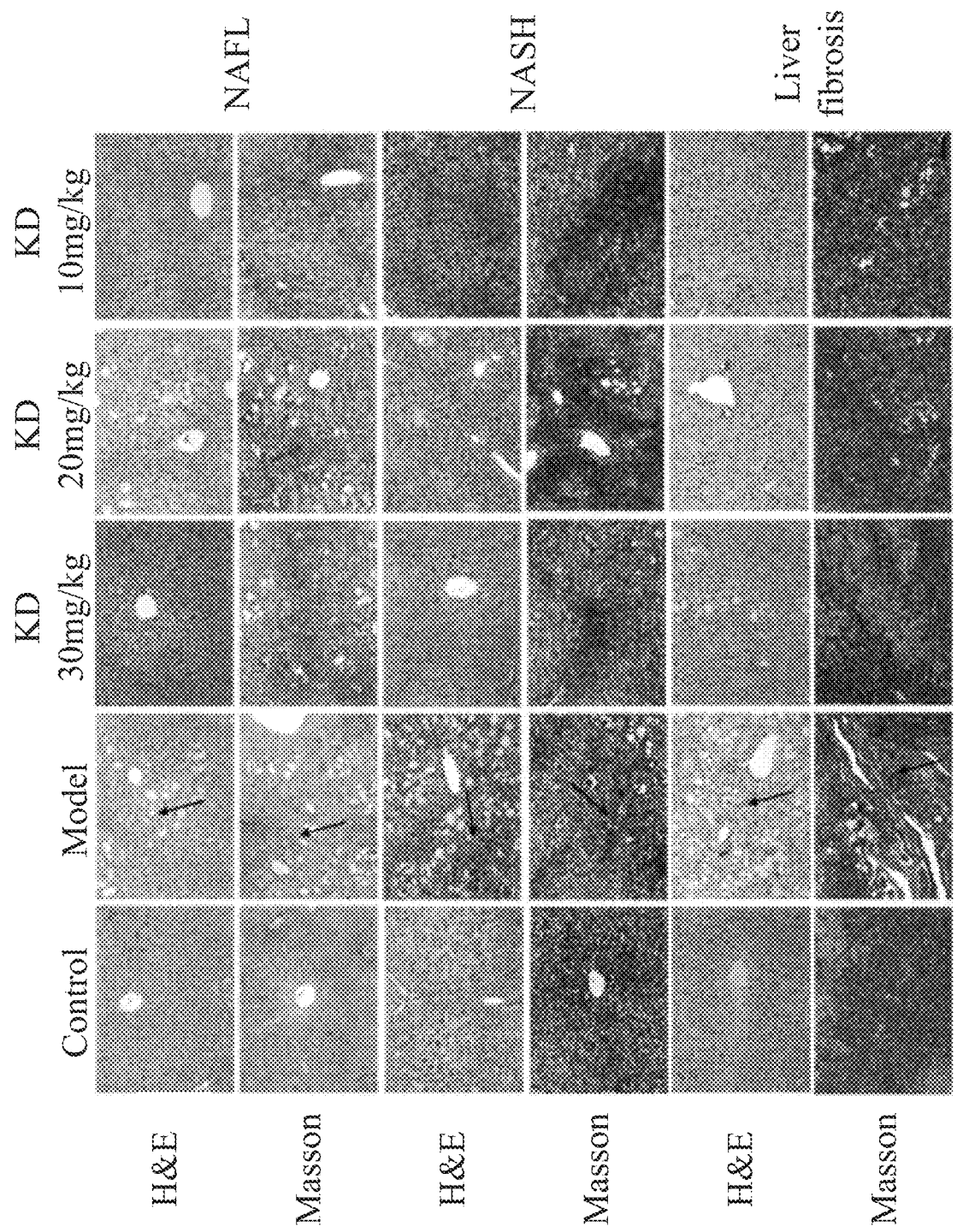
FIGS. 1A-1D show the therapeutic effect of KD in the development of NAFL-NASH-liver fibrosis.
Figure 1B:
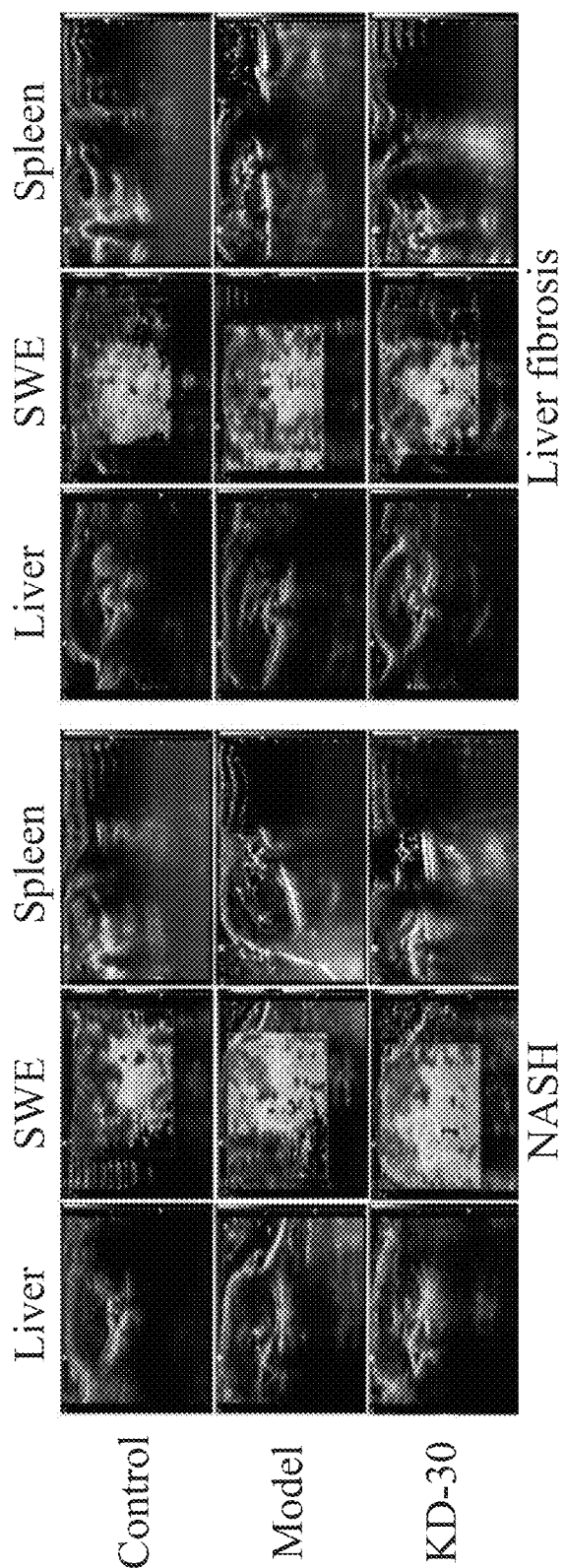
Figure 1C:
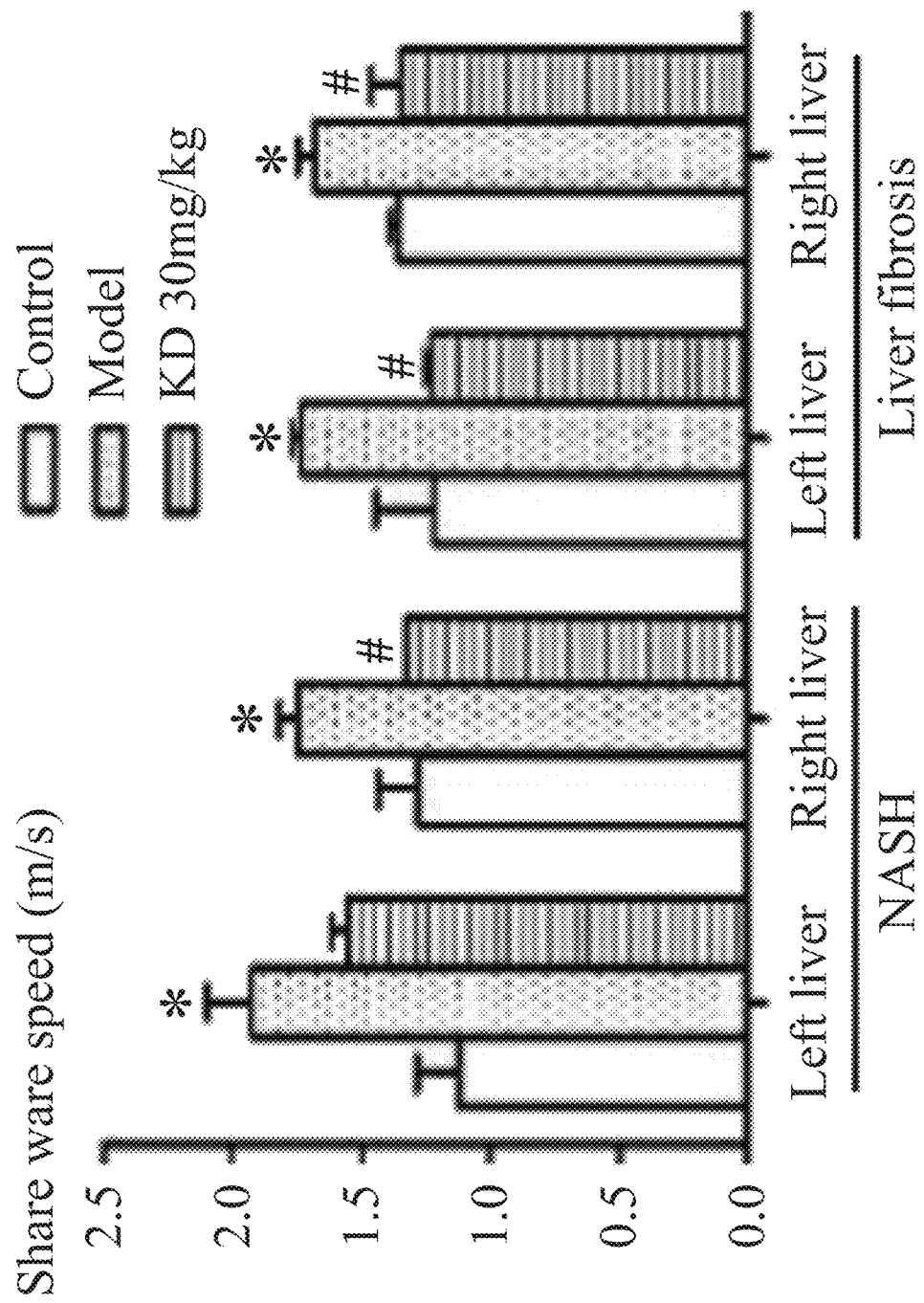
Figure 1D:
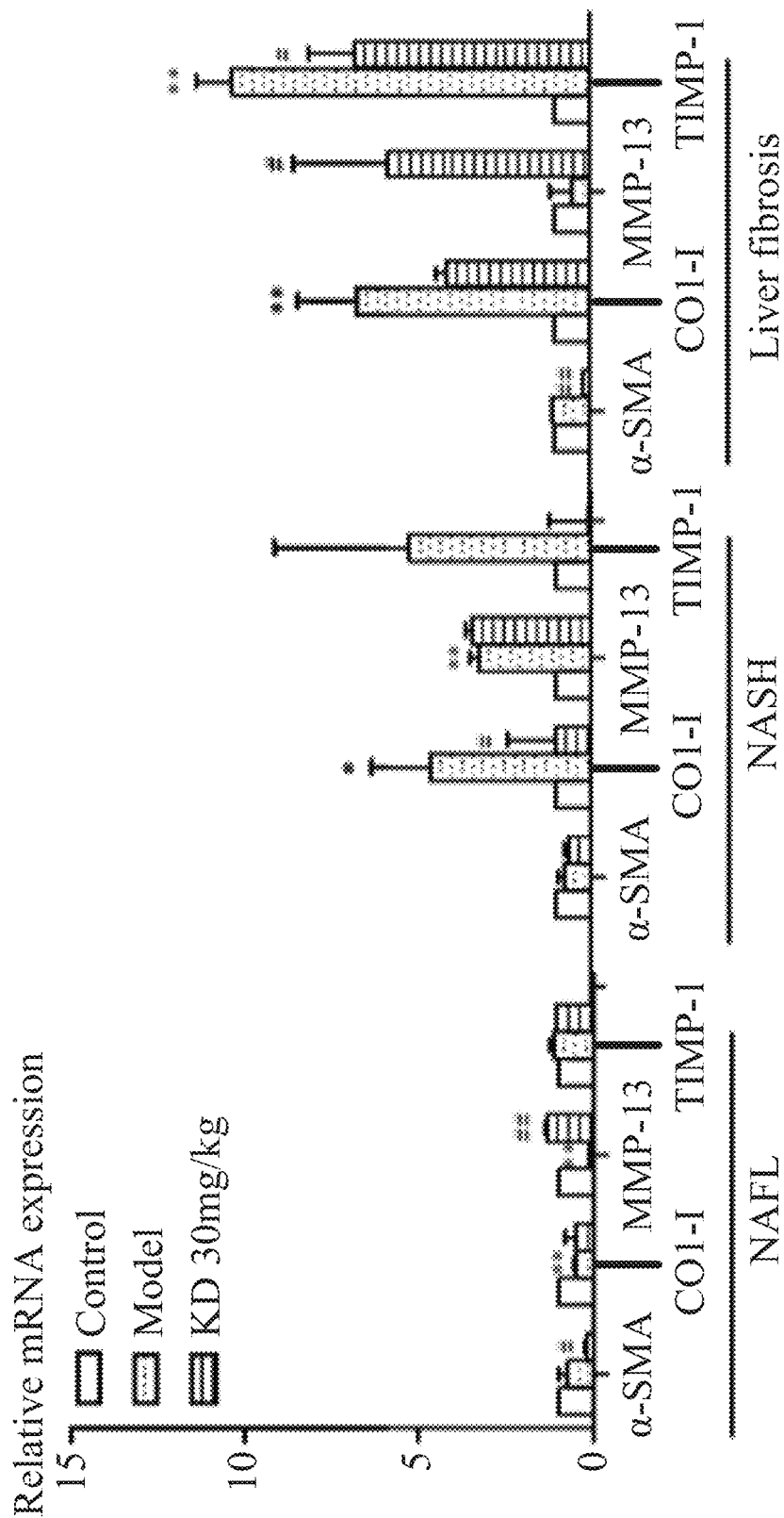
Figures 2A, 2B:
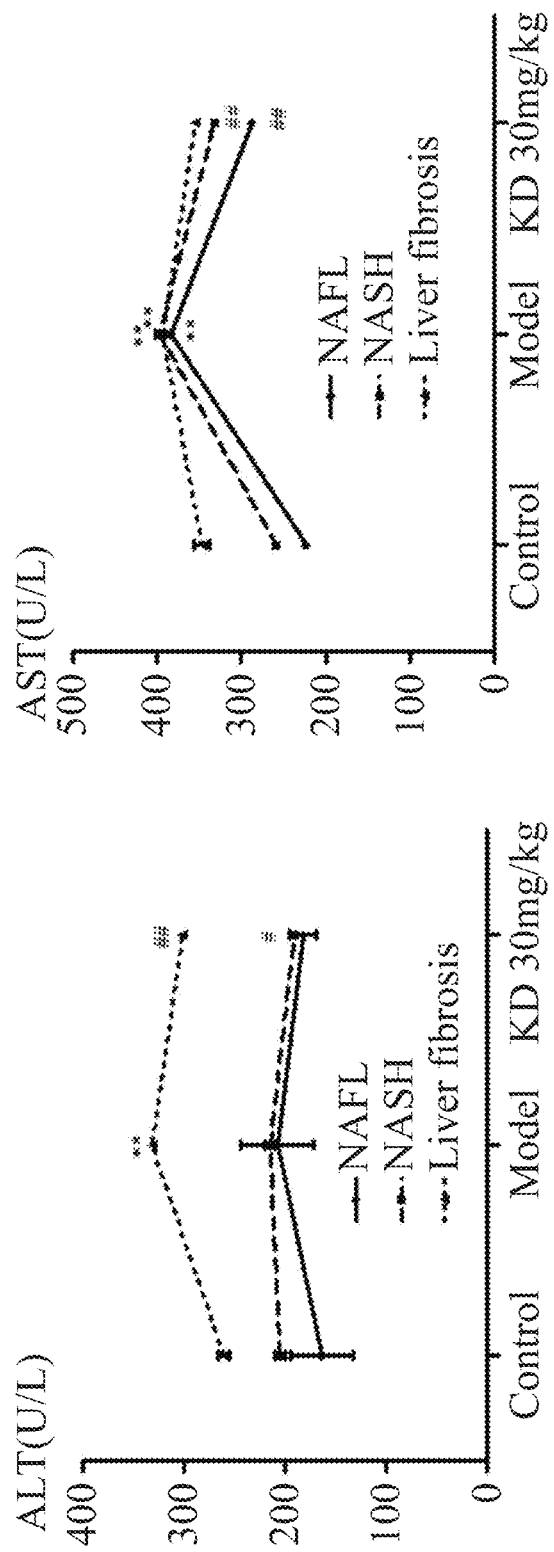
FIGS. 2A-2D show the effects of KD on liver function and oxidative stress of mice with liver fibrosis.
Figures 2C, 2D:
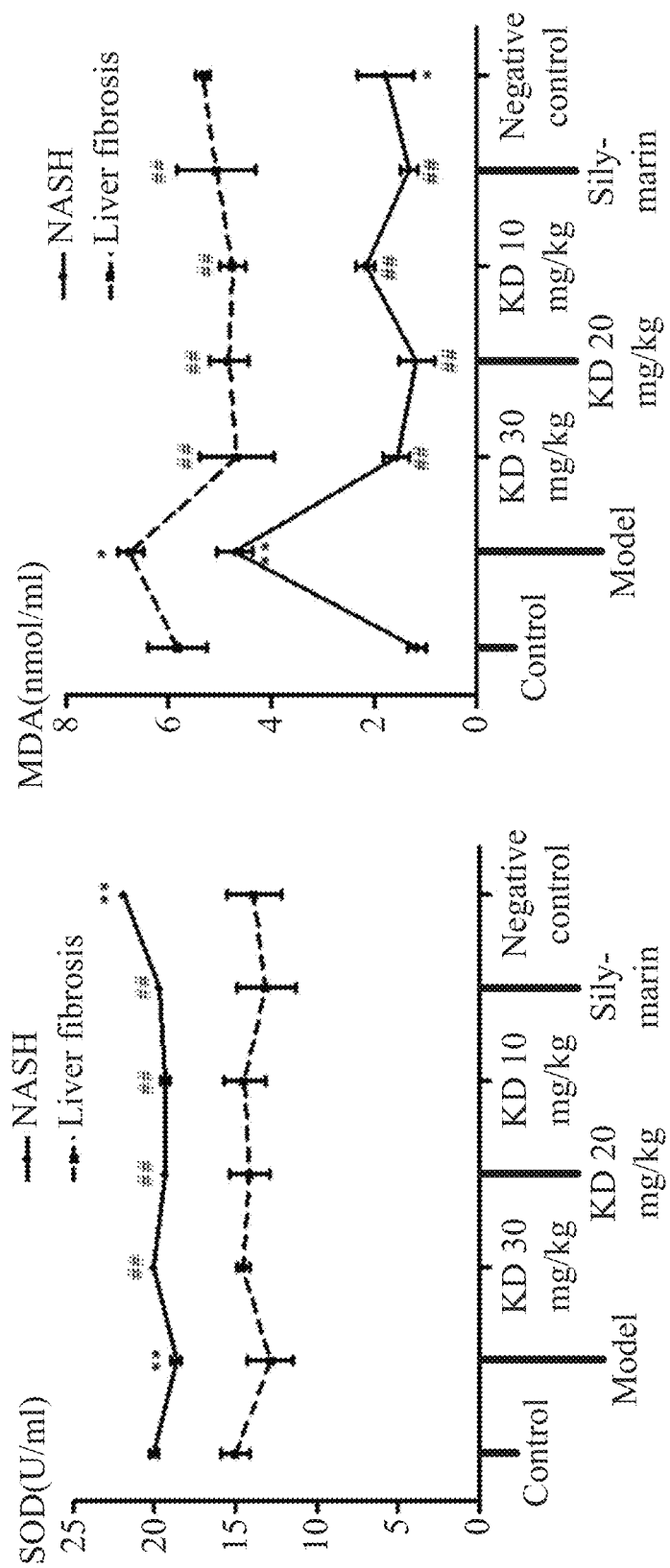

FVB/N mice aged 6-8 weeks were divided into a control group, a model group, a high dose group (30 mg/kg KD), a medium dose group (20 mg/kg KD) and a low dose group (10 mg/kg KD). The serine/threonine kinase (AKT) and transposase plasmids were injected into the liver of the mice by a transposition system through hydrodynamics. The serine/threonine kinase was specifically overexpressed in the liver, and the mice except the control group were modeled. One week later, nonalcoholic fatty liver (NAFL) was formed; two weeks later, steatohepatitis (NASH) was formed; and four weeks later, a primary hepatic fibrosis model was established. In the formation of NAFL-NASH-liver fibrosis, the therapeutic effect of KD was observed. Hematoxylin-eosin (H&E) staining showed that KD could reduce liver histopathological damage in the high dose group (30 mg/kg KD), medium dose group (20 mg/kg KD) and low dose group (10 mg/kg KD); Masson staining showed that KD had inhibitory effect on the fiber formation (see FIG. 1A). Real time shear wave elastography (SWE) was used to detect the development of liver fibrosis and the therapeutic potential of KD. The results showed that in NASH stage, liver disease was in a mild and moderate stage; the changes of the portal vein and inferior vena cava, the thickness and diameter of the left lobe, the oblique diameter of the right lobe, the length and thickness of the spleen were not obvious; when chronic hepatitis developed to liver fibrosis and liver cirrhosis, the inferior vena cava was obviously widened, the thickness and diameter of the left lobe was significantly increased, the spleen was obviously thickened, and the portal vein, the oblique diameter of the right lobe and the spleen tended to widen and lengthen. KD treatment can significantly reduce the width of the inferior vena cava, left lobe thickness, right lobe obliquity and spleen thickness of mice in the high dose group, the middle dose group and the low dose group (see Table 1). The measurement results of the shear wave velocity of SWE showed that the echo velocity of the left and right liver in the model group increased significantly, indicating that the liver tissue was hardened and the fibrosis was severe, and the KD could significantly reduce the shear wave velocity and alleviate the liver fibrosis (see FIG. 1B). The expression of the fibrosis marker genes in liver tissues was detected by qPCR, and the results showed that KD could effectively inhibit the expression of α-smooth muscle actin (α-SMA), collagen I (Col I) and tissue inhibitor of metalloproteinase-1 (TIMP-1) in the liver of mice in the high dose group, the medium dose group and the low dose group, and promoted the expression of matrix metalloproteinase-13 (MMP-13) (see FIG. 1C).

During the development of liver fibrosis, the results of liver function examination showed that the levels of serum alanine transaminase (ALT) and aspartate aminotransferase (AST) in the model group were higher than those in the control group, and decreased after KD treatment; the expression of malondialdehyde (MDA) and superoxide dismutase (SOD) in the model group increased, and the activity of SOD decreased. KD treatment could reverse these oxidative stress injuries (see FIGS. 2A-2D).

During the development of liver fibrosis, KD treatment reduced the secretion of the inflammatory cytokines IFN-γ, TNF-α and IL-2 of the proinflammatory cells Th1 in the high dose group, the medium dose group and the low dose group, promoted the secretion of the inflammatory cytokine IL-10 of the Th2-type cells, and inhibited the release of the inflammatory response marker NO (see Tables 2, 3.)

Figure 3A:
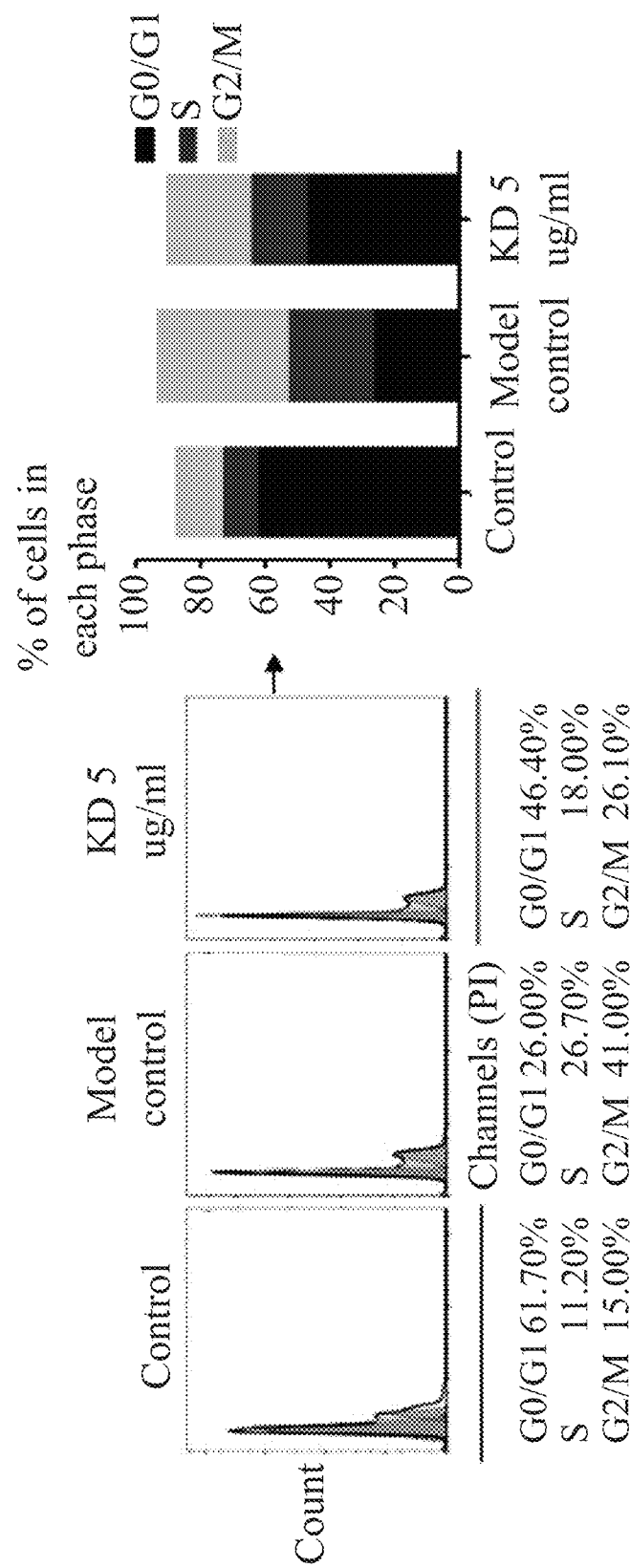
FIGS. 3A-3G show the inhibition of KD on the hepatic stellate cells.
Figure 3B:
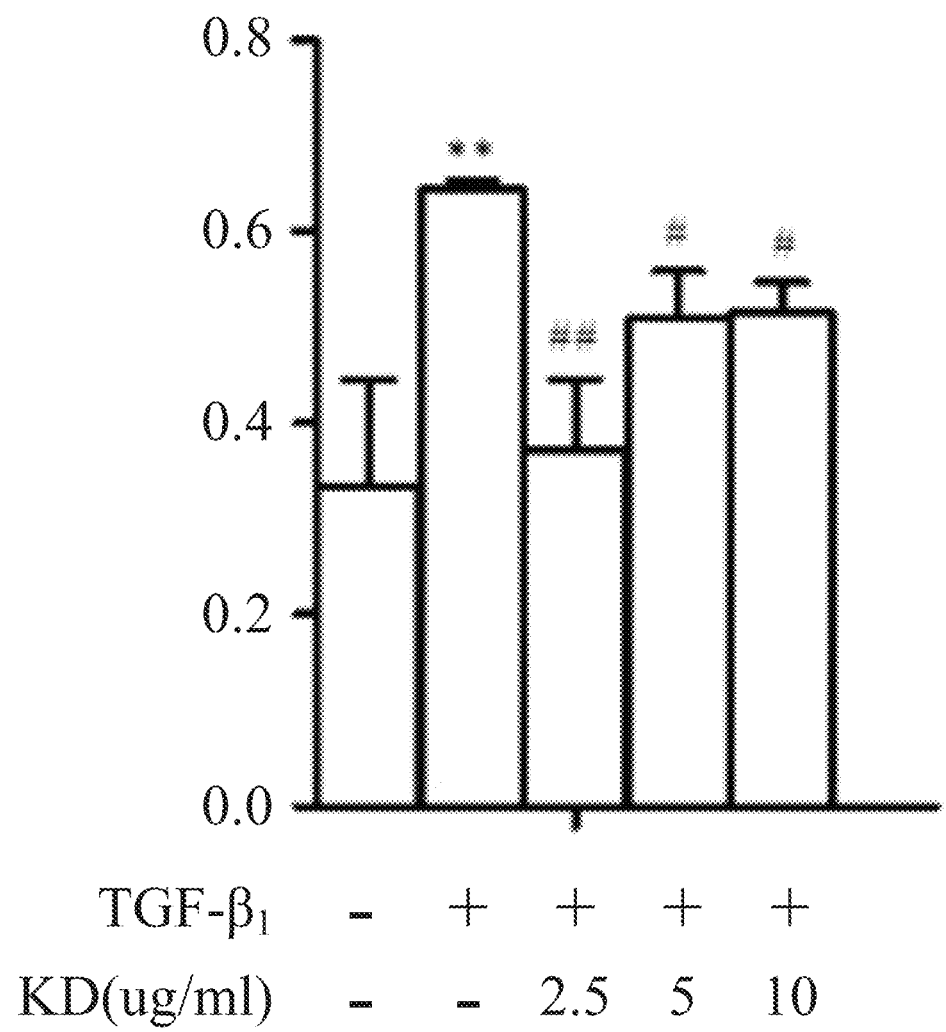
Figure 3C:
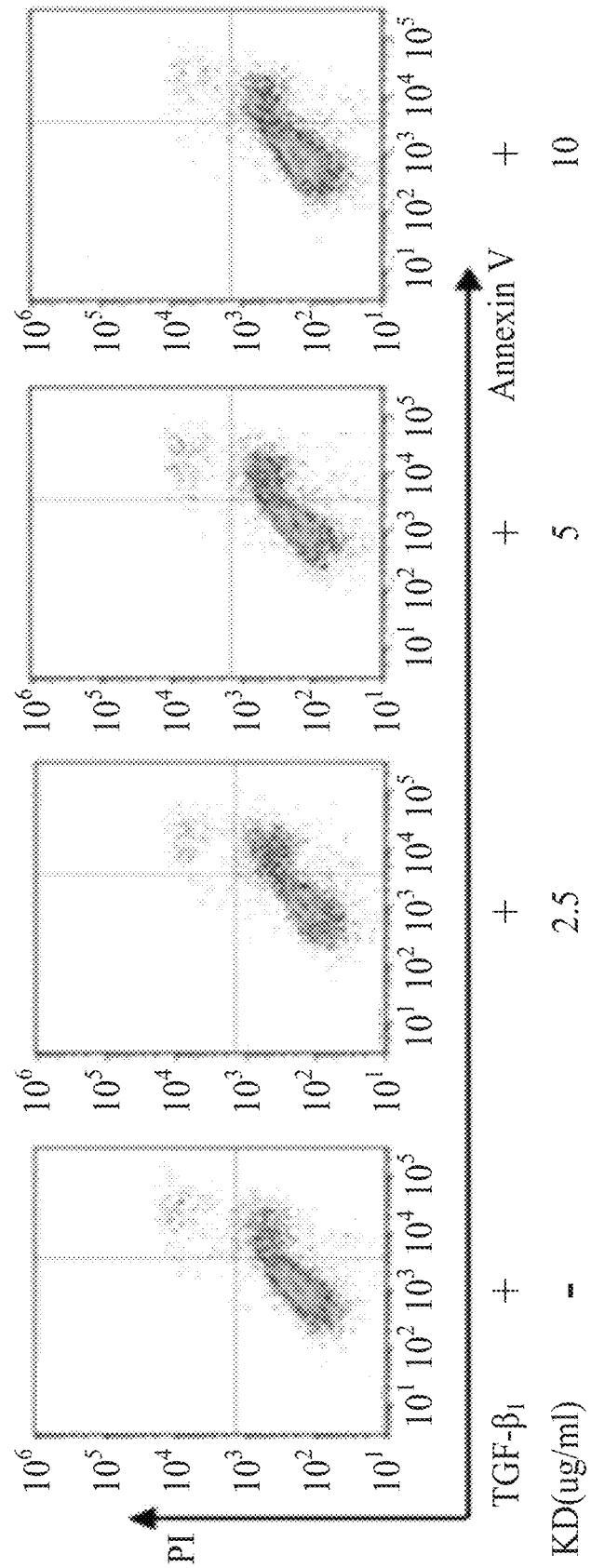
Figure 3D:
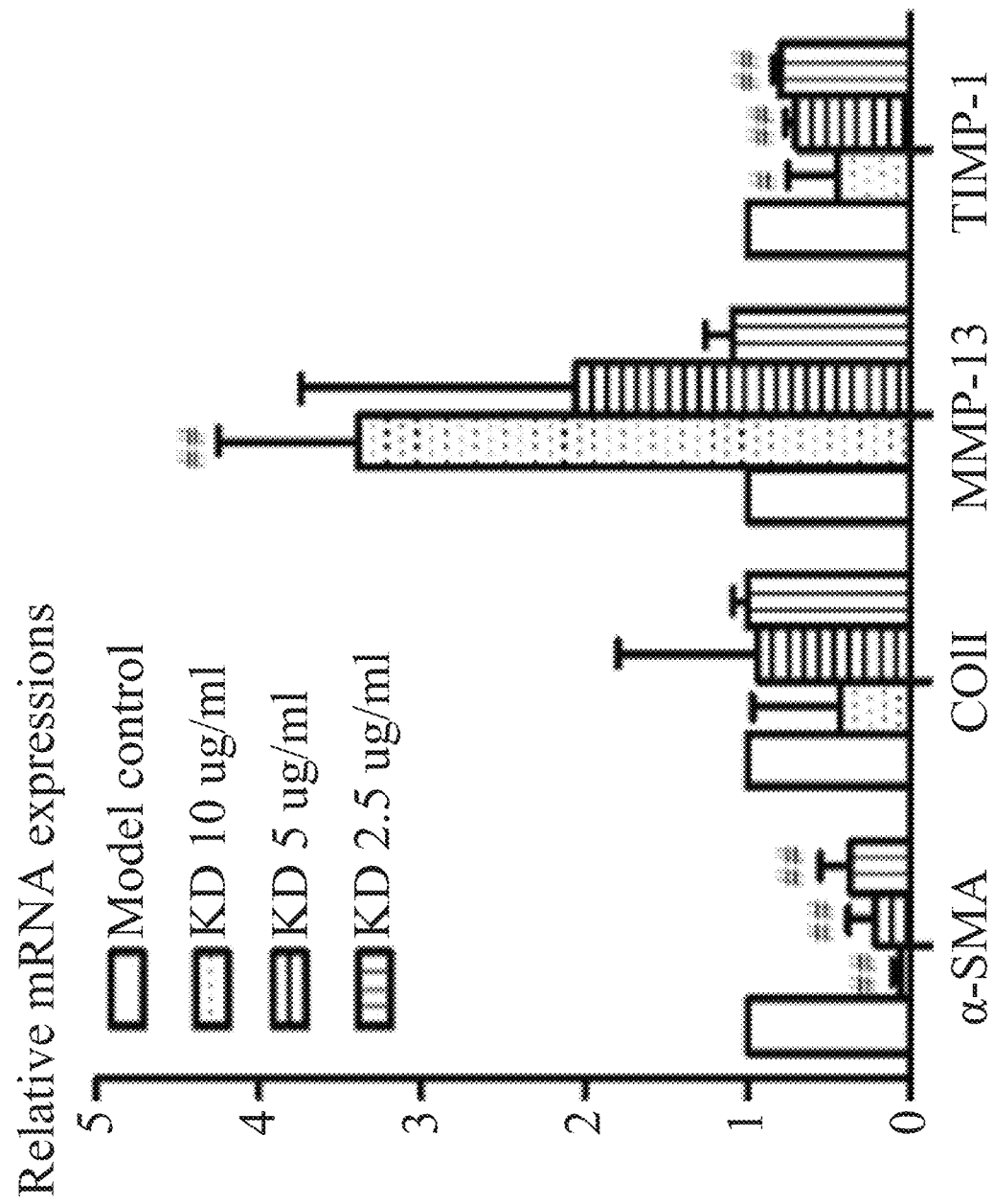
Figure 3E:
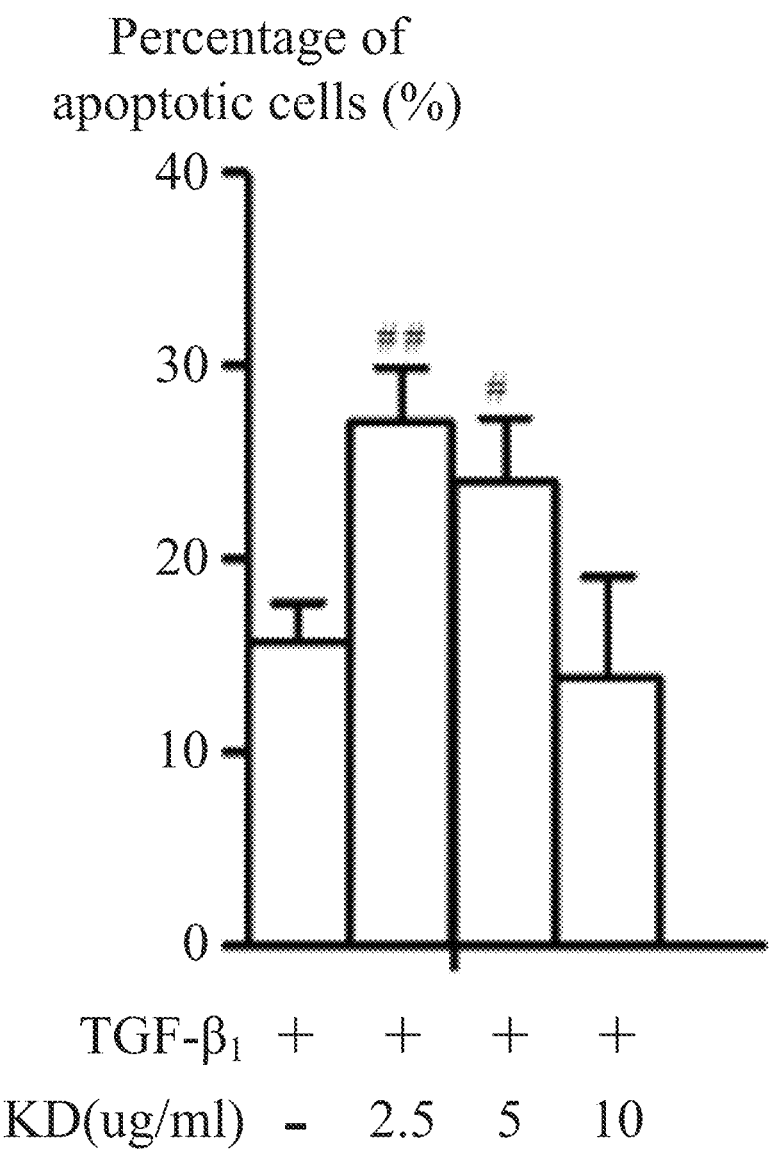
Figures 3F, 3G:
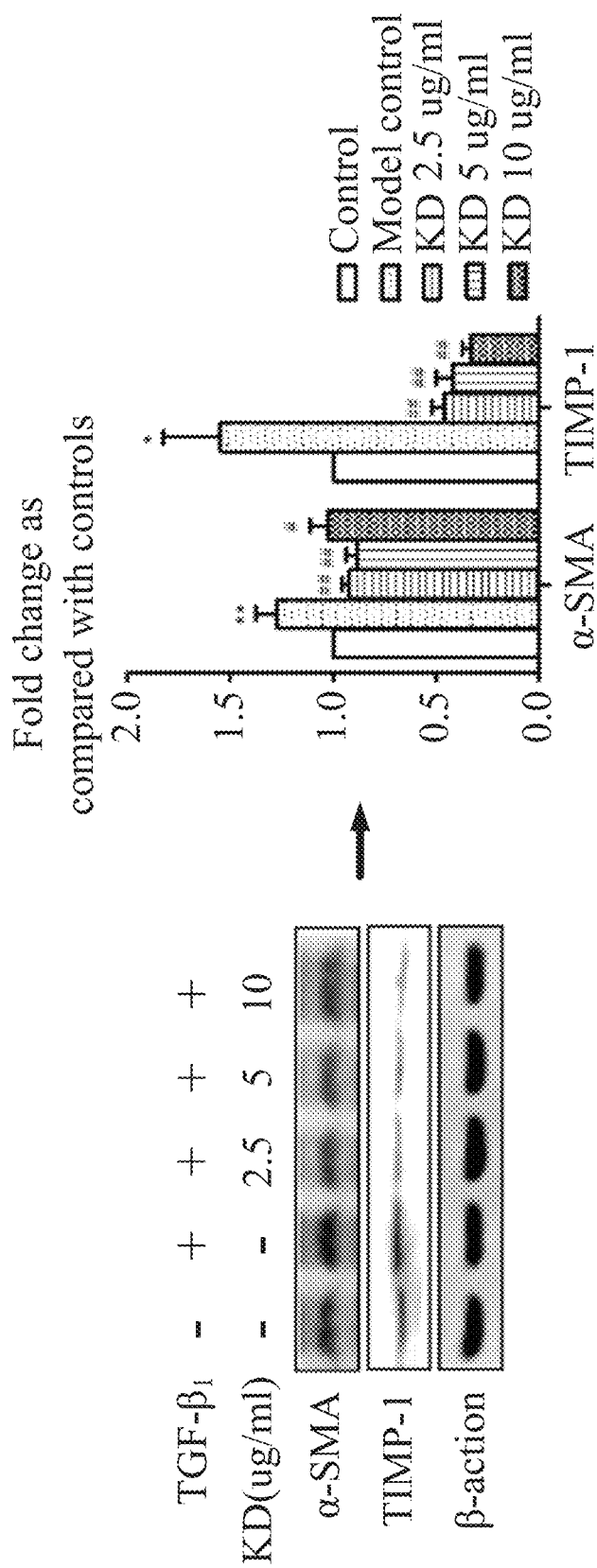

The therapeutic effect of KD was dose-dependent, which was similar to that of silymarin, and better than that of silymarin in some indexes. At the same time, KD in the control group did not affect the secretion of ALT, AST and inflammatory cytokines. HSCs are important cells involved in liver fibrosis. The activation of HSCs is a key element of the development of liver fibrosis, and its apoptosis can reverse liver fibrosis. Different concentrations of KD were used to activate the hepatic stellate cells (HSC-T6) activated by TGF-$β_1$. The results showed that KD could block the cell cycle of the HSC-T6 in the G0/G1 phase, inhibit its proliferation and promote its apoptosis (see FIGS. 3A-3C). qPCR and Western blot also showed that the activation of the HSC-T6 cells and the expression of genes and proteins related to the secretion of ECM were also inhibited by KD (see FIG. 3D). The results are shown in Tables 1-3.

TABLE 1

Type B ultrasonic detector of the liver and spleen (mean ± SD, n = 3).

| | Group | Oblique diameter of right lobe of liver (mm) | Thickness of the left lobe of liver (mm) | Diameter of inferior vena cava (mm) | Diameter of hepatic portal vein (mm) | Length of the spleen (mm) | Thickness of the spleen (mm) |
|---|---|---|---|---|---|---|---|
| NAFL | Control | 7.65 ± 0.35 | 6.20 ± 1.56 | 1.25 ± 0.35 | 0.75 ± 0.07 | 5.25 ± 1.34 | 1.75 ± 0.21 |
| | Model | 8.15 ± 0.21 | 7.30 ± 1.70 | 1.50 ± 0.28 | 0.85 ± 0.07 | 6.95 ± 1.34 | 2.40 ± 0.42 |
| | KD (30 mg/kg) | 7.25 ± 0.21# | 4.35 ± 1.20 | 1.50 ± 0.14 | 0.75 ± 0.07 | 5.40 ± 0.99 | 1.65 ± 0.07 |
| Liver fibrosis | Control | 8.10 ± 0.14 | 3.85 ± 0.21 | 1.15 ± 0.07 | 0.60 ± 0.14 | 7.75 ± 0.64 | 2.15 ± 0.07 |
| | Model | 9.30 ± 0.99 | 5.50 ± 0.42* | 1.80 ± 0.14** | 0.85 ± 0.21 | 10.60 ± 4.53 | 3.15 ± 0.21** |
| | KD (30 mg/kg) | 8.35 ± 0.78 | 3.65 ± 0.49# | 1.15 ± 0.07## | 0.65 ± 0.07 | 5.40 ± 0.71 | 1.50 ± 0.14## |

Note:
**P <0.01 compared with control group, #P <0.05, ##P <0.01 compared with model group

TABLE 2

Effect of KD on the secretion of inflammatory cytokines in NASH (mean ± SD, n = 6).

| Group | IL-2(pg/mL) | IL-10(pg/mL) | IL-12(pg/mL) |
|---|---|---|---|
| Control | 156.64 ± 19.19 | 131.77 ± 4.43 | 109.47 ± 10.02 |
| Model | 228.64 ± 1.80** | 62.52 ± 1.25** | 129.72 ± 2.36* |
| KD (30 mg/kg) | 169.13 ± 13.10##Δ | 91.20 ± 0.56##ΔΔ | 106.38 ± 1.18##Δ |
| KD (20 mg/kg) | 133.29 ± 4.57## | 84.12 ± 0.23##ΔΔ | 123.05 ± 0.71## |
| KD (10 mg/kg) | 101.31 ± 9.79##Δ | 66.84 ± 2.73 | 127.64 ± 2.71 |
| Silymarin | 137.23 ± 17.66## | 61.45 ± 1.27 | 117.55 ± 6.60 |
| Negative control | 128.46 ± 0.75# | 126.79 ± 5.62 | 115.64 ± 14.73 |

| Group | IFN-γ(pg/mL) | NO(μmol/L) | TNF-α(pg/mL) |
|---|---|---|---|
| Control | 7.43 ± 1.01 | 51.38 ± 3.04 | 2.03 ± 0.36 |
| Model | 36.71 ± 1.52** | 56.04 ± 1.24* | 6.63 ± 0.95** |
| KD (30 mg/kg) | 32.43 ± 0.98## | 48.15 ± 1.86##ΔΔ | 2.35 ± 0.10##ΔΔ |
| KD (20 mg/kg) | 33.86 ± 0.65# | 51.38 ± 1.08##ΔΔ | 3.03 ± 0.26##ΔΔ |
| KD (10 mg/kg) | 36.71 ± 0.32ΔΔ | 56.22 ± 5.32ΔΔ | 4.10 ± 0.04## |
| Silymarin | 33.14 ± 1.01# | 40.98 ± 1.64## | 4.15 ± 0.50## |
| Negative control | 29.93 ± 1.80## | 38.83 ± 0.62## | 2.59 ± 0.45 |

TABLE 3

Effect of KD on the secretion of inflammatory cytokines in liver fibrosis (mean ± SD, n = 6)

| Group | IL-2(pg/mL) | IL-10(pg/mL) | IL-12(pg/mL) |
|---|---|---|---|
| Control | 98.30 ± 4.16 | 197.20 ± 7.78 | 186.31 ± 2.72 |
| Model | 121.10 ± 6.65** | 110.71 ± 3.82** | 404.00 ± 9.50** |
| KD (30 mg/kg) | 93.91 ± 2.05##ΔΔ | 140.44 ± 7.64## | 242.08 ± 5.44## |
| KD (20 mg/kg) | 104.72 ± 0.71##ΔΔ | 206.66 ± 1.91##ΔΔ | 174.77 ± 2.72## |
| KD (10 mg/kg) | 101.73 ± 0.70##ΔΔ | 128.28 ± 24.84 | 253.62 ± 7.20## |
| Silymarin | 123.17 ± 0.74 | 135.04 ± 4.40## | 205.54 ± 2.72## |
| Negative control | 91.02 ± 0.68 | 186.12 ± 3.82 | 136.31 ± 8.16** |

| Group | IFN-γ(pg/mL) | NO(μmol/L) | TNF-α(pg/mL) |
|---|---|---|---|
| Control | 72.43 ± 4.85 | 57.57 ± 7.70 | 5.36 ± 0.33 |
| Model | 89.57 ± 3.30** | 57.57 ± 3.50 | 11.83 ± 1.31* |
| KD (30 mg/kg) | 53.38 ± 1.65##ΔΔ | 59.06 ± 1.40 | 2.38 ± 0.57## |
| KD (20 mg/kg) | 57.19 ± 1.65##ΔΔ | 54.11 ± 15.40 | 8.41 ± 0.52 |
| KD (10 mg/kg) | 85.76 ± 8.25 | 52.13 ± 1.40 | 13.46 ± 9.31ΔΔ |
| Silymarin | 79.10 ± 1.65# | 52.52 ± 4.90 | 5.93 ± 0.85## |
| Negative control | 71.48 ± 8.25 | 60.05 ± 14.00 | 2.58 ± 0.20 |

**P < 0.01 compared with control group; #P < 0.05, ##P < 0.01 compared with model group; ΔP < 0.05, ΔΔP < 0.01 compared with silymarin group.

Conclusions: KD can effectively prevent the development of liver fibrosis and improve liver injury. The mechanism is that the compound can reduce the expression of fibrosis marker genes, improve liver function, oxidative stress injury, and reduce the secretion of inflammatory cytokines and the like.

EXAMPLE 2

Treatment of Acute Liver Failure using Kinsenoside

60 SPF male C57 mice were purchased and raised in the SPF experimental animal center of Tongji Medical College of Huazhong University of Science and Technology. The mice were provided with standard diet and drinking water. The room temperature was controlled at 23±2° C. After 7 days of adaptive feeding, the mice were administered by intragastric administration. The mice were divided into a control group (administered with distilled water), a model group (administered with distilled water), a high dose group (KD-400 group, 400 mg/kg KD), a medium dose group (KD-200 group, 200 mg/kg KD) and a low dose group (KD-100 group, 100 mg/kg KD), ten mice each group. The mice were weighed the next day, and were continuously administered with above drugs respectively for 10 days. One hour after the last gavage, the mice were injected intraperitoneally (the control group was injected with the same amount of normal saline). The agent for the intraperitoneal injection was galactosamine (D-GalN, 500 mg/kg)+lipopolysaccharide (LPS, *Eschericia coli* 0111: B4, 5 ug/kg), all purchased from Sigma-Aldrich.

Figures 4A, 4B:
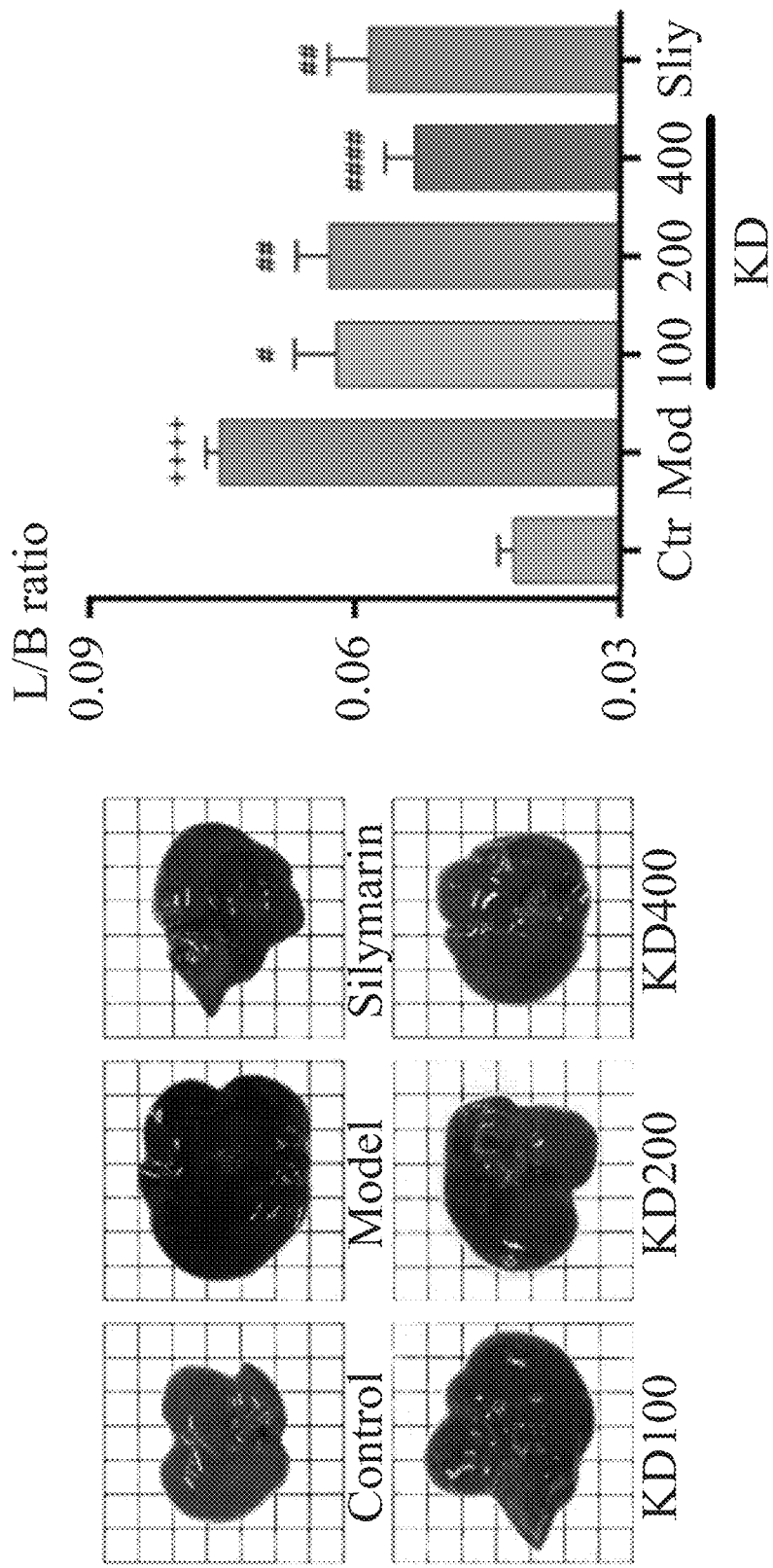
FIGS. 4A-4J show the protective effect of KD on acute liver failure verified by H&E tissue staining, biochemical kits (ALT, AST, MDA, SOD) and flow cytometry. In the picture.
Figures 4C, 4D:
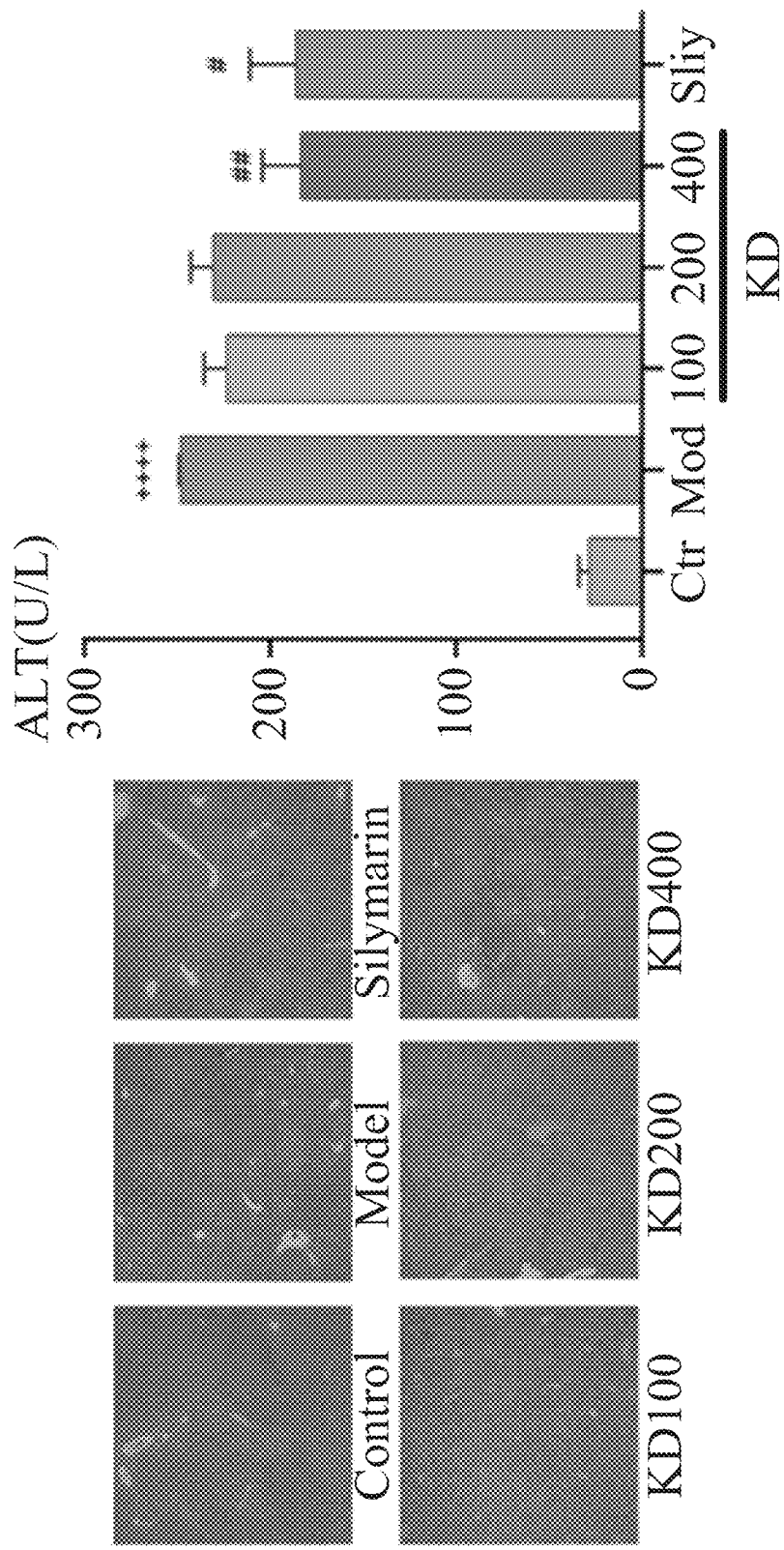

The experimental results showed that, compared with the control group, the liver of the model group showed a lot of bleeding and swelling, showing abnormal black red. KD and silymarin can significantly improve the bleeding and swelling of the liver (see FIG. 4A). According to the value of liver weight/body weight, the liver swelling was quantified, which confirmed that KD and silymarin could improve the weight gain of liver bleeding (see FIG. 4B). Hematoxylin eosin (H & E) staining results show that KD can reduce liver histopathological damage in high KD dose group, middle KD dose group and low KD dose group, with excellent effect in high dose and greatly improved liver bleeding (see FIG. 4C).

Figures 4E, 4F:
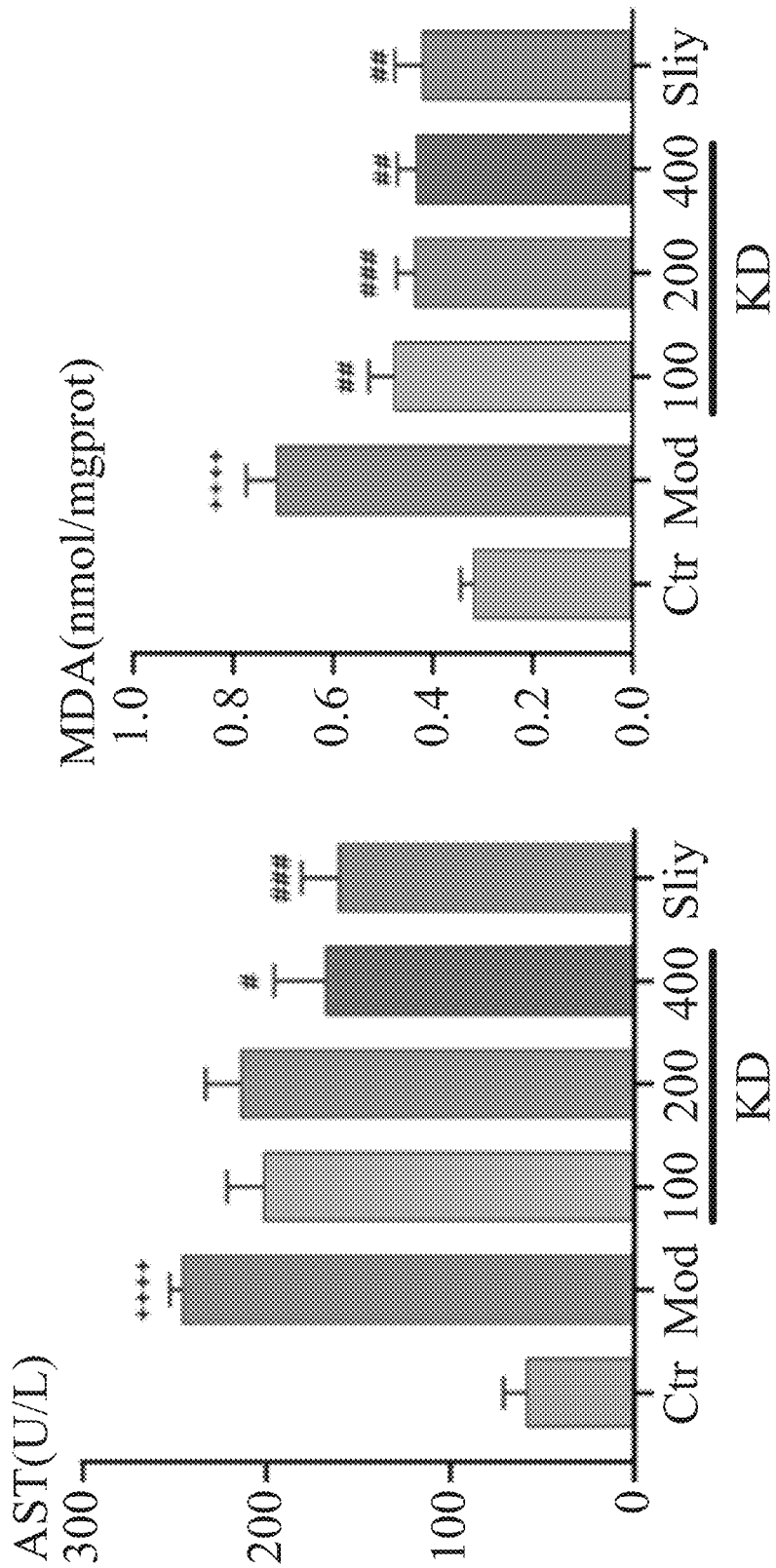
Figures 4G, 4H:
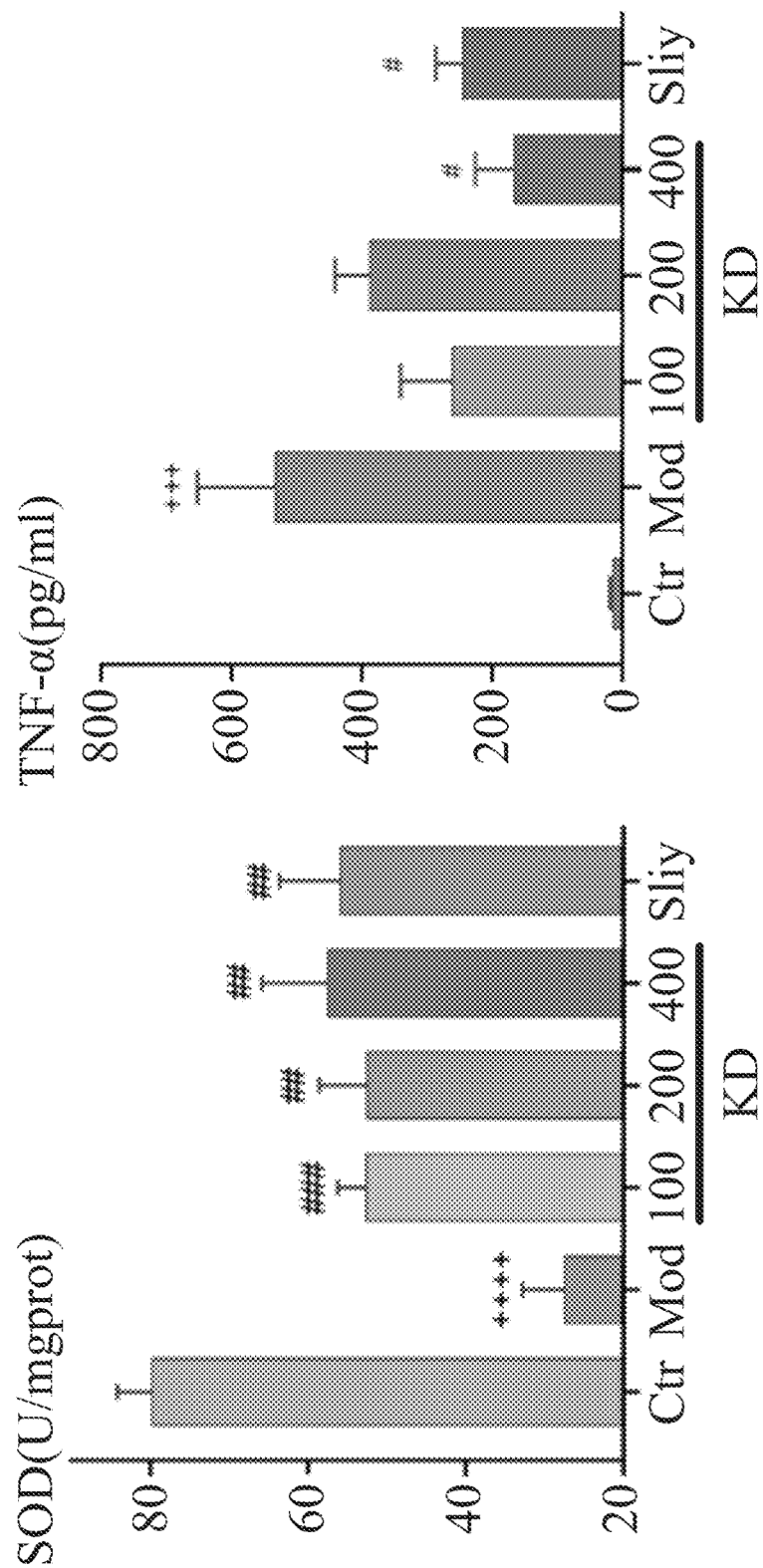

In the development of acute liver failure, a large number of liver cells were destroyed, accompanied by a sharp rise of transaminase. The results of liver function examination showed that the levels of ALT and AST in the model group were higher than those in the control group, and the levels of ALT and AST in the KD and silymarin groups were reduced (see FIG. 4D and FIG. 4E); the expression of MDA and the activity of SOD in the model group were increased, and KD treatment could effectively protect the liver of the treatment group, protect the mice from the oxidative stress injuries (see FIG. 4F and FIG. 4G).

Figures 4I, 4J:
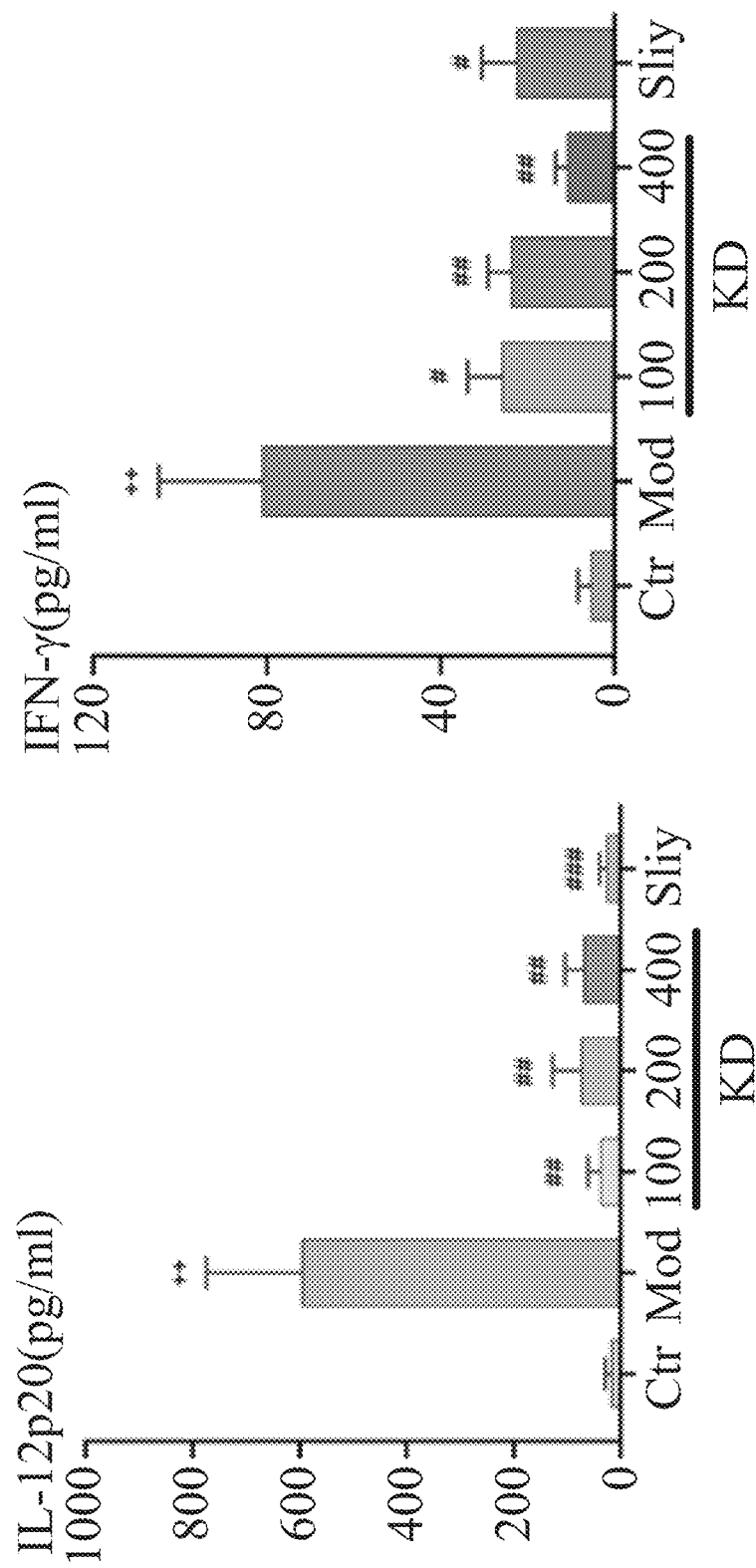

In the development of acute liver failure of the model group, there was a sharp increase of inflammatory cytokines such as TNF-α, IL-12p70, IFN-γ. Flow cytometry kit was used to measure the inflammatory cytokines in each group. The results showed that the increase of the inflammatory cytokines in the high dose group, the medium dose group and the low dose group was inhibited, that is, KD had significant anti-inflammatory effect in the model, and its effect was better than that of positive drugs in some indexes (see FIG. 4H, FIG. 4I, FIG. 4J).

Figure 5A:
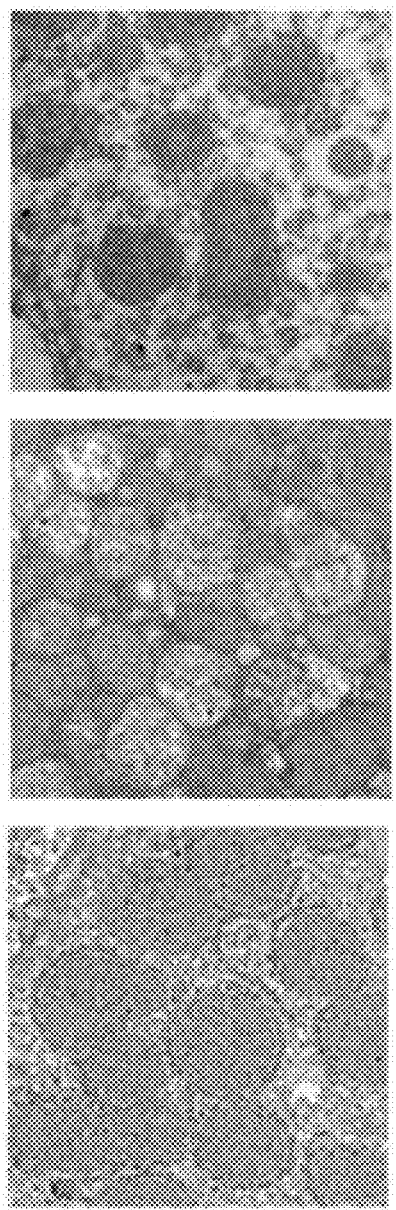
Figure 5B:
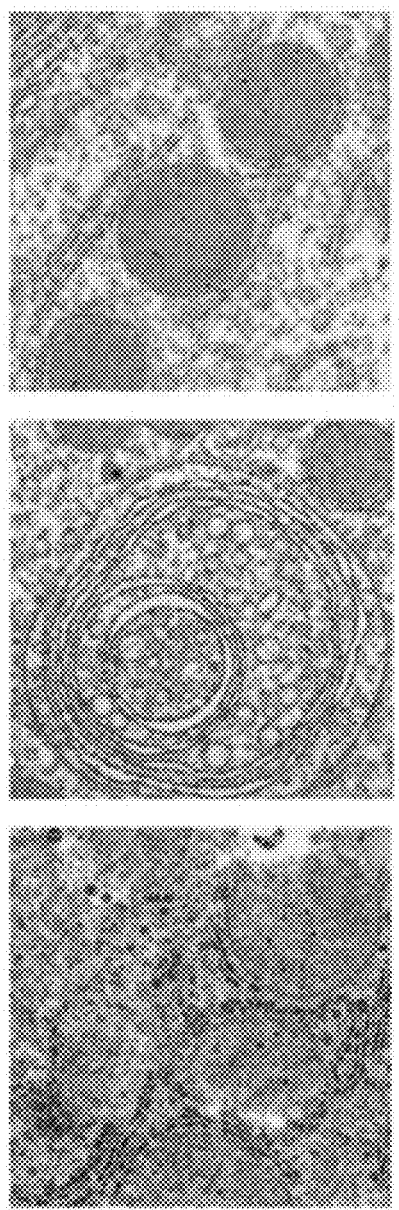
Figures 6A, 6B:
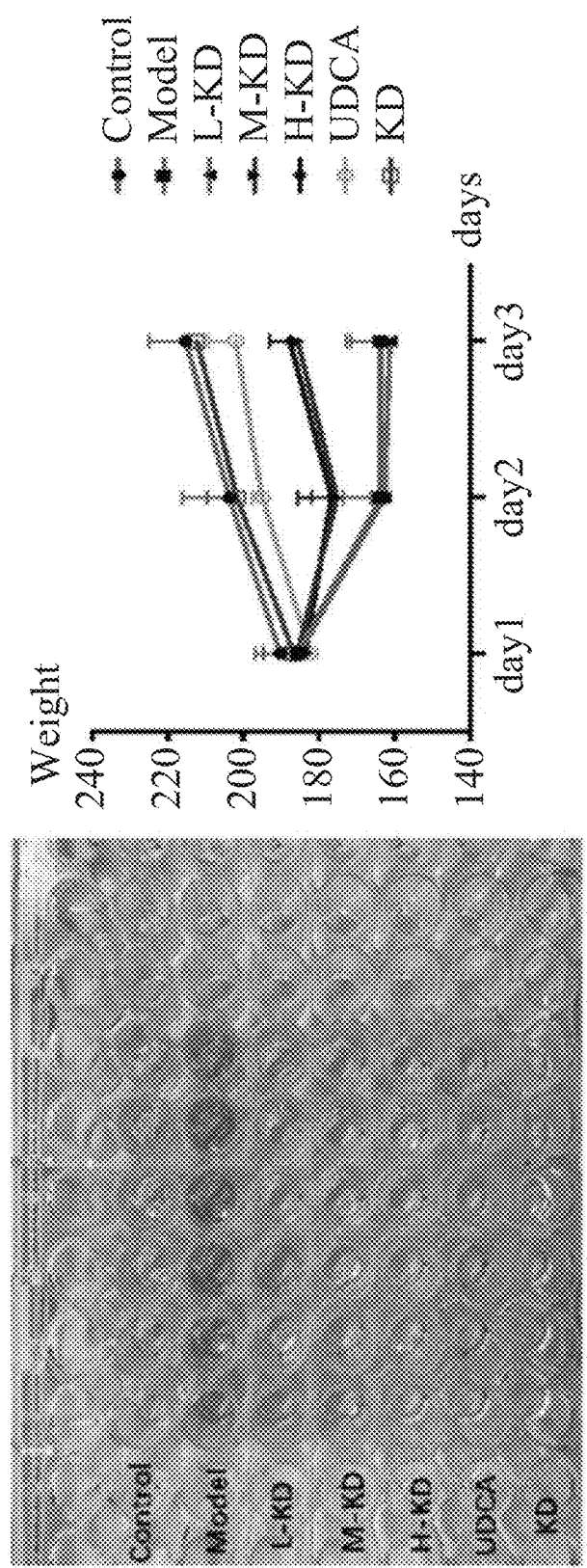
FIGS. 6A-6D show the effect of KD on the physical signs of the rat model of cholestatic liver injury induced by ANIT.
Figures 6C, 6D:
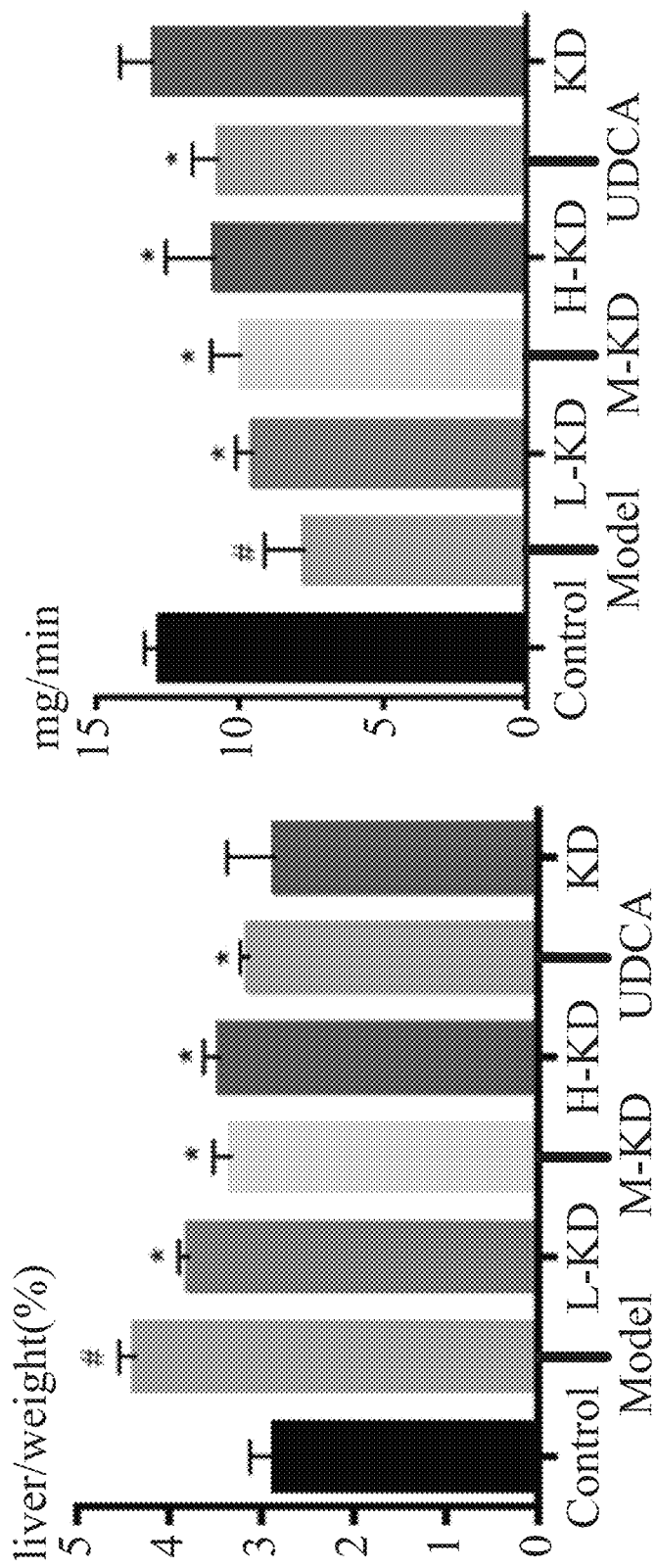

The mitochondrial structure of the liver of the mice was observed by transmission electron microscopy. It was found that the mitochondrial structure of the liver of the mice in the model group was largely destroyed and the inner membrane of the mitochondria was broken. After KD was given, the mitochondrial structure of the liver of the mice was protected and the mitochondrial function was preserved. At the same time, the endoplasmic reticulum stress, the expansion and vesiculation of the endoplasmic reticulum were observed extensively in the model group, and KD could down-regulate the process (see FIG. 5A and FIG. 5B). Tunel fluorescence staining was used to verify that KD could inhibit abnormal apoptosis of the liver cells and improve liver failure (see FIG. 5C).

The expression of apoptotic protein in the control group, the model group and the high-dose group was detected using Western blot. The results showed that the apoptotic marker protein PARP (poly ADP-Ribose Polymerase) and C-C3 (Cleaved Caspase-3) increased significantly after the establishment of the model. KD could down regulate the apoptotic protein, reduce the abnormal apoptosis of hepatocytes and protect the liver (see FIG. 5D and FIG. 5E).

Conclusion: kinsenoside can effectively prevent the development of acute liver failure and reduce liver damage. The mechanism is that the compound can reduce the expression of fibrosis marker genes, improve liver function, oxidative stress injury, and reduce the secretion of inflammatory cytokines and the like.

EXAMPLE 3

Treatment of Intrahepatic Cholestasis using Kinsenoside

42 SPF SD mice were purchased and raised in the SPF experimental animal center of Tongji Medical College of Huazhong University of Science and Technology. They were provided with standard diet and drinking water. The room temperature was controlled at 23±2° C. After 3 days of adaptive feeding, they were given drugs by intragastric administration. 42 SD mice were randomly divided into 7 groups (normal control group, ANIT model group, KD low-dose group, KD medium dose group, KD high-dose group, UDCA positive control group and KD negative control group), 6 mice in each group were weighed and recorded daily. 3 days later, the model group, KD group and UDCA positive control group were provided with 75 mg/kg ANIT by intragastric administration to induce intrahepatic cholestasis, while the normal control group and KD negative control group were given 2 mL normal saline by intragastric administration. 12 hours later, the low dose group was administrated by gavage of 50 mg/kg KD, the medium dose group was administrated by gavage of 100 mg/kg KD, and the high dose group was administrated by gavage of 200 mg/kg KD, the positive control group was administrated by gavage of 80 mg/kg UDCA, the KD negative control group was administrated by gavage of 100 mg/kg KD, and the normal control group and the model group was administrated by gavage of 2 mL of normal saline. Thereafter, the drug was given again every 24 hours for 3 times, and the animals in each group were fasted (water was provided) after the third time. 72 hours later, the animals were killed and samples were collected.

The effects of KD on the plasma color, weight gain, organ coefficient and bile acid flow rate of ANIT induced cholestasis mice were shown in FIGS. 6A-6D. It can be seen from FIG. 6A that the plasma color of the ANIT induced cholestasis mice was obviously dark yellow, which may be the result of the increase of total bilirubin and direct bilirubin in the plasma. After administration with KD or UDCA, the plasma color turned light yellow similar to that of the normal control group. According to FIG. 6B, the weight change curve of mice shows that after administration of 75 mg/kg ANIT by gavage, the weight of mice was significantly lower than that of the normal control group and the KD negative control group, and the weight growth of the mice with cholestasis in the UDCA treatment group was similar to that of the normal control group. Although the body weight of the mice with cholestasis treated with different doses of KD decreased, the body weight loss of the mice with cholestasis treated with the medium and high doses of KD was not as significant as that of the ANIT model group. According to the organ coefficient in FIG. 6C, the ratio of liver weight to body weight of the mice after KD or UDCA treatment was lower than that of the ANIT model group. According to bile acid flow rate change chart in FIG. 6D, the bile flow rate of the ANIT induced cholestasis mice was significantly lower than that of the normal control group, while the bile flow rate of the mice after KD or UDCA treatment was significantly higher than that of the model group. These results suggest that KD can alleviate the liver injury induced by ANIT in the mice with intrahepatic cholestasis.

Figures 7A, 7B:
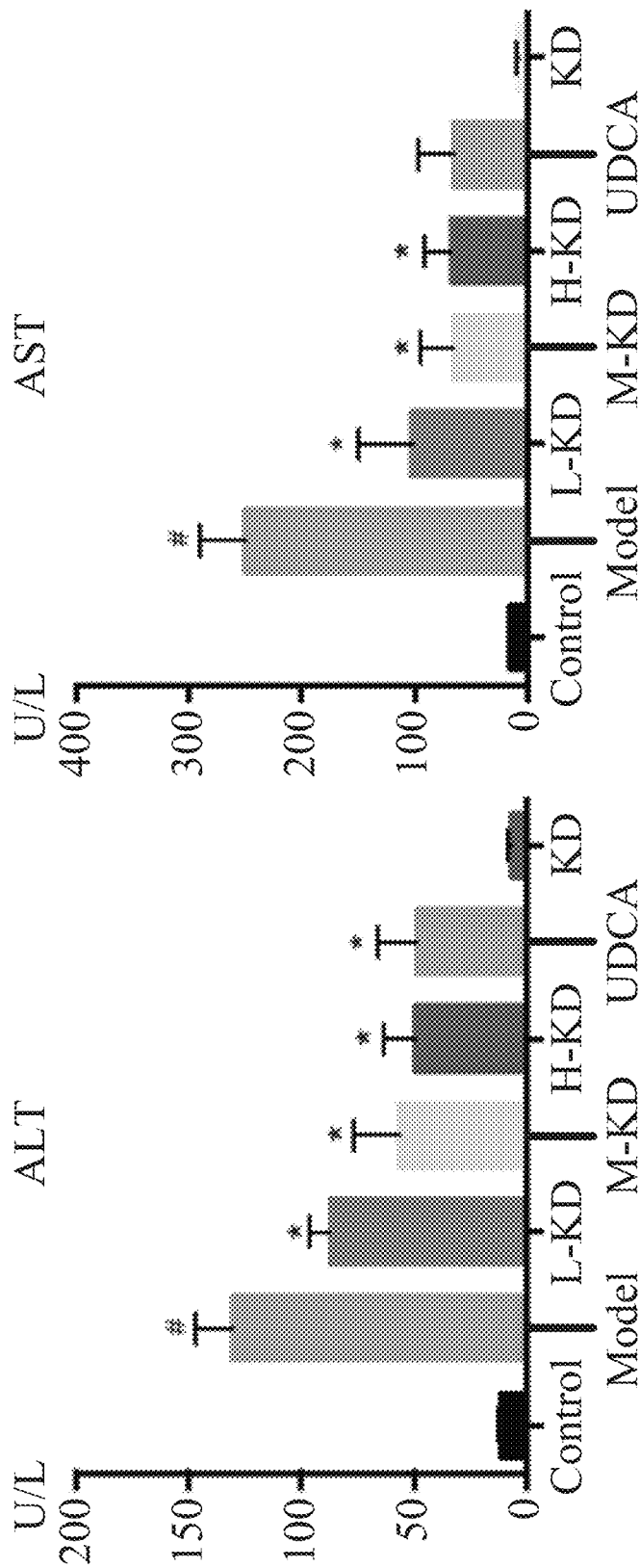
FIGS. 7A-7F show the effect of KD on plasma biochemical parameters in cholestasis mice induced by ANIT.
Figures 7C, 7D:
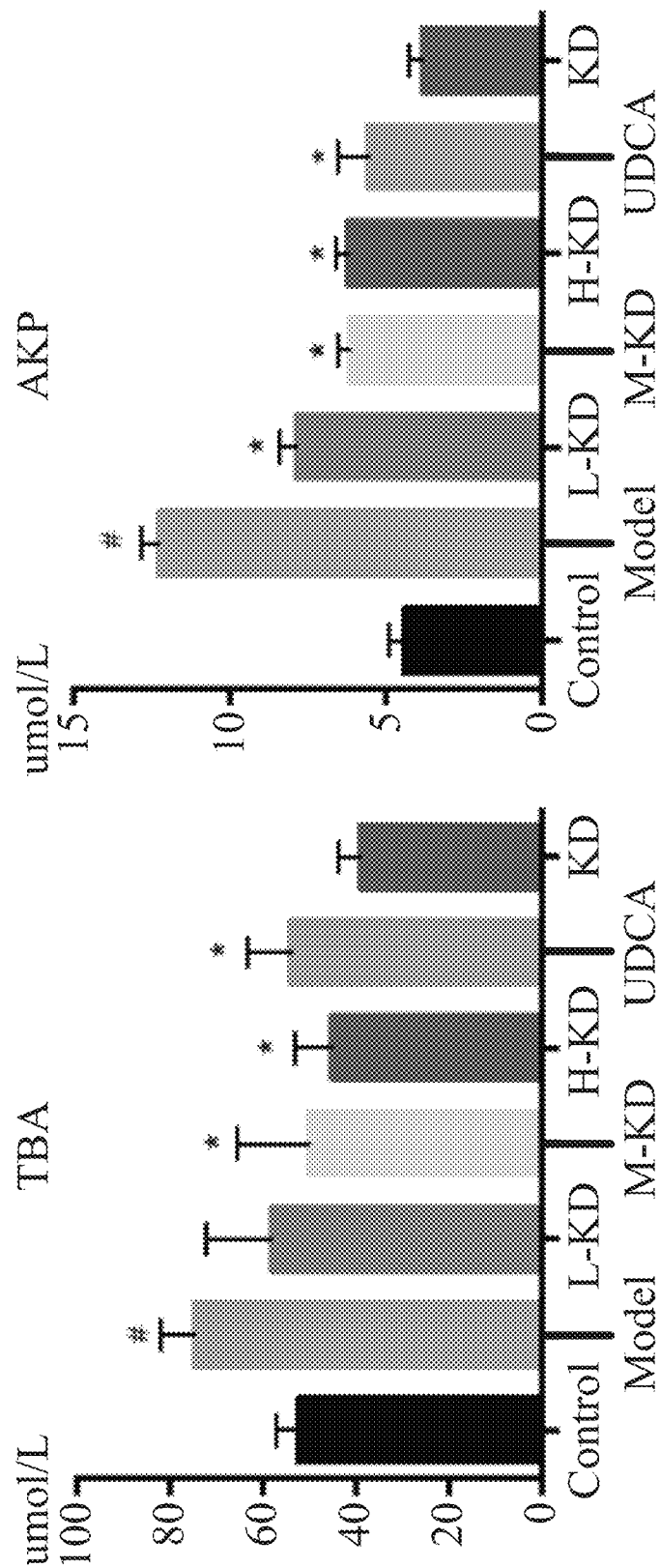
Figures 7E, 7F:
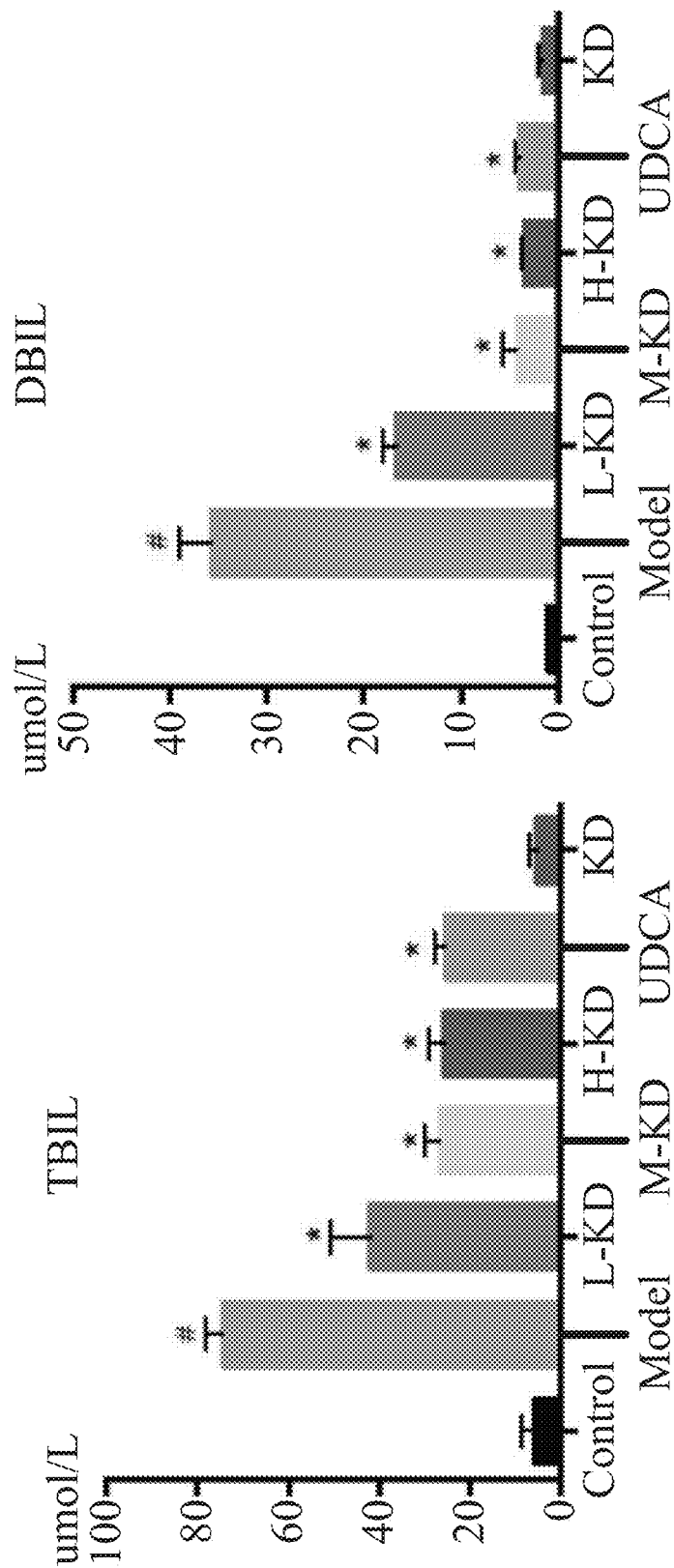

The effect of KD on the plasma biochemical indexes of ANIT induced cholestasis mice is shown in FIGS. 7A-7F. After 75 mg/kg ANIT was given to normal mice by a single gavage, the levels of ALT and AST in the plasma were increased by more than 5 times, indicating that ANIT caused liver cell damage, and ALT and AST in liver cells were released into the blood (FIGS. 7A-7B). At the same time, the significant increase of AKP in the plasma indicated that ANIT caused obstruction of bile duct, and AKP cannot enter the blood through the outflow of the bile duct (FIG. 7D). In addition, ANIT resulted in the increase of TBA, TBIL and DBIL in the plasma (FIGS. 7C, 7E, 7F). These results indicated that the modeling of intrahepatic cholestasis mice induced by ANIT was successful. On the other hand, after administration of different doses of KD or UDCA by gavage, the above-mentioned biochemical indexes in the plasma of cholestasis mice decreased significantly, and the above-mentioned biochemical indexes did not change after administration of 100 mg/kg KD to normal mice. Specifically, the intragastric administration of low, medium and high doses of KD and 80 mg/kg UDCA can significantly reduce ALT, AST, AKP, TBIL and DBIL in the plasma of mice with cholestasis, while intragastric administration of medium and high doses of KD and 80 mg/kg UDCA can significantly reduce TBA in the plasma of mice with cholestasis (FIG. 7C). The results show that KD can alleviate the liver injury of mice with intrahepatic cholestasis induced by ANIT.

To investigate the effect of KD on the liver pathophysiology of ANIT induced cholestasis mice, the liver samples collected in the animal experiment were stained with HE, as shown in FIGS. 8A-8G. In normal mice, the hepatocytes were clear, the hepatic sinusoid and hepatic cords were regular, and there was no congestion or inflammatory cell infiltration (FIG. 8A); in the ANIT model mice, the hepatic sinusoid expanded and there was obvious inflammatory cell infiltration (see the arrow mark in FIG. 8B); after the ANIT model mice were administered with different doses of KD, the expansion of hepatic sinusoid was improved and the infiltration of inflammatory cells was reduced, and the protective effect was dose-dependent (FIGS. 8C, 8D, 8E); the UDCA treatment group mice had normal hepatic sinusoid, obvious hepatocyte gap, and obvious recovery of inflammatory cell infiltration (FIG. 8F); the hepatocyte morphology of the normal mice administered with 100 mg/kg KD was not affected (FIG. 8G). The above results showed that ANIT could induce pathophysiological changes of the liver of normal mice, especially change the shape of hepatic sinusoid and the infiltration of inflammatory cells; KD could improve the pathophysiology of the liver of the cholestasis mice.

The effects of KD on the expression of Fxr, bile acid related transporters and metabolic enzymes in the ANIT induced intrahepatic cholestasis mice are shown in FIGS. 9A-9H.

Figures 9A, 9B:
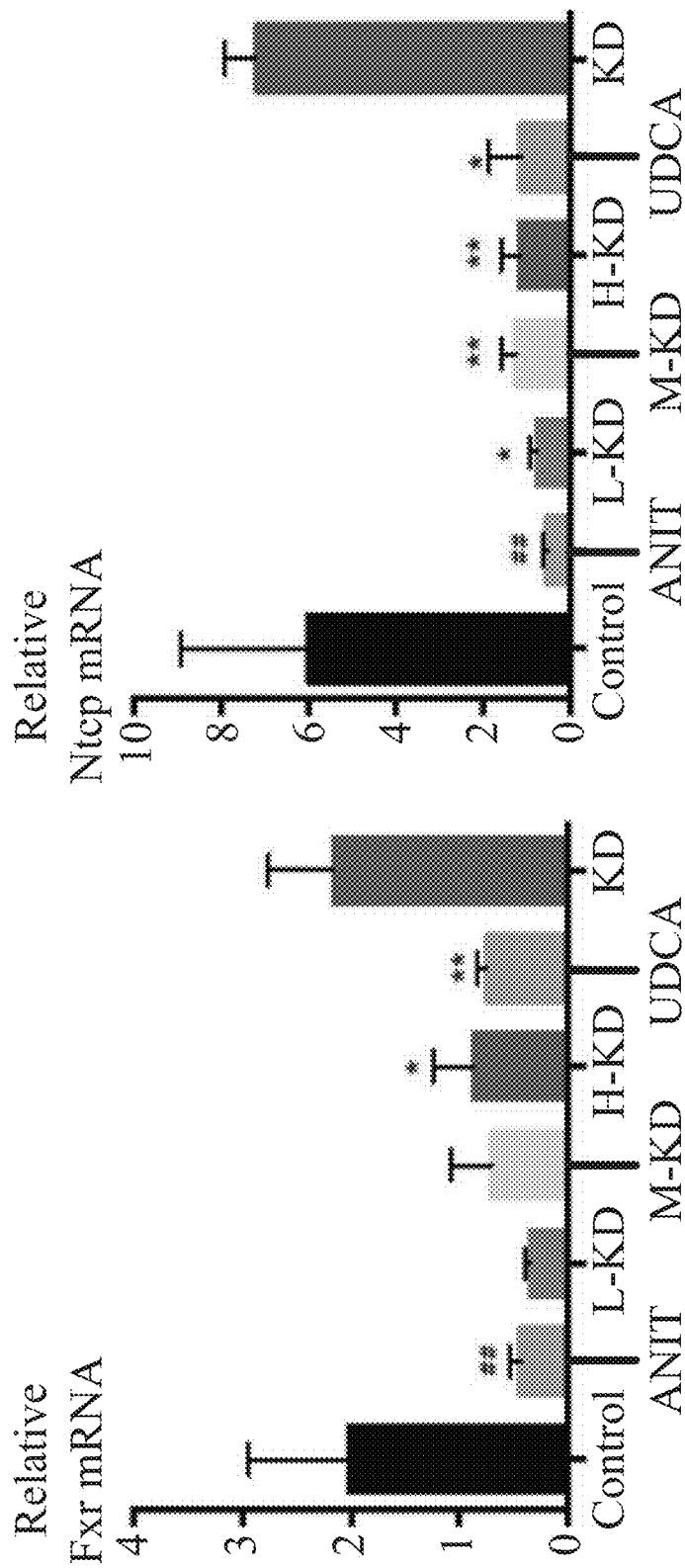
FIGS. 9A-9H show the effect of KD on mRNA expression of Fxr, bile acid-related transporter and metabolic enzyme gene in ANIT-induced intrahepatic cholestasis rats.
Figures 9C, 9D:
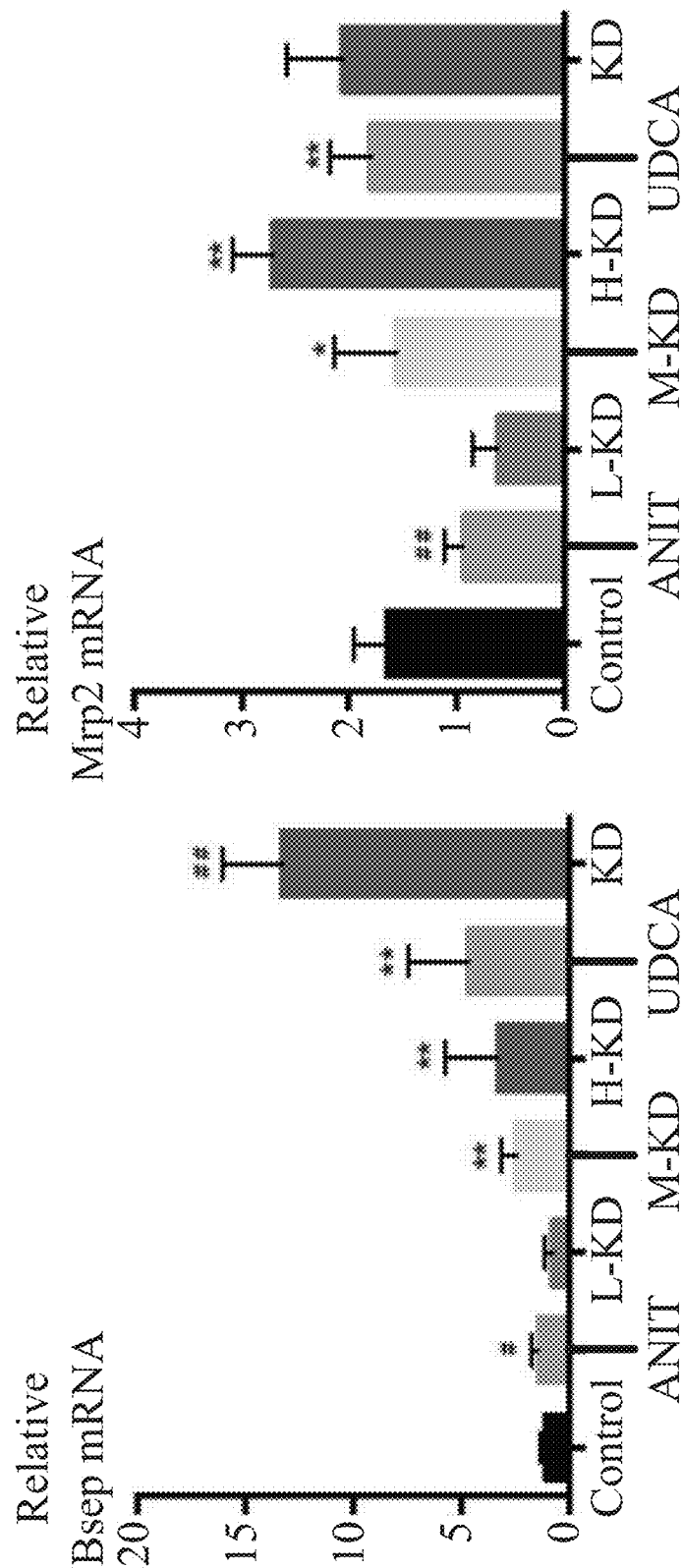
Figures 9E, 9F:
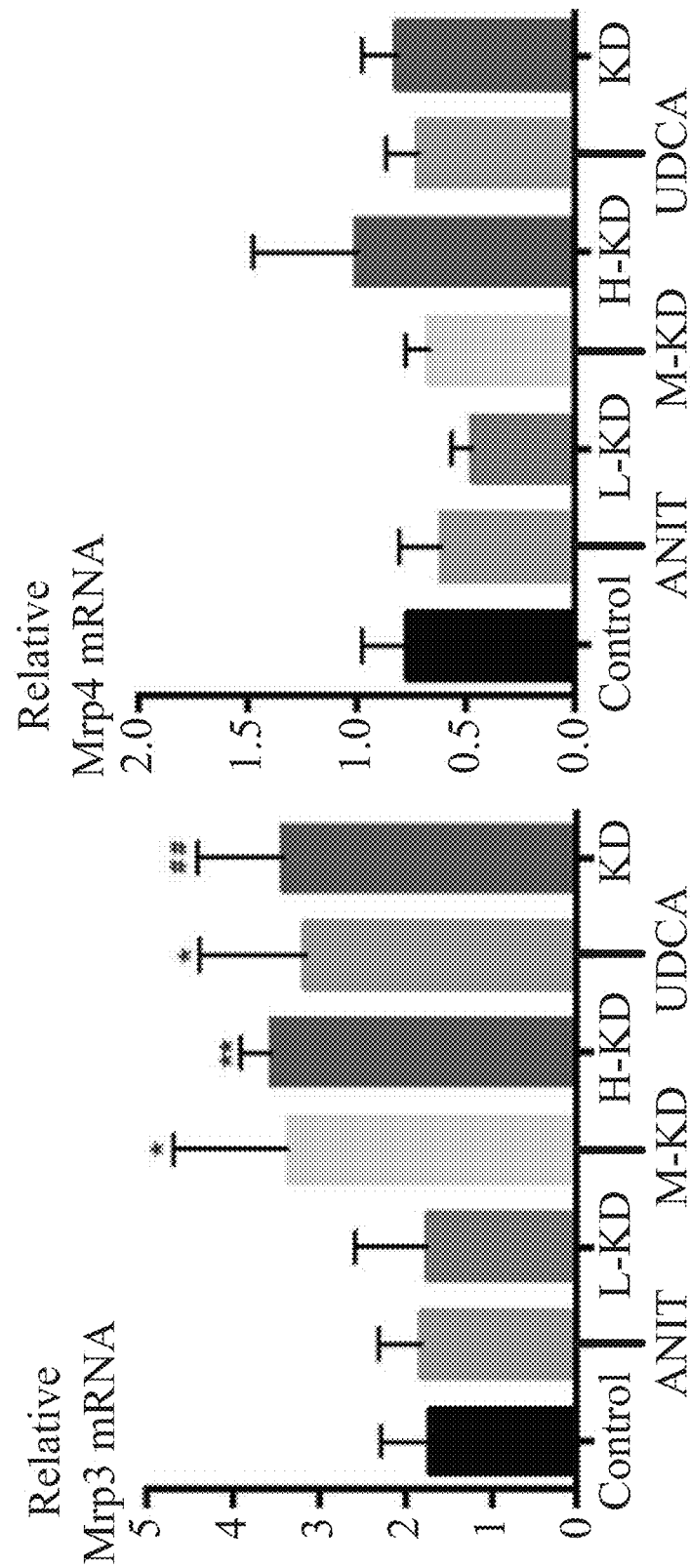
Figures 9G, 9H:
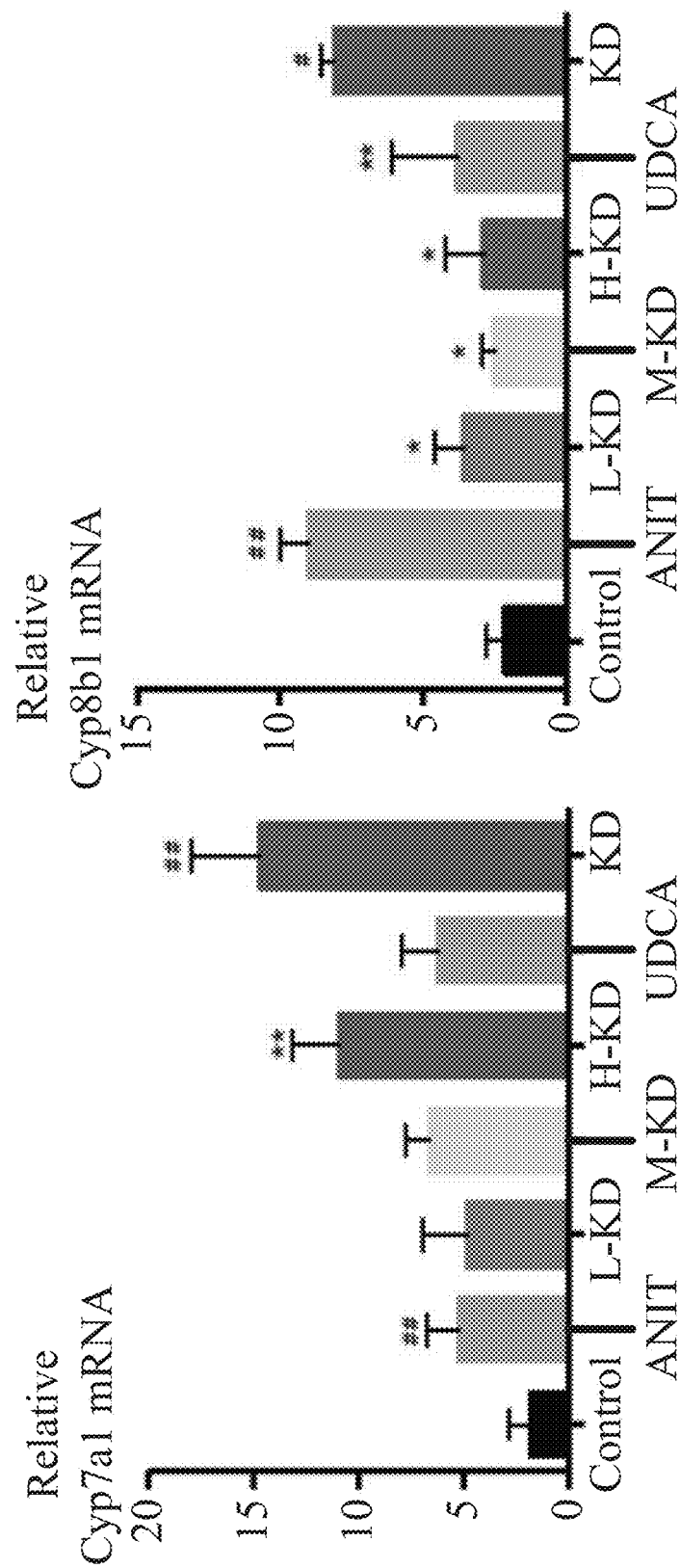
Figure 10A:
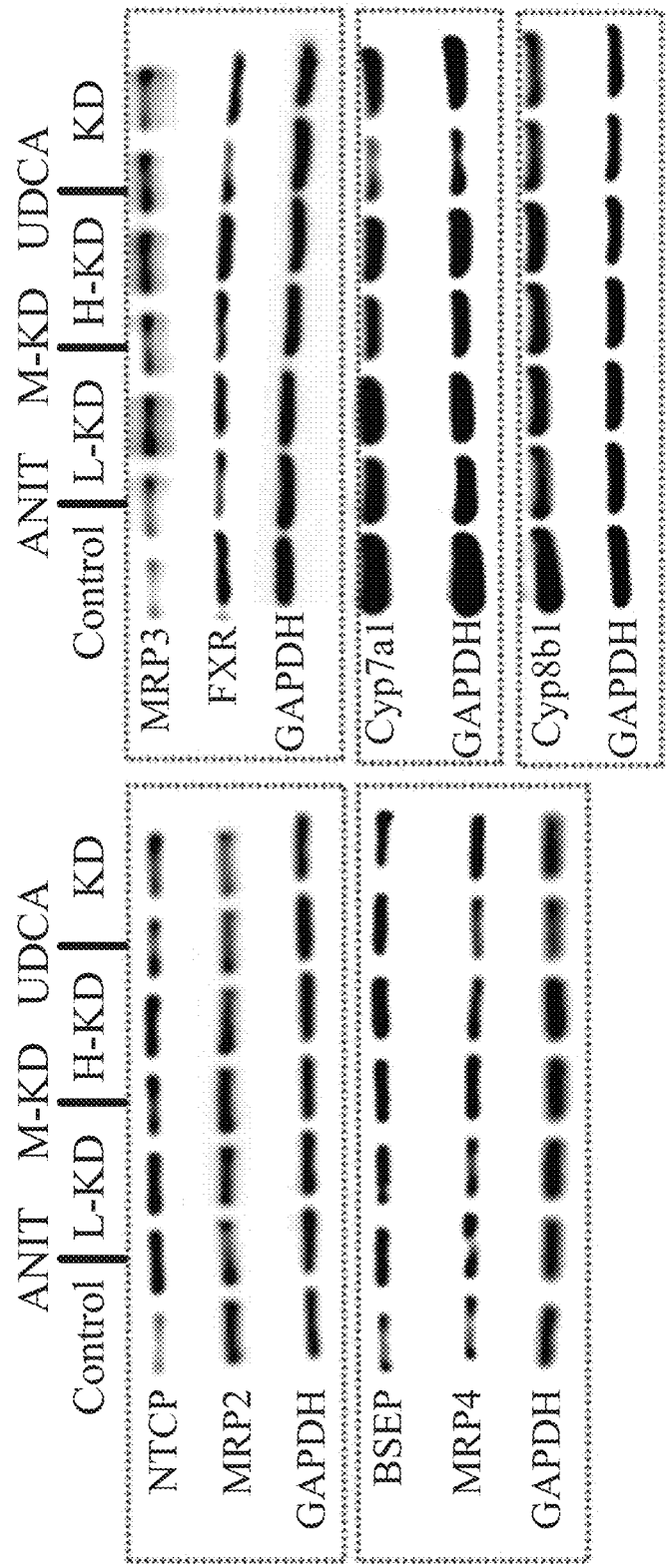
Figures 10D, 10E:
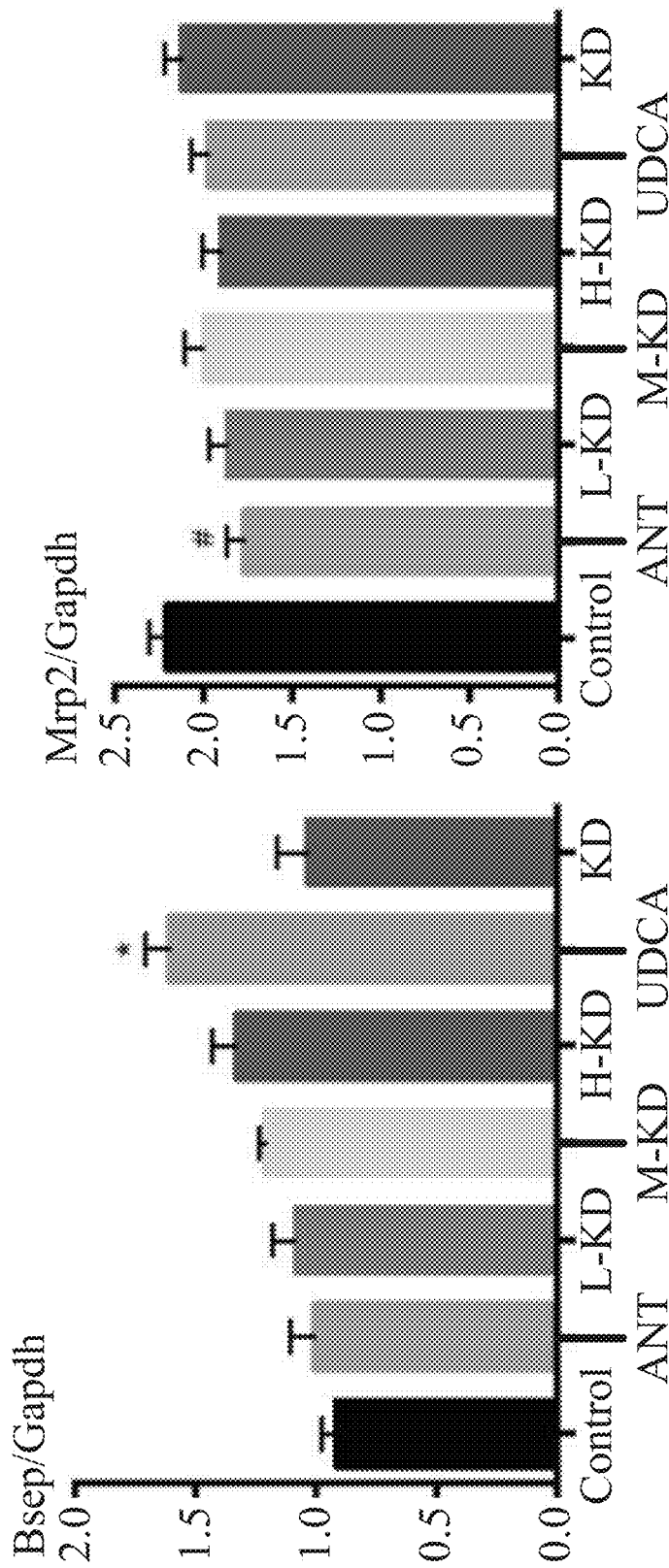
Figures 10F, 10G:
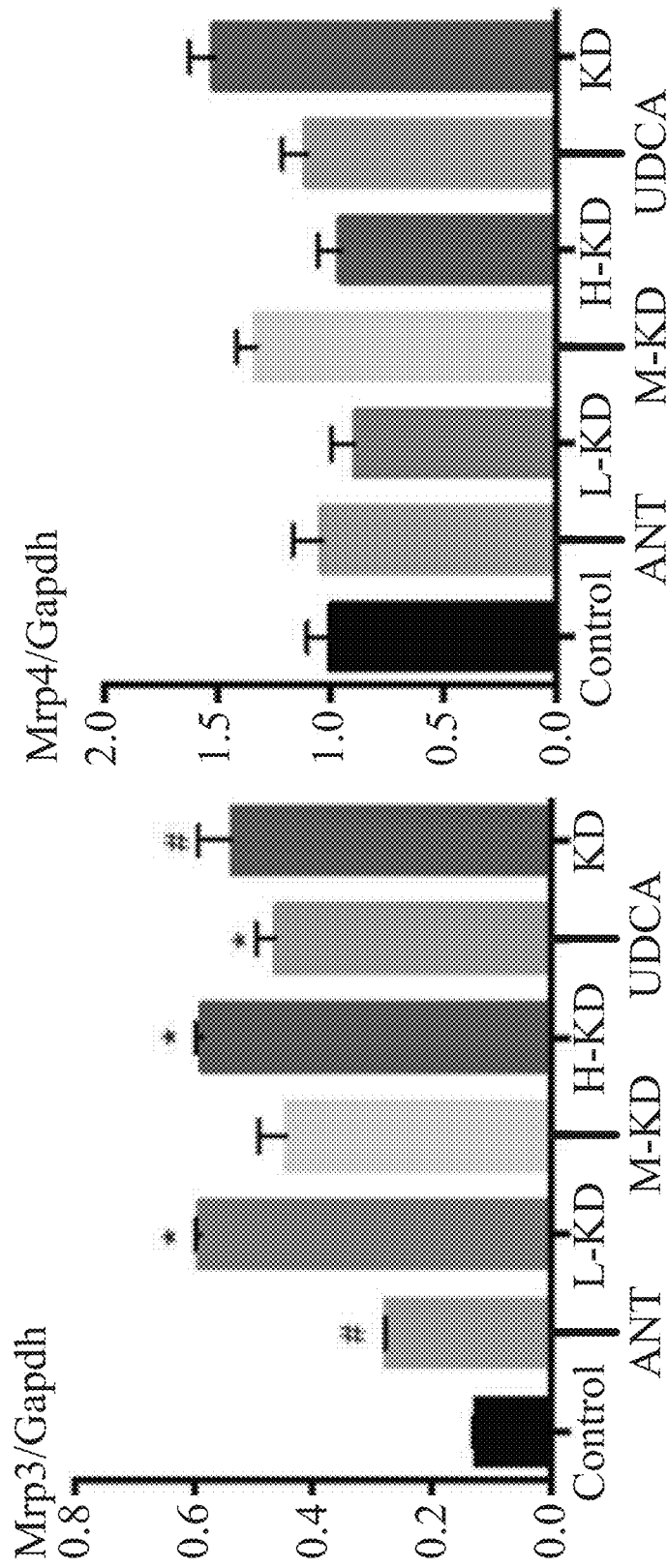
Figures 10H, 10I:
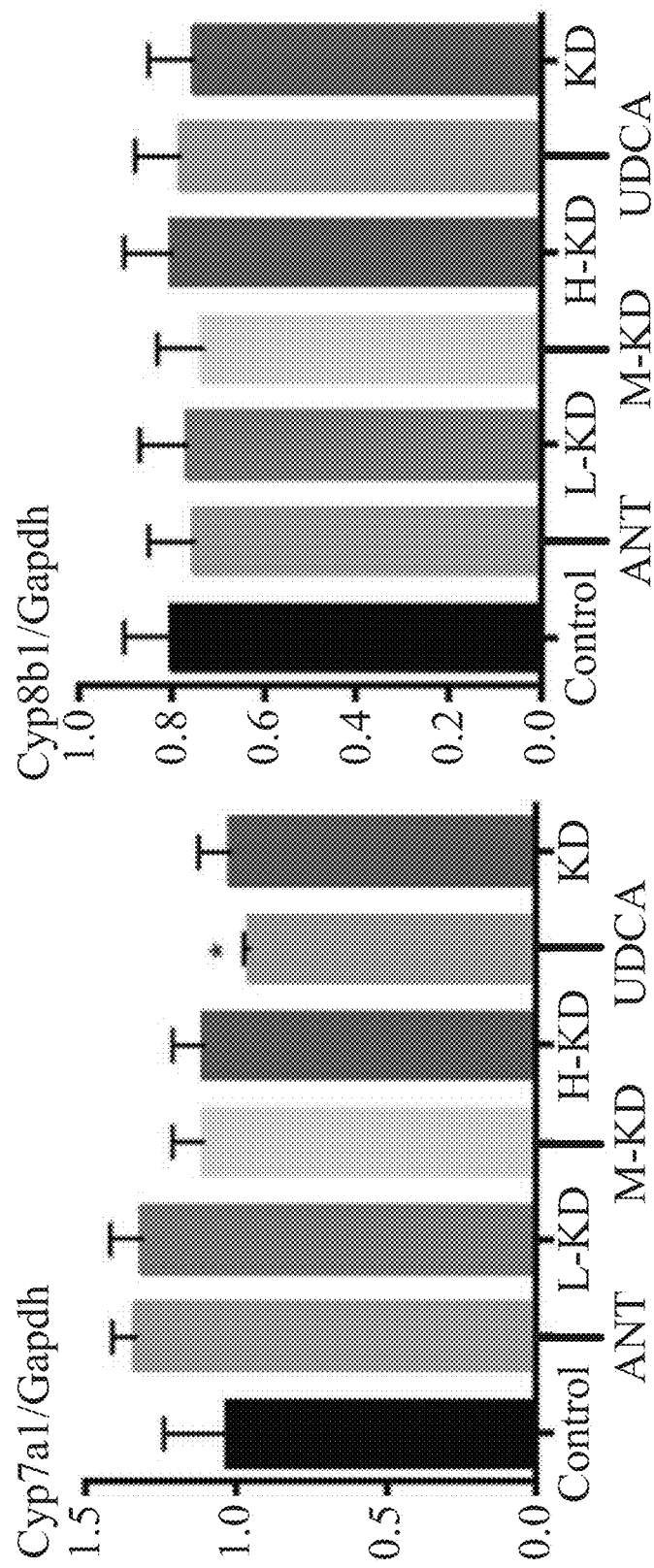

72 hours after administration of 75 mg/kg ANIT by gavage, the gene expression of Fxr, Ntcp and Mrp2 decreased significantly compared with that of normal mice (FIGS. 9A, 9B, 9D, 10B, 10E); the gene expression of Bsep, Cyp7a1 and Cyp8b1 increased significantly compared with that of normal mice (FIGS. 9C, 9G, 9H); while the gene expression of Mrp3 and Mrp4 did not change significantly compared with that of normal mice (FIGS. 9E, 9F, 10G). After administration of 100 mg/kg KD by gavage to normal mice, the gene expression of Fxr, Ntcp, Bsep, Mrp2 and Mrp4 had no significant change compared with that of normal mice (FIGS. 9A, 9B, 9D, 9F, 10B, 10D, 10E, 10G), but Mrp3, Cyp7a1 and Cyp8b1 were significantly higher than that of normal mice (FIGS. 9E, 9F, 9G, 10F). After continuous intragastric administration of low, medium and high doses of KD, the expression of Fxr, Ntcp, Bsep, Mrp2, Mrp3 and Cyp7a1 gene was up-regulated and Cyp8b1 gene was down regulated in the cholestasis mice (FIG. 9H). That is, high-dose KD can significantly up regulate the expression of Fxr and Cyp7a1 genes, and medium and high-dose KD can significantly up regulate the expression of Bsep, Mrp2 and Mrp3 genes (FIGS. 9A, 9B, 9C, 9D, 9E, 9G, 10B, 10D, 10F).

Conclusion: KD has a good therapeutic effect on ANIT-induced intrahepatic cholestasis liver injury and can effectively reduce liver injury. The mechanism lies in that the compound can regulate the expression of bile acid-related transporters and metabolic enzyme genes, thus reducing the liver damage caused by cholestasis.

EXAMPLE 4

Treatment of Alcoholic Fatty Liver using Kinsenoside

C57BL/6J mice aged 7-8 weeks were raised in the SPF experimental animal center of Tongji Medical College of Huazhong University of Science and Technology. They were provided with standard diet and drinking water. The room temperature was controlled at 23±2° C. After 7 days of adaptive feeding, they were given drugs by intragastric administration. The mice were divided into a control group, a model group, a high dose group (40 mg/kg KD), a medium dose group (20 mg/kg KD) and a low dose group (10 mg/kg KD). The mice were fed with a 5% alcoholic Lieber-DeCarli liquid diet and developed alcoholic fatty liver disease. The mice were administered with alcohol and drugs. Spherically, drinking water were administered to the control group and the model group, and different doses were administered to the dose groups. 5 weeks later (the first week was the adaptation period, and the alcohol concentration gradually increased from 0 to 5%), primary alcoholic fatty liver model was formed in the liver of the mice. Hematoxylin-eosin (H&E) staining results showed that there were a large number of fat vacuoles in the liver tissues of mice in the model group, while fat vacuoles were reduced in the high-dose group (40 mg/kg KD) and the medium-dose group (20 mg/kg KD), and KD could reduce the histopathological damage of liver (see FIG. 8A).

In the alcoholic fatty liver, liver function examination results indicated that the serum alanine aminotransferase (ALT) level in the model group was higher than that in the control group (see FIG. 11C), and the superoxide dismutase (SOD) activity in the liver was decreased after modeling.

Figure 11A:
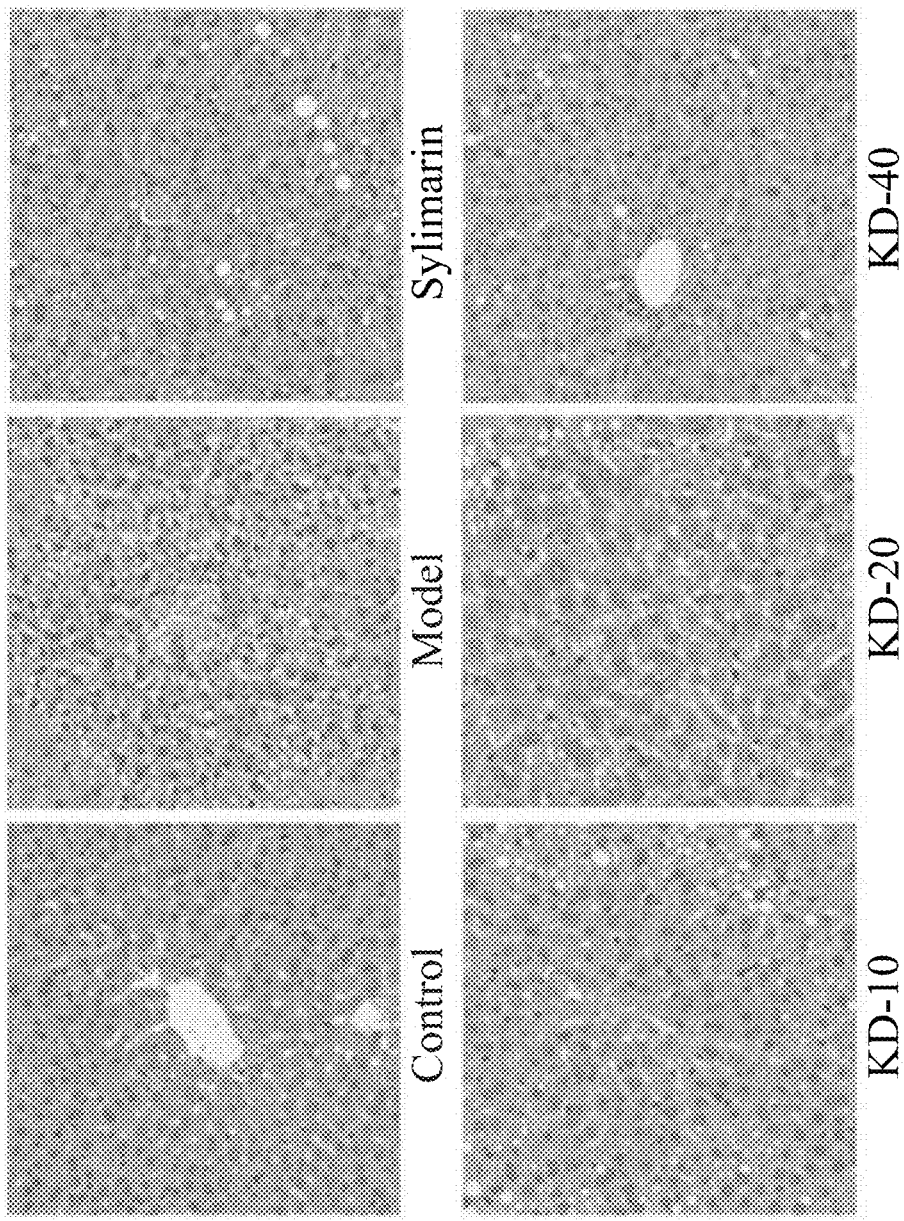
FIGS. 11A-11G show the protective effect of KD on alcoholic liver disease.
Figure 11B:
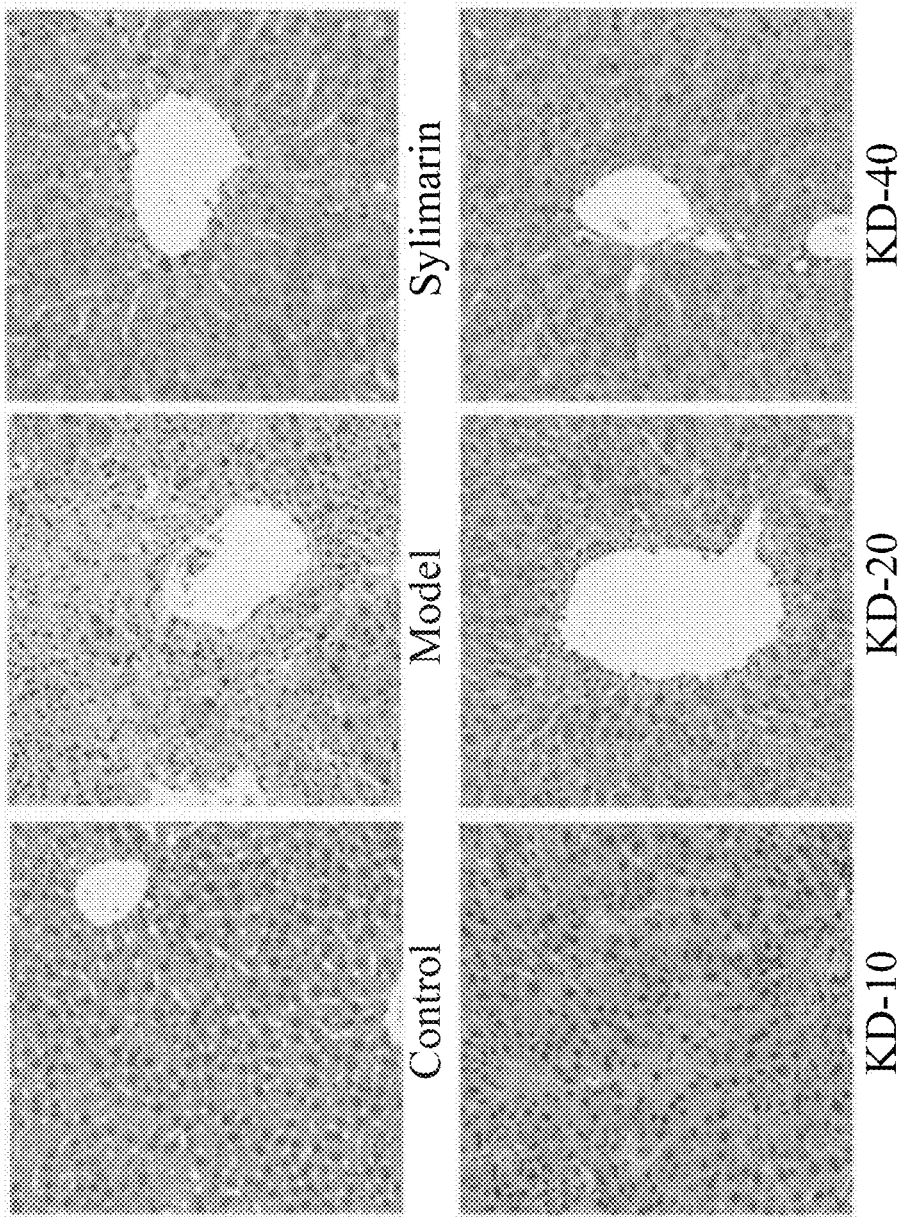
Figure 11C:
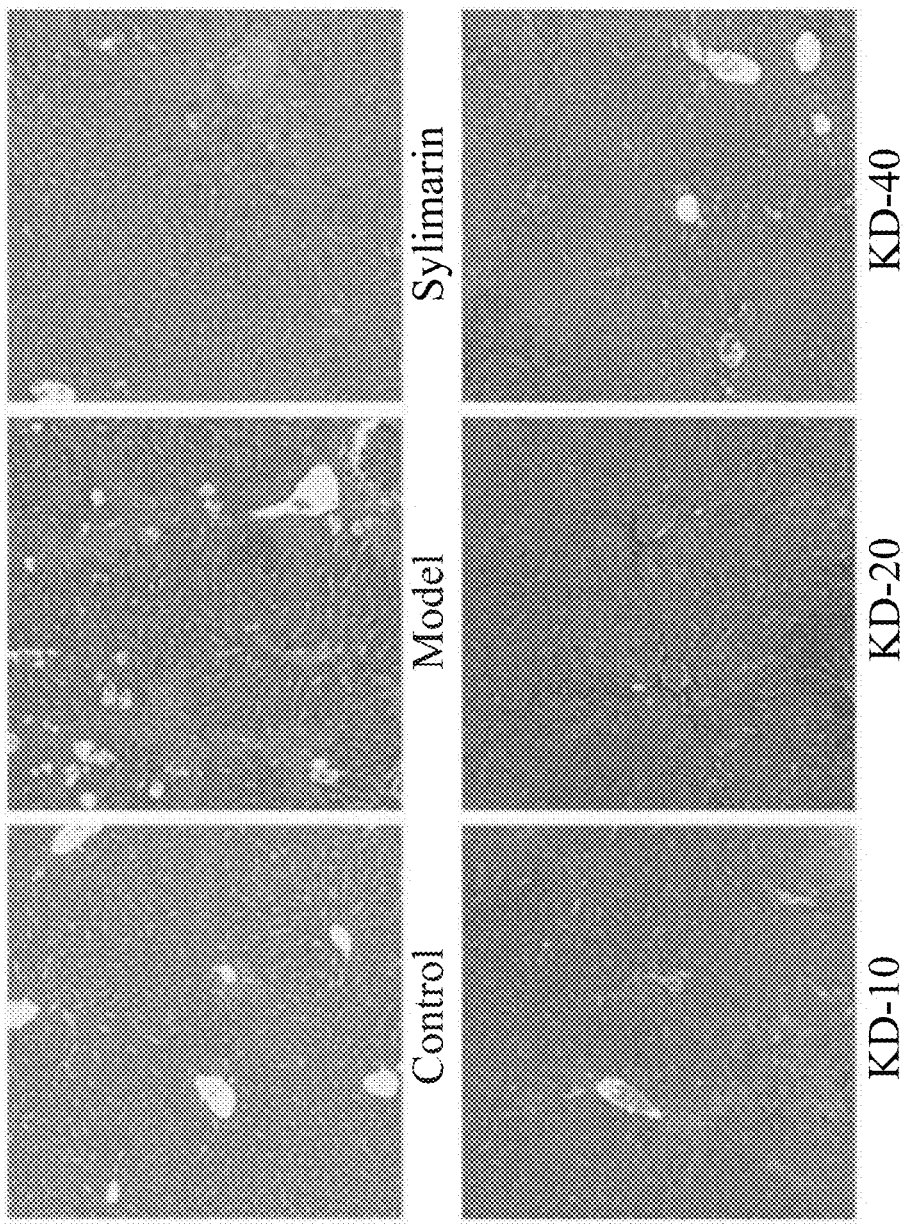
Figures 11D, 11E:
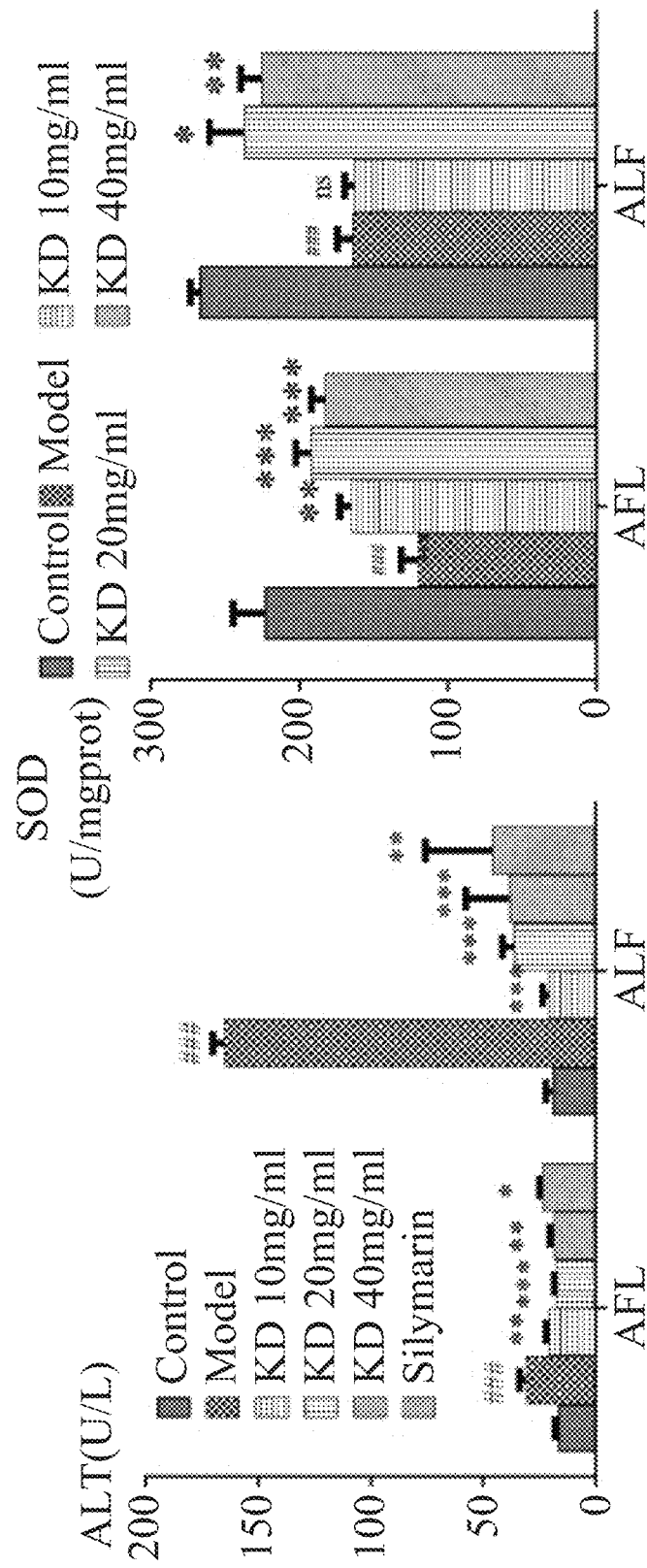

Therefore, the treatment with KD could reverse the oxidative stress injuries (see FIG. 11E).

Figures 11F, 11G:
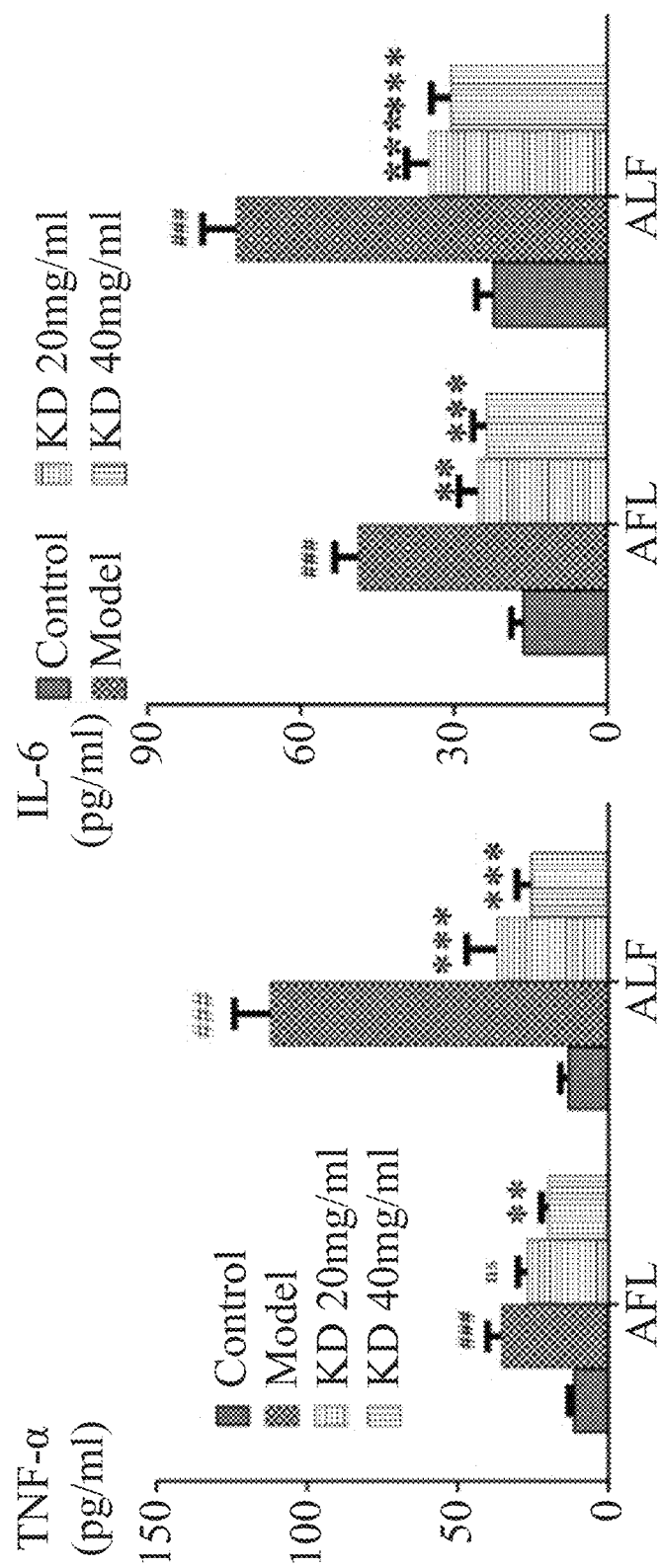

In addition, the treatment with KD reduced the secretion of the inflammatory cytokine TNF-α and IL-6 of the mice in the high and medium dose groups (see FIGS. 11F and 11G).

EXAMPLE 5

Treatment of Alcoholic Liver Fibrosis using Kinsenoside

C57BL/6J mice aged 8 weeks were raised in the SPF experimental animal center of Tongji Medical College of Huazhong University of Science and Technology. They were provided with standard diet and drinking water. The room temperature was controlled at 23±2° C. After 7 days of adaptive feeding, they were given drugs by intragastric administration. The mice were divided into a control group, a model group, a high dose group (40 mg/kg KD), a medium dose group (20 mg/kg KD) and a low dose group (10 mg/kg KD).

The mice were fed with a 5% alcoholic Lieber-DeCarli liquid diet and intraperitoneal injection of $CCl_4$ ($CCl_4$ was intraperitoneally injected twice a week for the last four weeks). The mice were developed alcoholic fatty liver disease. The mice were administered with alcohol and drugs. Spherically, drinking water were administered to the control group and the model group, and different doses were administered to the dose groups. 9 weeks later (the first week was the adaptation period, and the alcohol concentration gradually increased from 0 to 5%), primary alcoholic liver fibrosis model was formed in the liver of the mice. Hematoxylin-eosin (H&E) staining results showed that a large number of inflammatory cells infiltrated into the liver tissues of the mice in the model group, and Mallory bodies were observed. The inflammatory cells in the high-dose group (40 mg/kg KD) and the medium-dose group (20 mg/kg KD) were decreased compared with the model group, and the number of Mallory bodies was decreased, and KD could alleviate the histopathological damage of liver (see FIG. 11B). Masson staining results showed that the liver fibrosis in the model group was severe with bridging necrosis, and the fibrosis degree was reduced in the high-dose group (40 mg/kg KD) and the medium-dose group (20 mg/kg KD) (see FIG. 11C).

The liver function examination results of alcoholic liver fibrosis indicated that the serum alanine aminotransferase (ALT) level in the model group increased compared with the control group, and decreased after KD treatment (see FIG. 11D). The activity of superoxide dismutase (SOD) in the liver homogenate decreased in the model group, and KD treatment could reverse the oxidative stress injuries (see FIG. 11E).

In the alcoholic liver fibrosis experiments, the treatment with KD reduced the secretion of the inflammatory cytokine TNF-α and IL-6 of the mice in the high and medium dose groups (see FIGS. 11F and 11G).

Conclusion: KD has a good therapeutic effect on alcoholic fatty liver and alcoholic liver fibrosis, can effectively alleviate the development of alcoholic fatty liver and alcoholic liver fibrosis, produce activities in vivo such as reducing alcoholic fatty liver and alcoholic liver fibrosis, improving liver function and oxidative stress injury, reducing the secretion of inflammatory cytokines. KD can be used as a chemical drug for the treatment of alcoholic fatty liver and alcoholic liver fibrosis.

EXAMPLE 6

Treatment of Nonalcoholic Fatty Liver using Kinsenoside

Figure 12A:
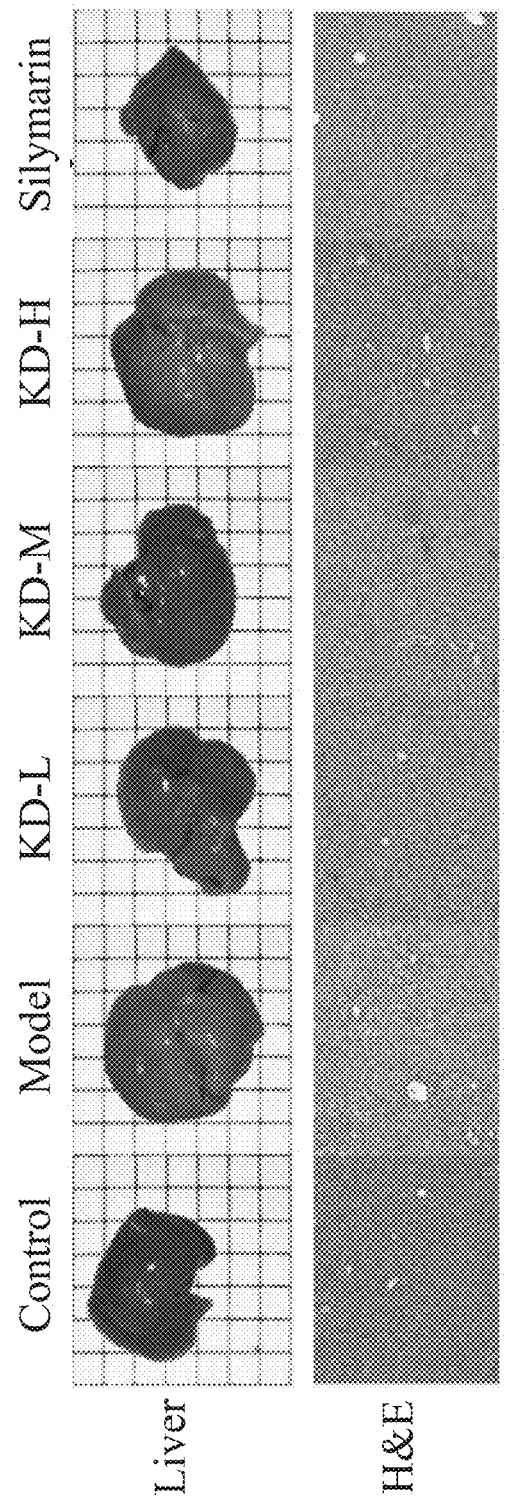
FIGS. 12A-12J show the protective effect of KD on nonalcoholic fatty liver induced by high fat and high sugar diet determined by hematoxylin eosin (H & E) staining and biochemical kit.
Figures 12B, 12C:
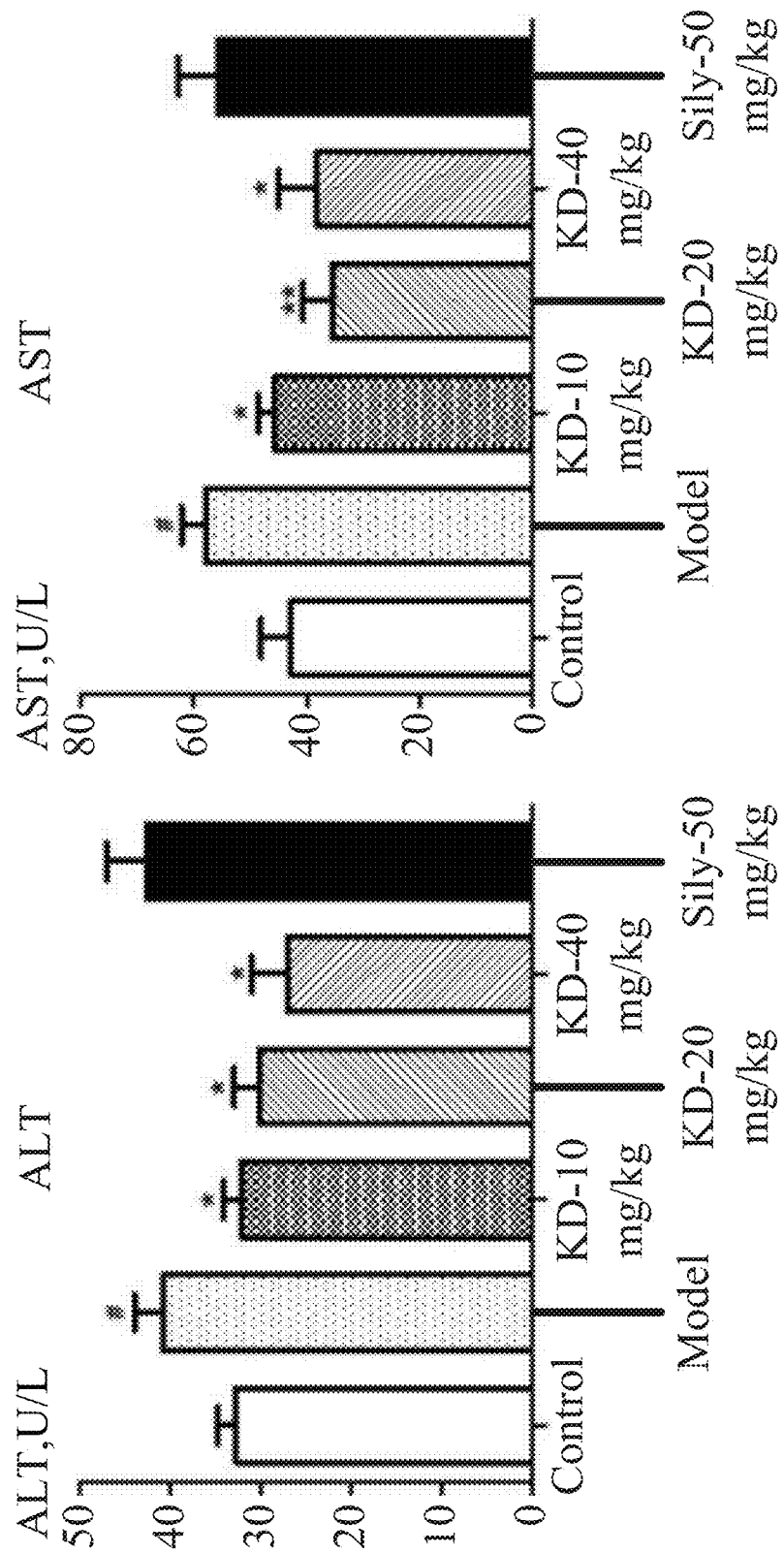

60 SPF male C57BL/6 mice aged 4 weeks were raised in the SPF experimental animal center of Tongji Medical College of Huazhong University of Science and Technology. They were provided with standard diet and drinking water. The room temperature was controlled at 23±2° C. After 7 days of adaptive feeding, the mice were randomly divided into a control group with normal diet and a high-fat and high fructose diet group (40% fat, 40% fructose, 20% protein, HFFD). The high-fat and high fructose diet group was fed with HFFD for 16 consecutive weeks, and in the $13^{th}$ week was randomly divided into a model group, a high dose group (40 mg/kg KD), a medium dose group (20 mg/kg KD), a low dose group (10 mg/kg KD) and a positive control group silymarin (50 mg/kg Sily). The mice were fed according to the groups, and the control group and the model group were fed with the same dose of normal saline for 4 weeks. The photos of liver and the results of hematoxylin eosin (H&E) staining showed that KD could significantly reduce the lipid degeneration and inhibit the size and number of lipid droplets in the high, middle and low dose groups (see FIG. 12A). The results of liver function examination showed that the levels of ALT, AST and γ-GT in the model group were significantly higher than those in the control group, and they were significantly reduced after KD treatment (see FIGS. 12B-12D), and the therapeutic effect was better than that of silymarin. The development of nonalcoholic fatty liver disease is closely related to the lipid levels of the liver and serum.

Figures 12D, 12E:
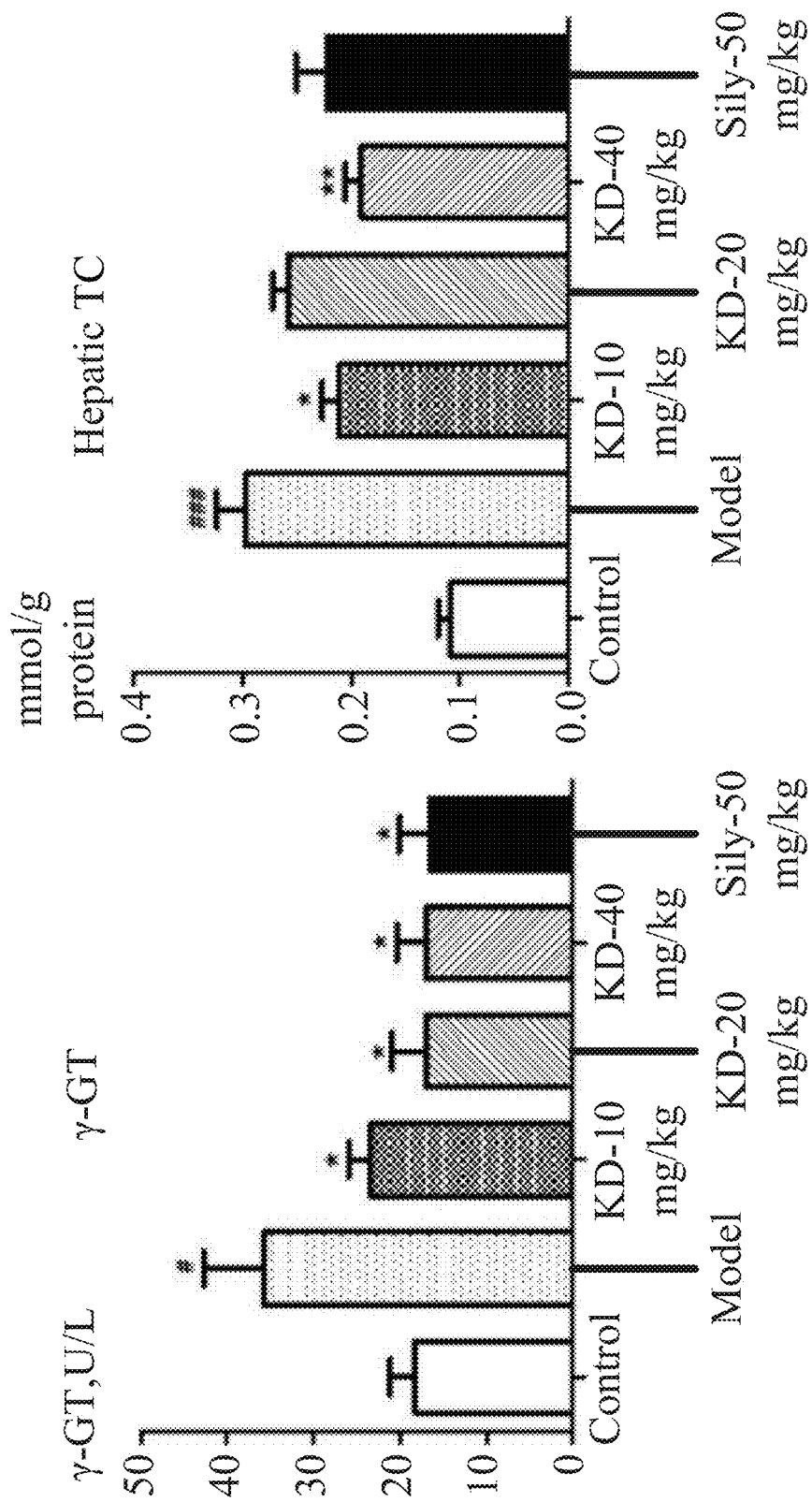
Figures 12F, 12G:
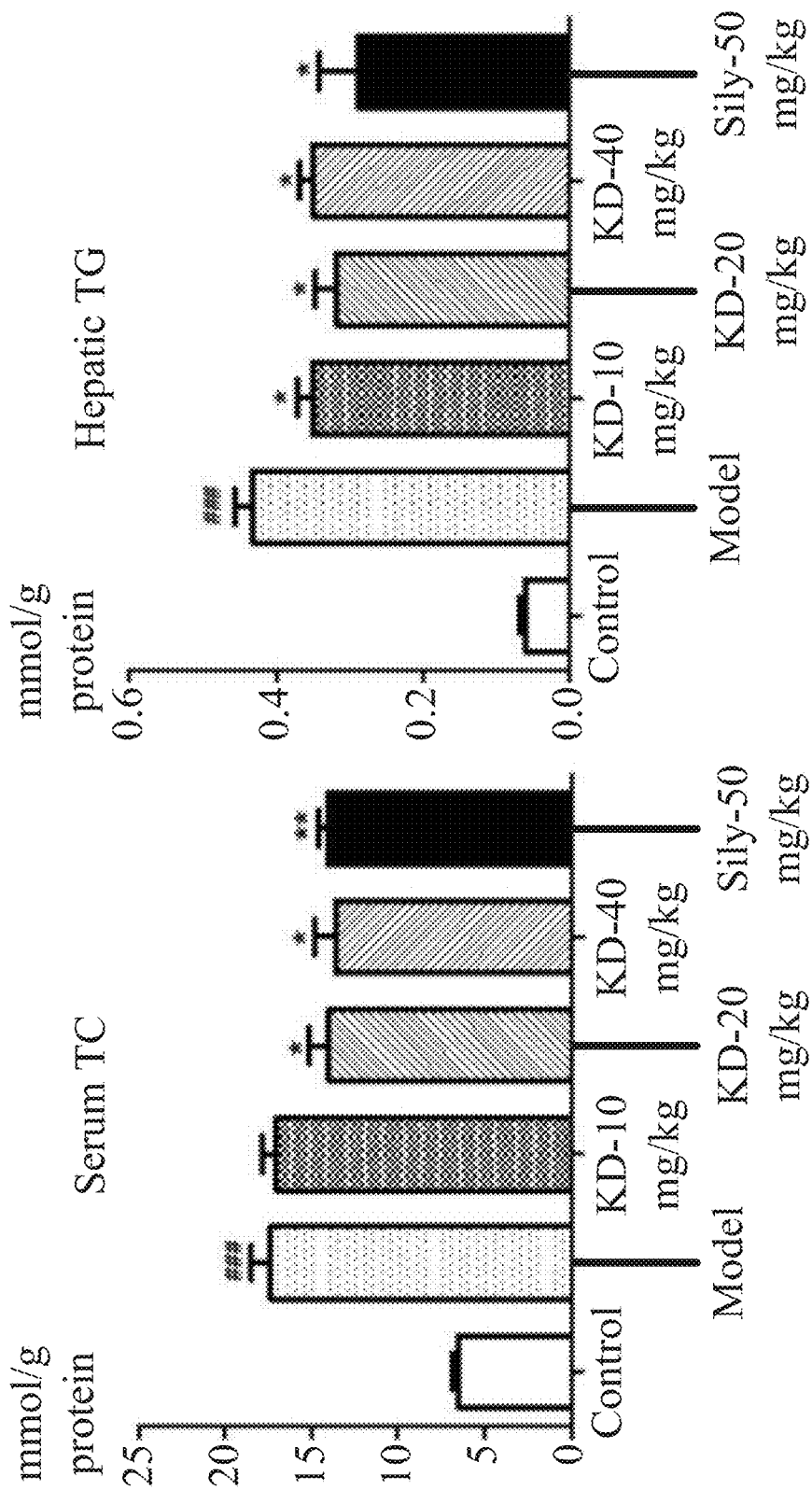
Figures 12H, 12I:
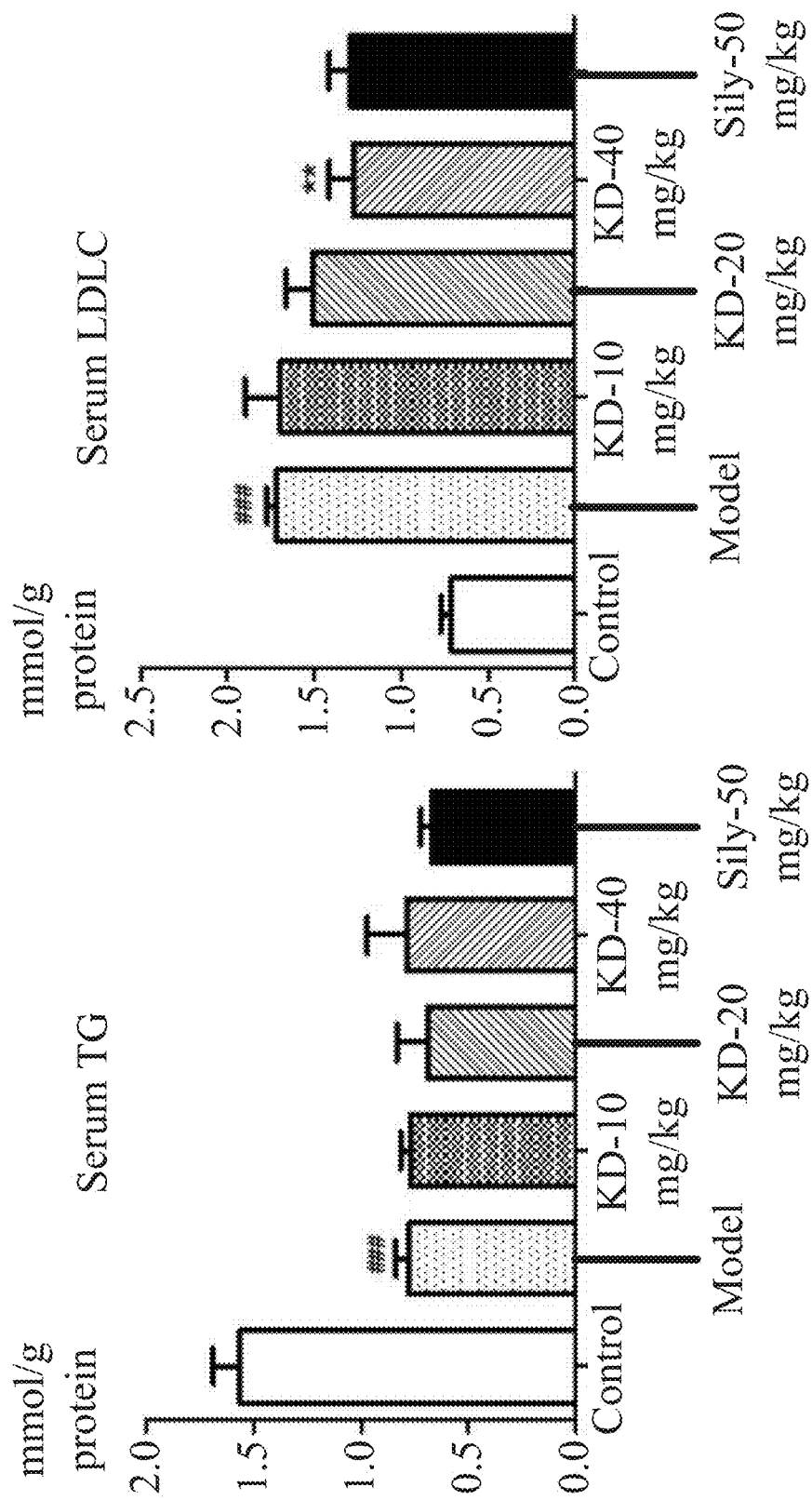
Figure 12J:
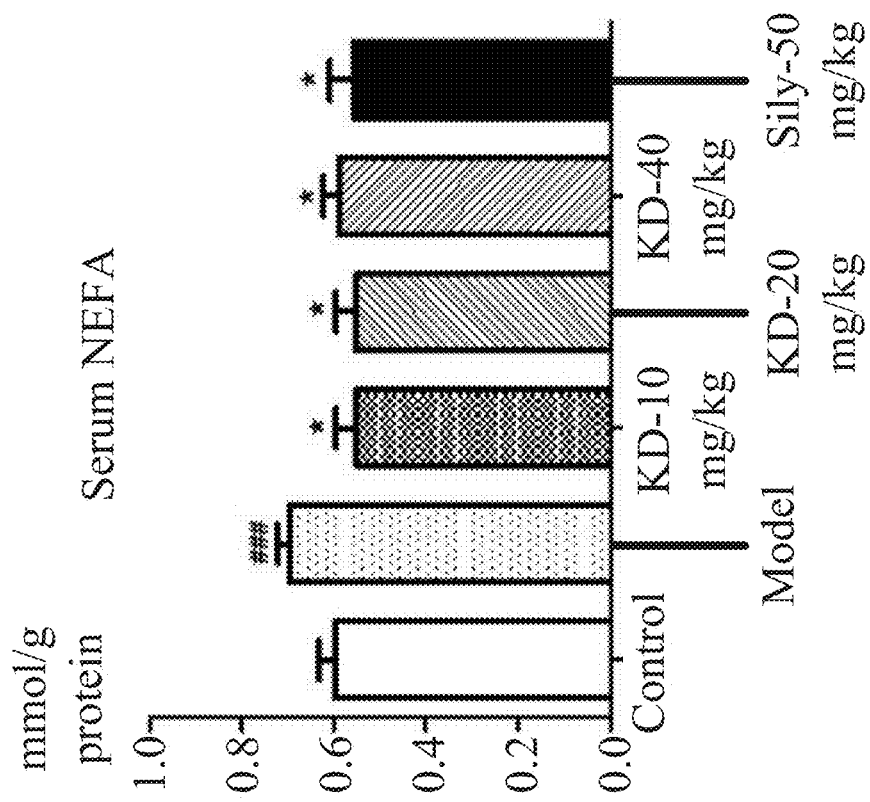

The level of total cholesterol in liver and serum of the mice induced by high-fat and high-sugar diet was significantly increased, while the level of total cholesterol in liver and serum was significantly reduced after the treatment with low, medium and high doses of KD (see FIGS. 12E-12F). Lipid accumulation in the liver is an important feature of nonalcoholic fatty liver. The results showed that the serum triglyceride level of the mice decreased and the liver triglyceride level increased significantly after the induction of high-fat and high sugar diet (see FIGS. 12G-12H), suggesting that the liver had obvious lipid accumulation. However, each dose of KD could significantly inhibit the level of triglyceride in the liver (see FIGS. 12G-12H), improve the abnormal lipid accumulation in the liver and improve the nonalcoholic fatty liver. In addition, it was found that low-dose KD treatment could significantly inhibit the serum LDL level in the mice (see FIG. 12I), and the KD treatment could significantly inhibit the free fatty acid level in the serum (see FIG. 12J). The above results showed that KD could significantly improve the liver function, inhibit abnormal lipid accumulation in the liver, and improve the nonalcoholic fatty liver, and the effect of KD was significantly better than that of silymarin, and the therapeutic dose of the KD was lower.

Figures 13A, 13B:
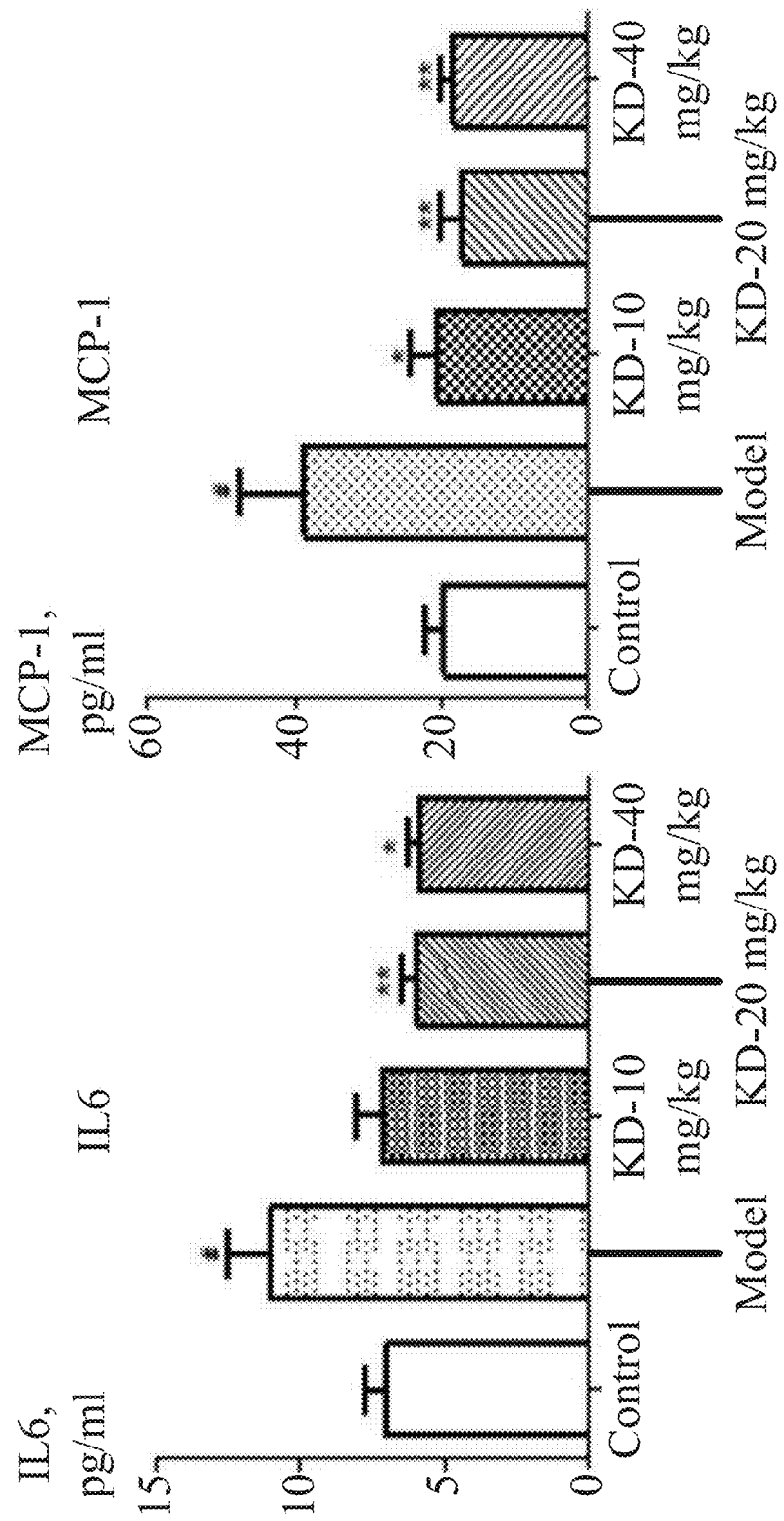
FIGS. 13A-13H show the secretion level of serum inflammatory cytokines and the expression level of polarized marker molecules in liver macrophages detected by flow cytometry kit and real-time fluorescent quantitative PCR.
Figures 13C, 13D:
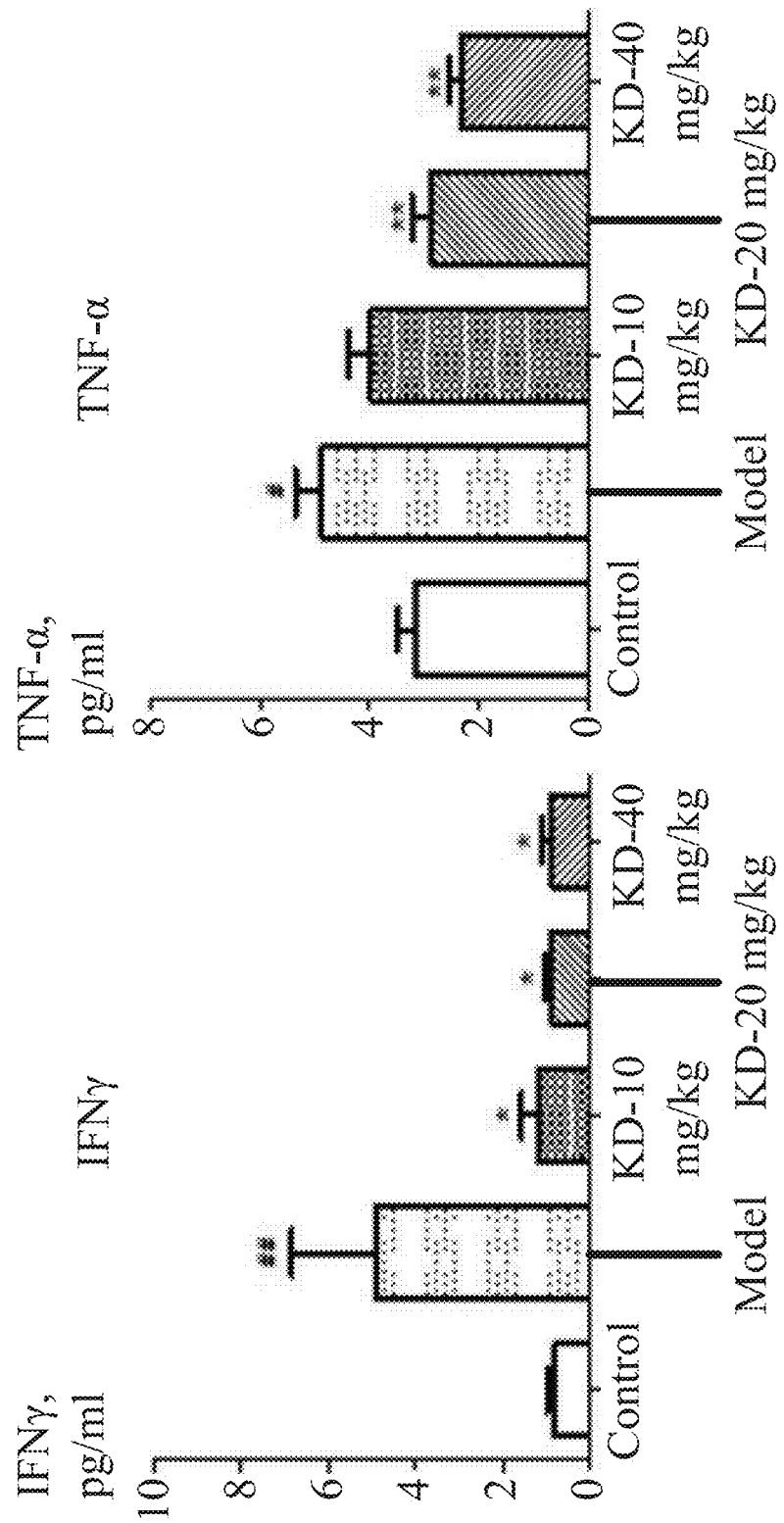
Figures 13E, 13F:
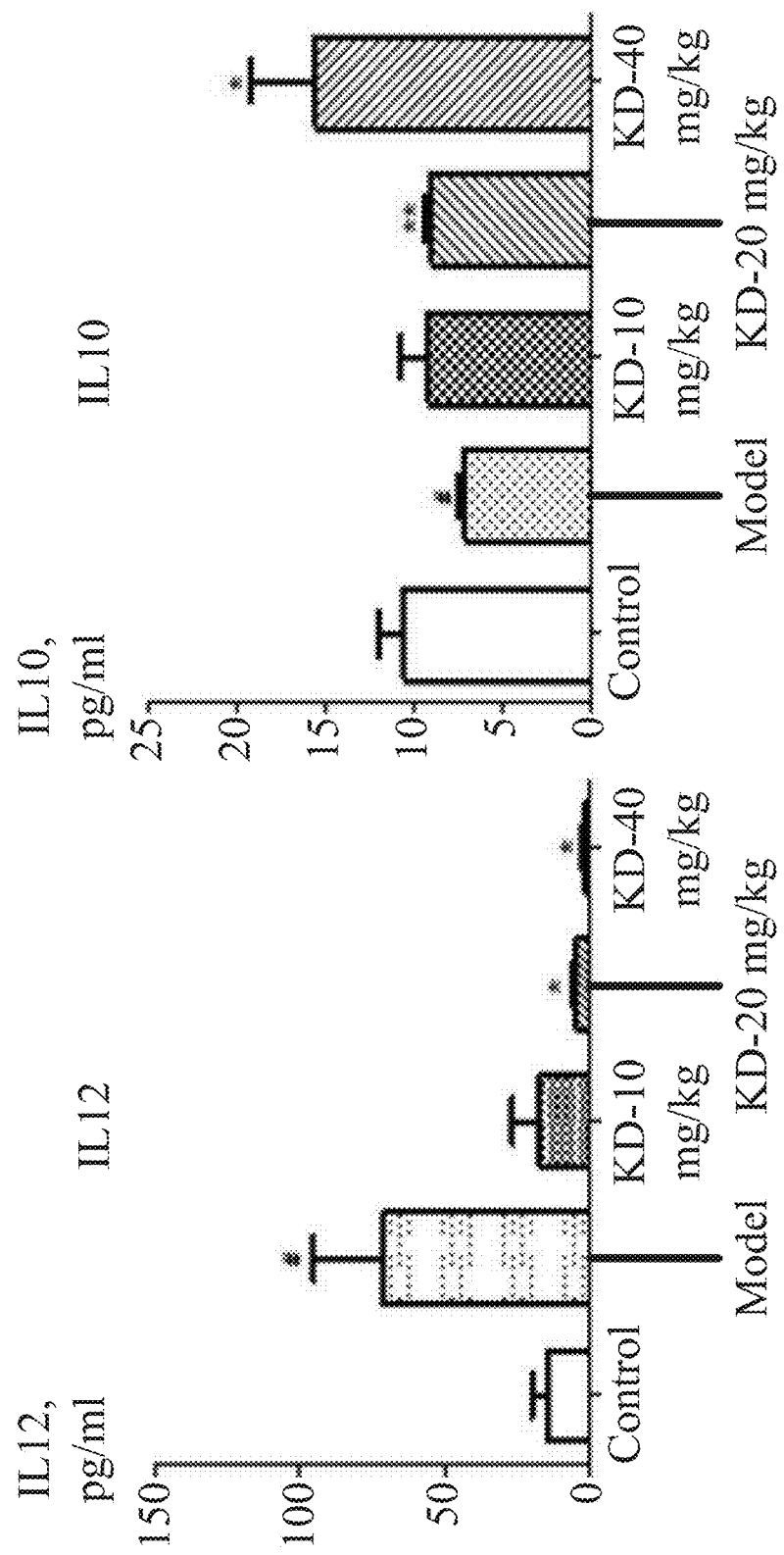

Steatosis and steatohepatitis are considered to be prominent manifestations of NAFLD. In the model of nonalcoholic fatty liver induced by high fat and high sugar diet, the treatment of low, medium and high dose of KD can significantly inhibit the secretion of proinflammatory cytokines IL-6, MCP-1, IFN-γ, TNF-α and IL-2 (see FIGS. 13A-13E), and increase the secretion of anti-inflammatory cytokine IL-10 (see FIG. 13F).

Figure 13G:
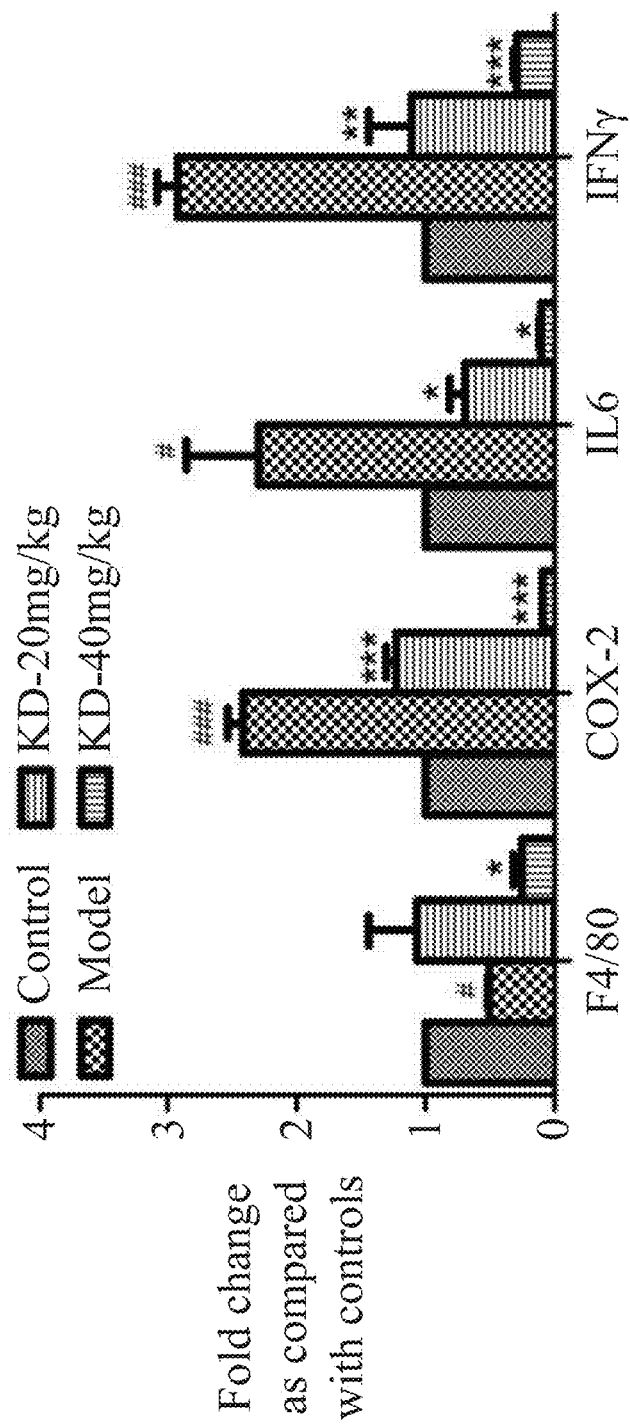
Figure 13H:
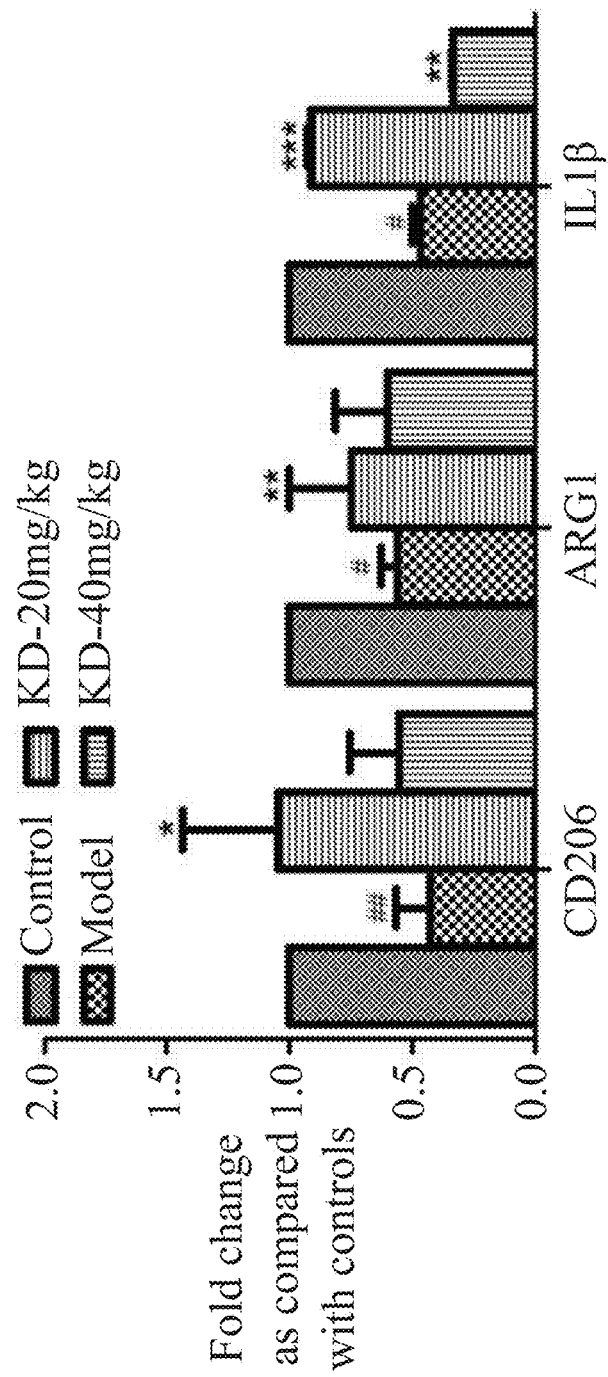

Liver macrophages (Kuffer cells) are the key regulatory cells of natural immune and adaptive immune networks in the liver. The polarization of macrophages is closely related to liver inflammation and lipid accumulation in the development of nonalcoholic fatty liver. The pro-inflammatory Th1 response plays an important role in the systemic mild inflammatory response related to nonalcoholic fatty liver, which promotes the activation of the M1 Kuffer cells, while the M2 Kuffer cells can inhibit the development of nonalcoholic fatty liver. It was found that high dose KD could inhibit the expression level of the total macrophage marker molecule F4/80, while the medium and high dose KD could significantly inhibit the expression level of inflammatory molecule COX-2 and the inflammatory M1-type macrophage molecules IL6 and IFN (see FIG. 13G), and promote the expression of anti-inflammatory M2-type macrophage marker molecules CD206, ARG1 and IL1β (FIG. 13H).

Conclusion: KD has a good therapeutic effect on nonalcoholic fatty liver, and can effectively reduce lipid accumulation and liver damage in the liver. The mechanism lies in that the compound can reduce the lipid levels in the liver and serum, improve liver function, reduce the secretion of inflammatory cytokines, and promote THE polarization of M2-type macrophages and the like.

EXAMPLE 7

Treatment of Nonalcoholic Steatohepatitis using Kinsenoside

150 SPF male mice C57 aged 6-8 weeks were raised in the SPF experimental animal center of Tongji Medical College of Huazhong University of Science and Technology. They were provided with standard diet and drinking water. The room temperature was controlled at 23±2° C. After 7 days of adaptive feeding, they were given drugs by intragastric administration. The mice were randomly divided into a control group, a model group, a low-dose group (40 mg/kg KD), a medium-dose group (20 mg/kg KD), a high-dose group (10 mg/kg KD), a positive silymarin group (100 mg/kg) and a positive Fuzheng Huayu Capsule group (1.5 g/kg). The control groups were administered with normal diet. The model group and each administration group were fed with methionine choline deficiency (MCD) feed. Each group was administrated by gavage. The control group and the model group were given equal amount of thrice steamed water once a day for 8 weeks. The mice were weighed every three days. The hair color, state, food, water and defecation of each group were observed, and the death of each group was recorded. At the end of the 2nd week, $4^{th}$ week and $6^{th}$ week, three mice were randomly selected and killed to observe the modeling state. At the end of the 8th week, after the last administration, all mice were provided with no food but water for 12 hours, and all indexes were measured.

Figure 14A:
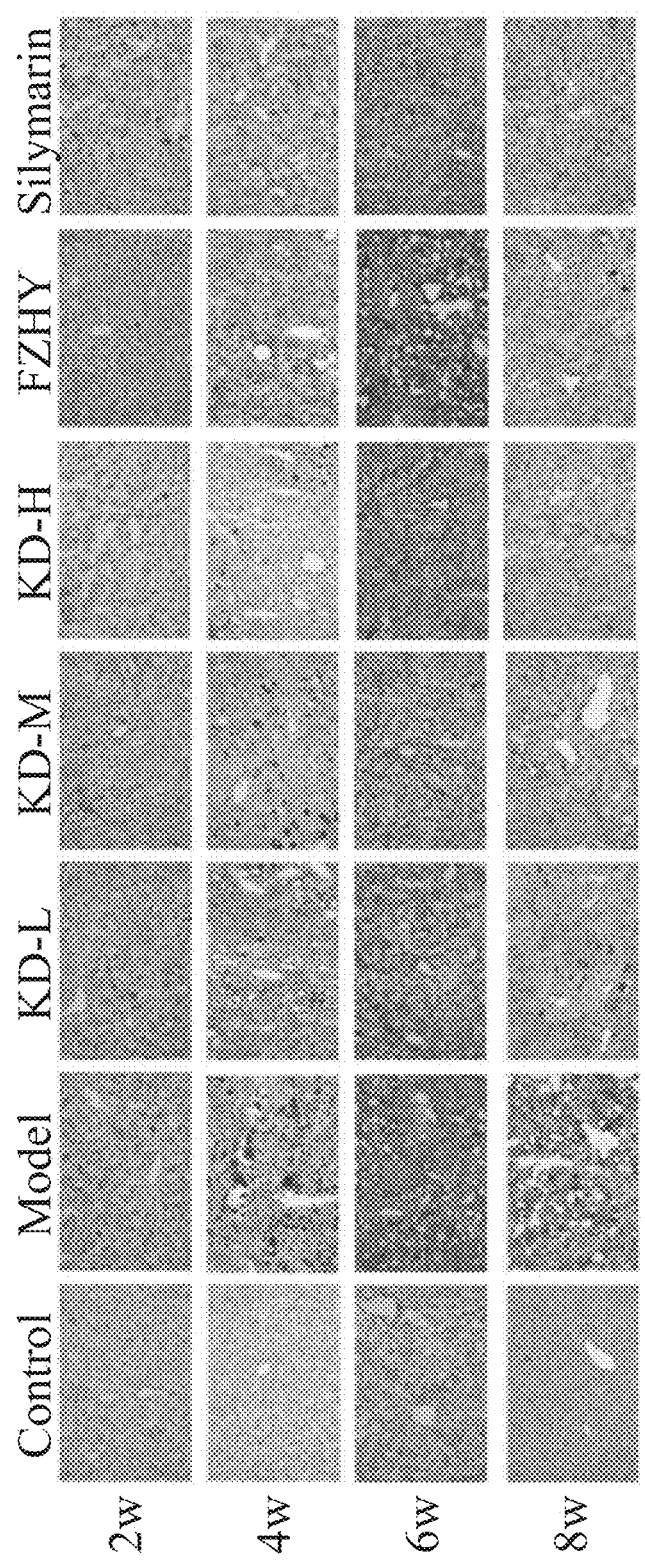
FIGS. 14A-14I show oil red O staining, Image J software and serum biochemical kit (AST, ALT, TG, TC) were used to study the protective effect of KD on hepatic steatosis in NASH mice.
Figures 14B, 14C:
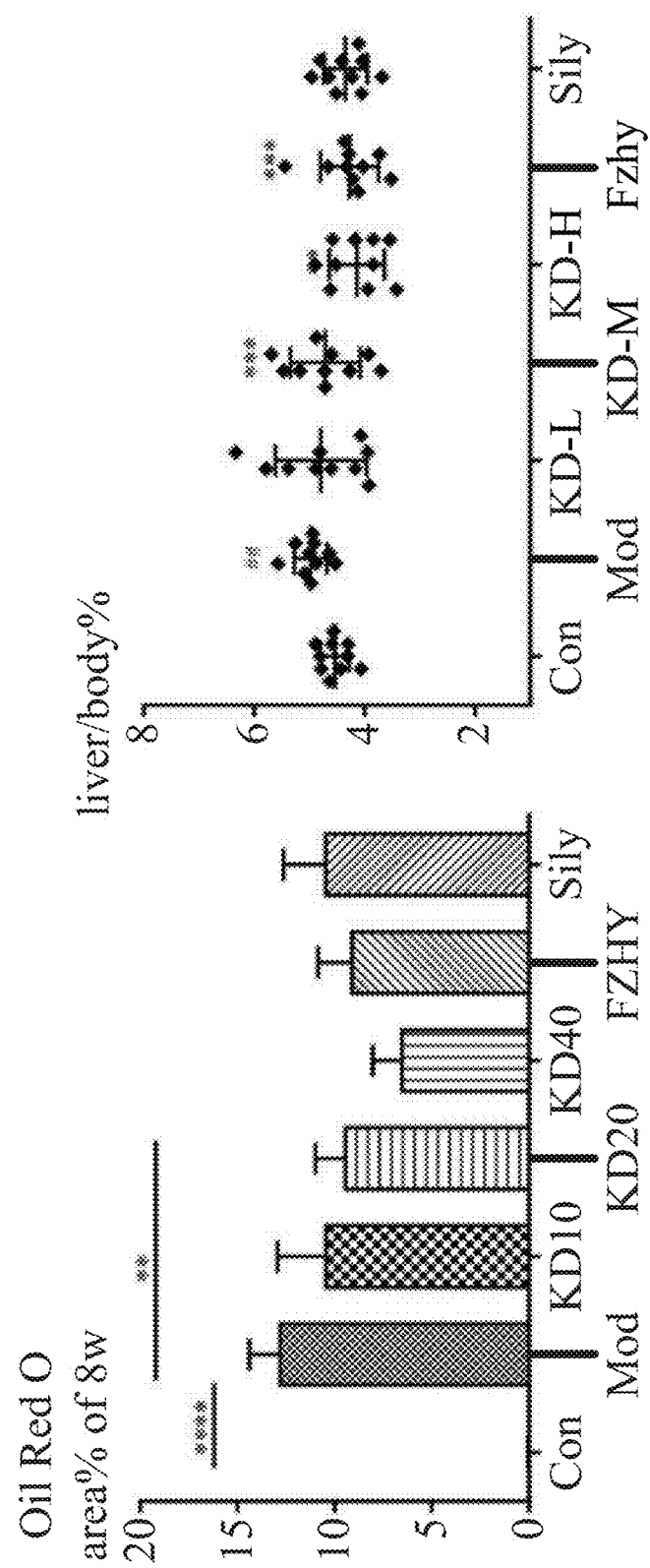
Figures 14D, 14E:
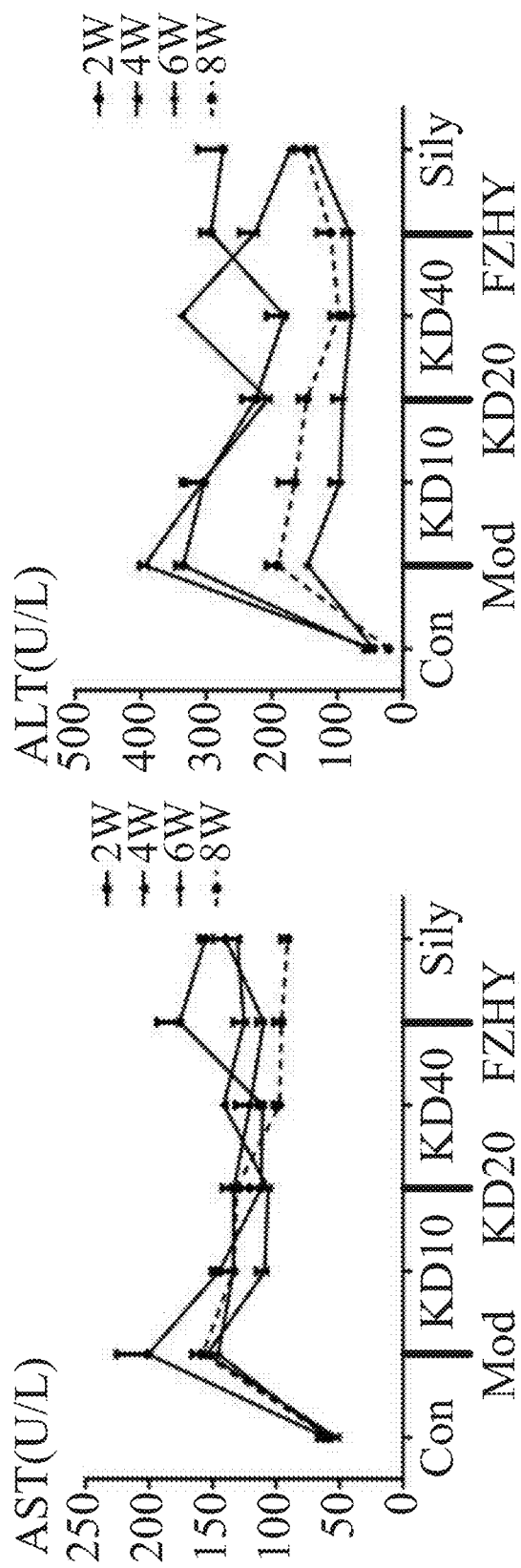
Figures 14F, 14G:
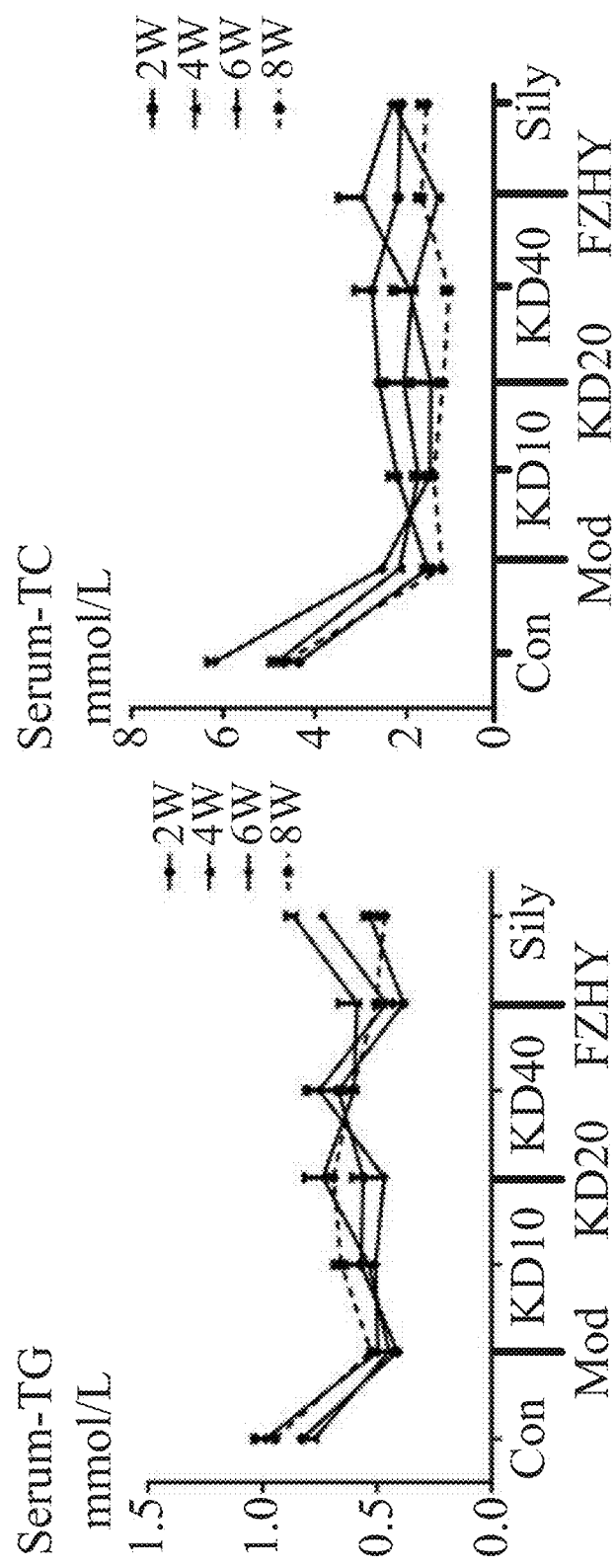
Figures 14H, 14I:
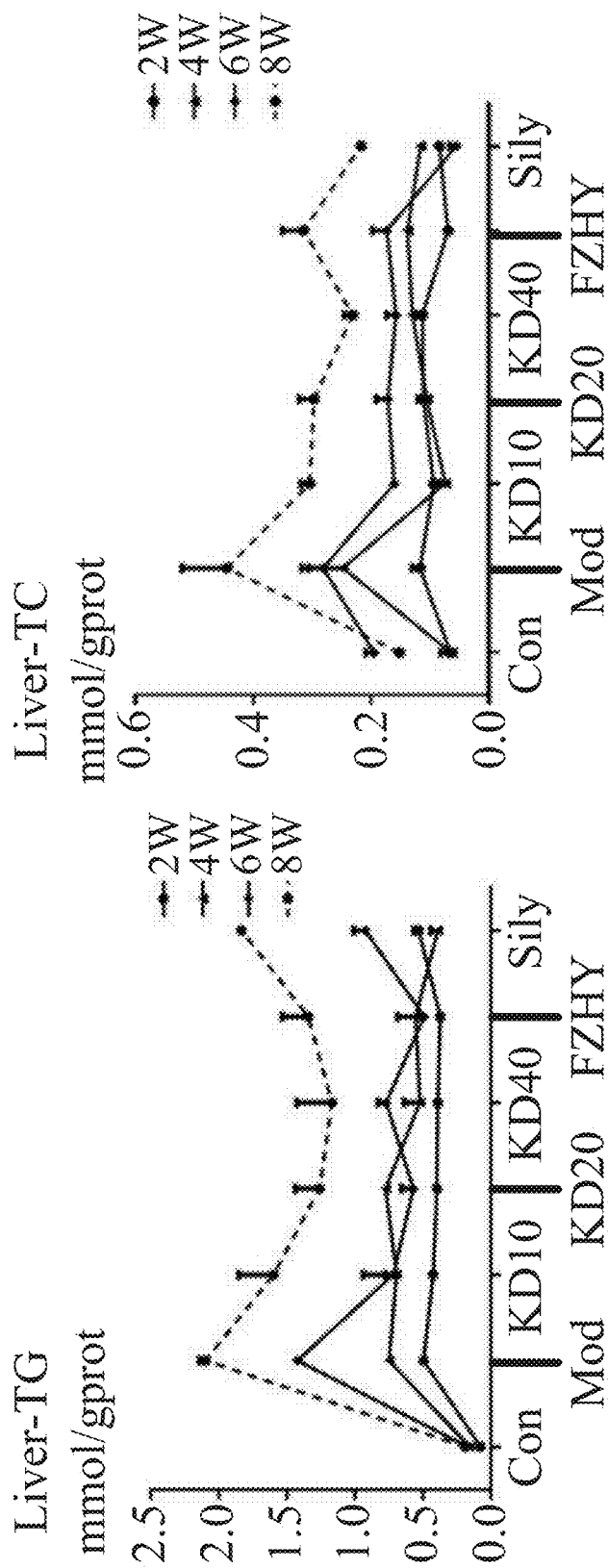
Figure 15A:
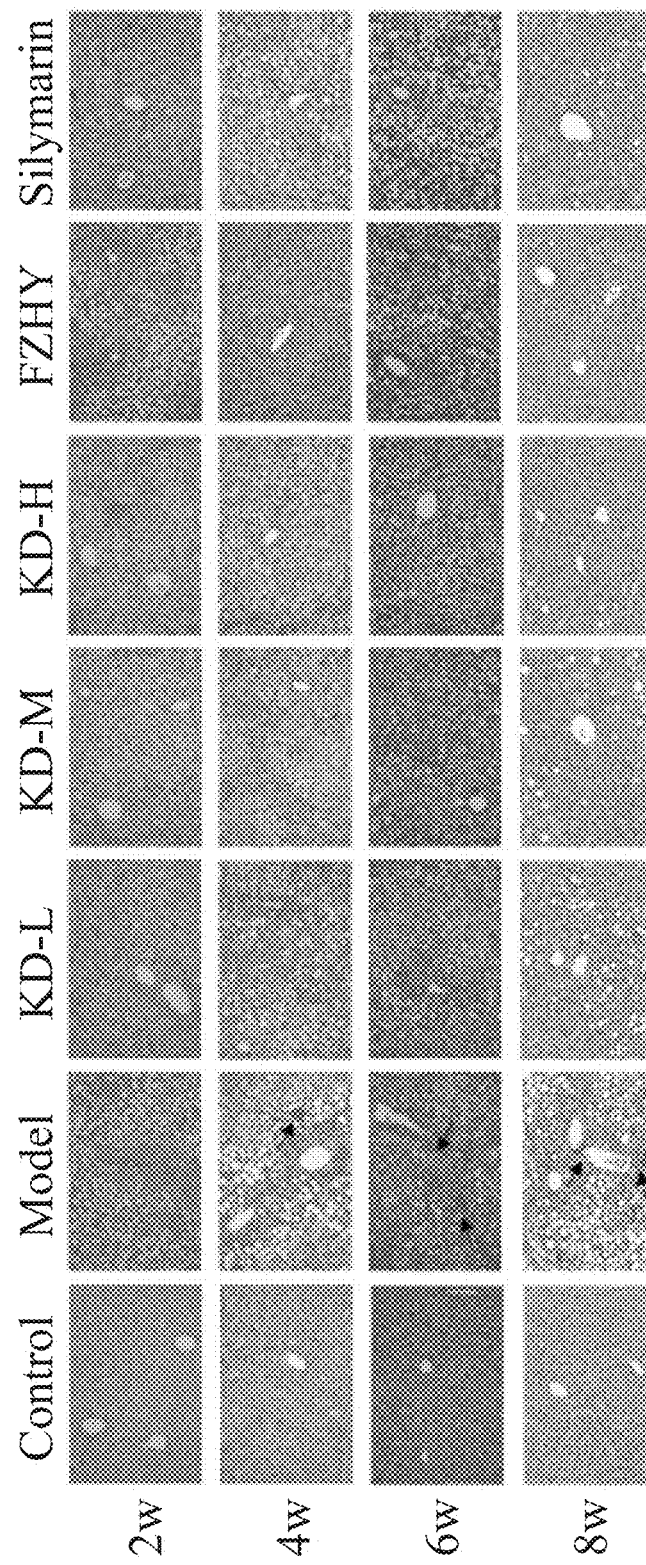
FIGS. 15A-15N: HE staining and CBA flow kit were used to detect the content of inflammatory cytokines in serum to study the effect of KD on inflammation in NASH mice. Biochemical kits (SOD and MDA) were used to determine the level of oxidative stress in each group of mice. Rt-qPCR, Western Blot and immunohistochemical staining were used to study the effect of KD on apoptosis.
Figures 15B, 15C:
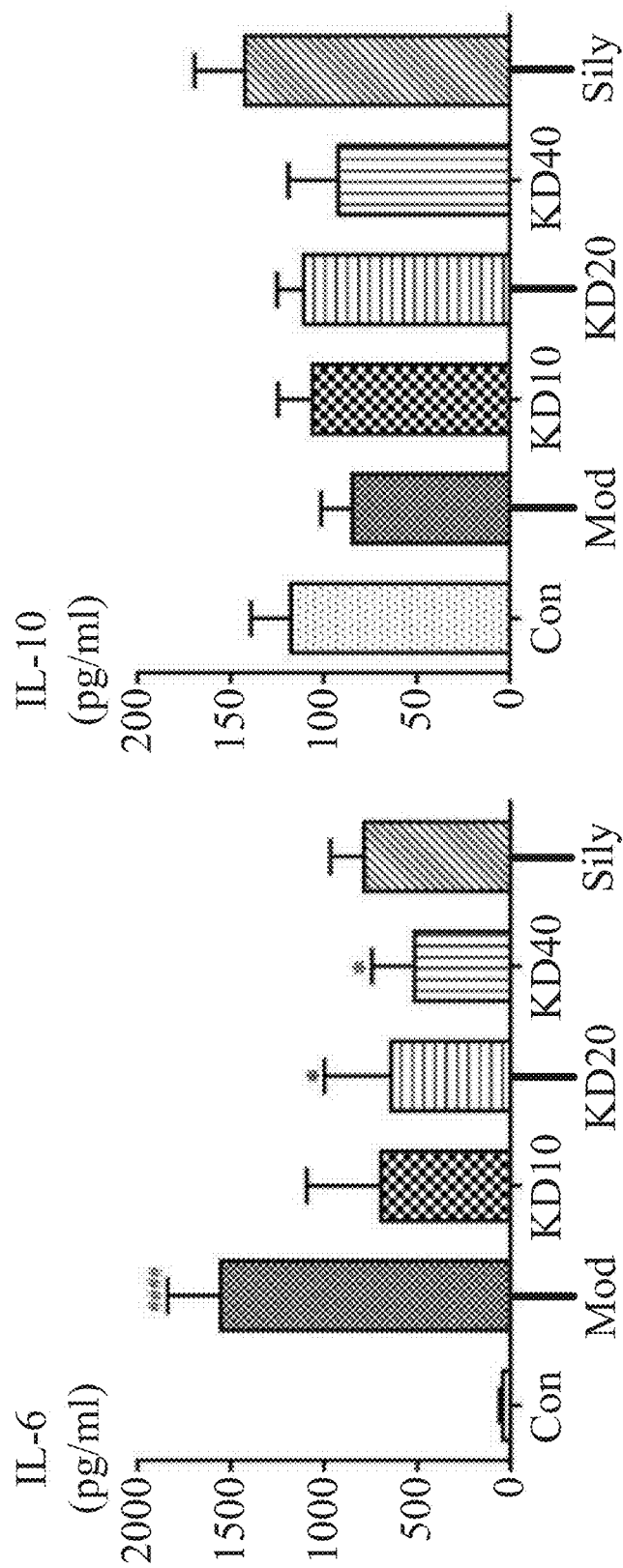
FIGS. 15B-15G: CBA flow kit was used to detect inflammatory cytokines in serum of the mice. Compared with the normal control group, the contents of pro-inflammatory cytokines IL-6, IL-12p70, MCP-1, TNF-α and IFN-γ in the model group were significantly increased, while the contents of anti-inflammatory cytokine IL-10 were decreased. The contents of pro-inflammatory cytokines and anti-inflammatory cytokine IL-10 in the serum were decreased in the KD group.
Figures 15D, 15E:
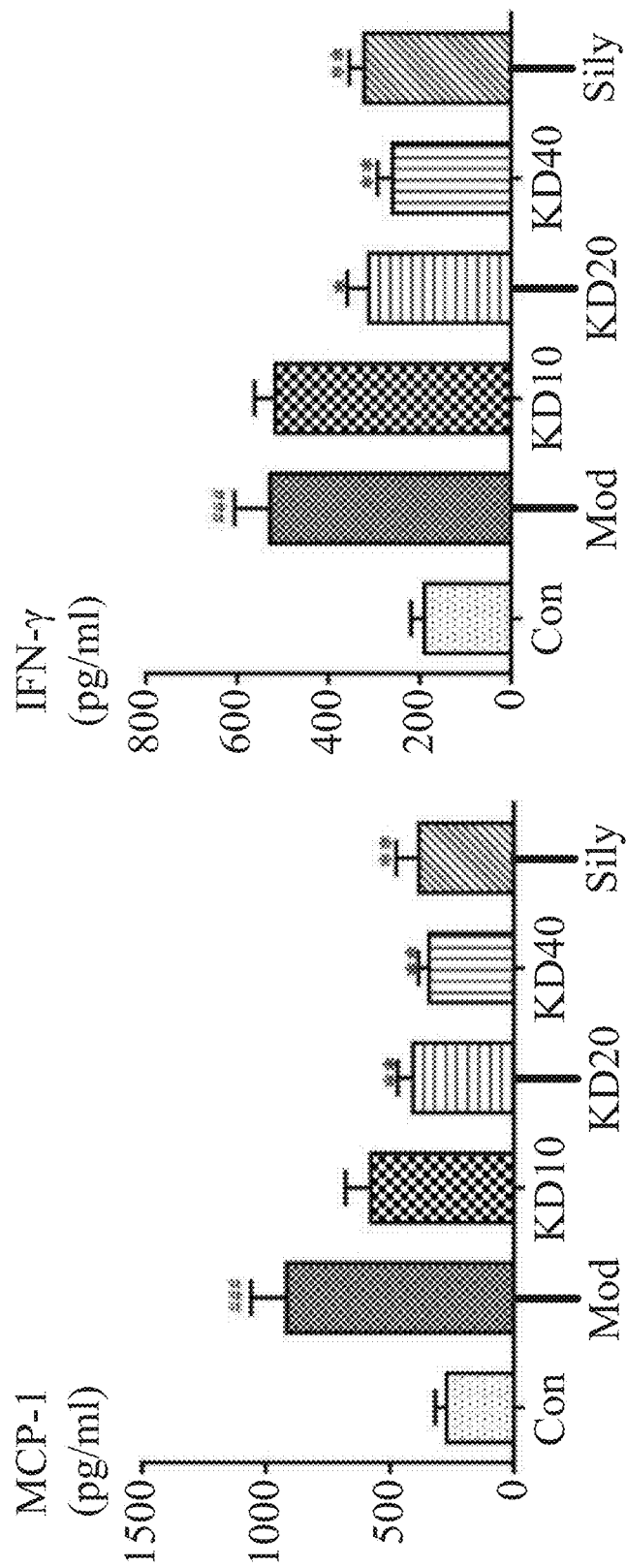
Figures 15F, 15G:
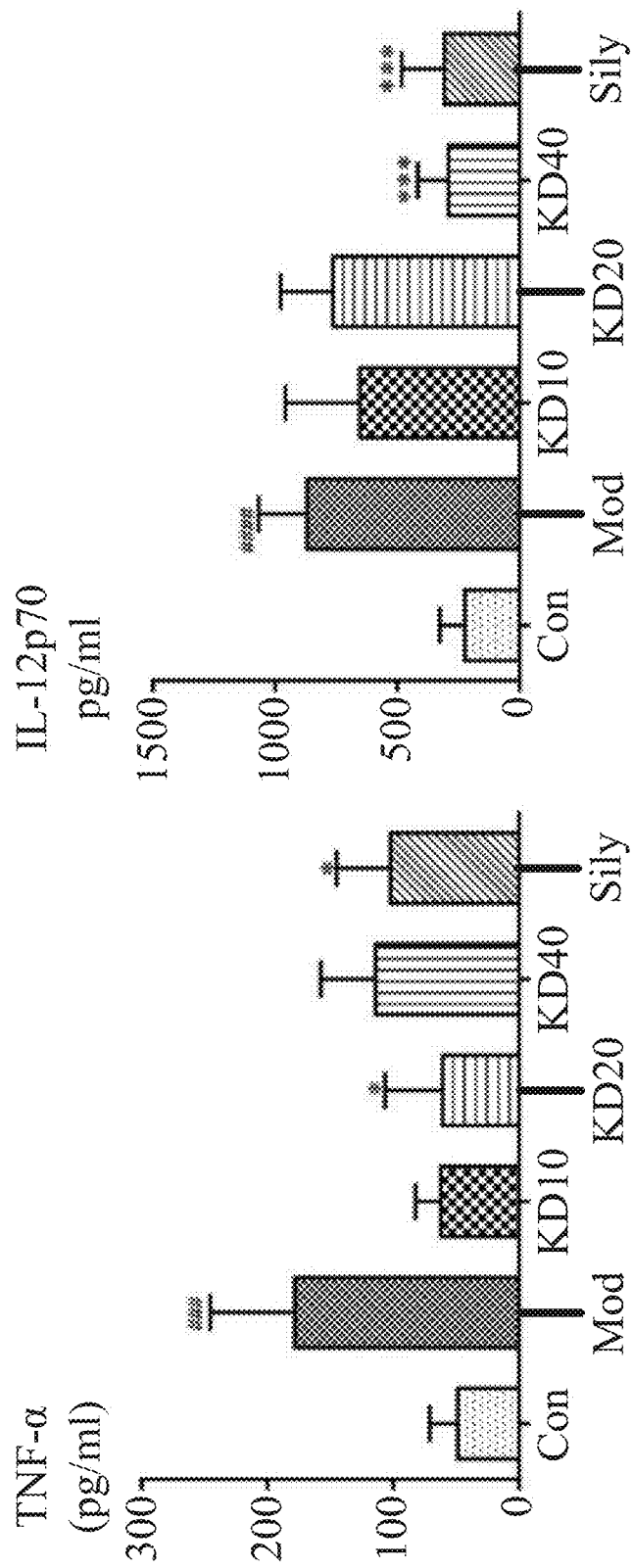
Figures 15H, 15I:
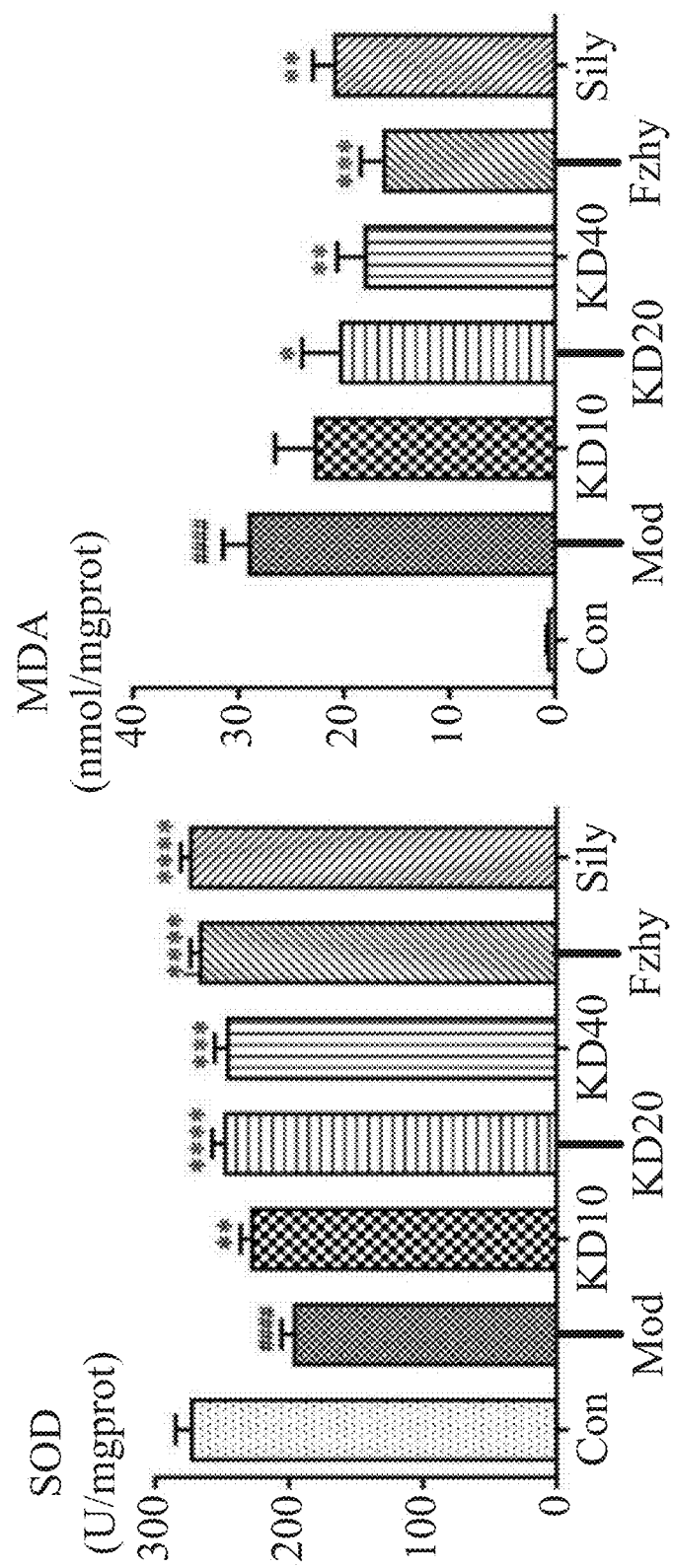
FIGS. 15H-15I: the contents of superoxide dismutase (SOD) and malondialdehyde (MDA) in liver were determined by biochemical kit. After modeling, SOD content in the liver of the model mice decreased while MDA significantly increased, suggesting that oxidative stress in the NASH mice was intensified. However, after KD treatment, SOD content in the liver increased and oxidative product MDA decreased, indicating that KD could improve oxidative stress response in NASH mice.
Figures 15J, 15K, 15L:
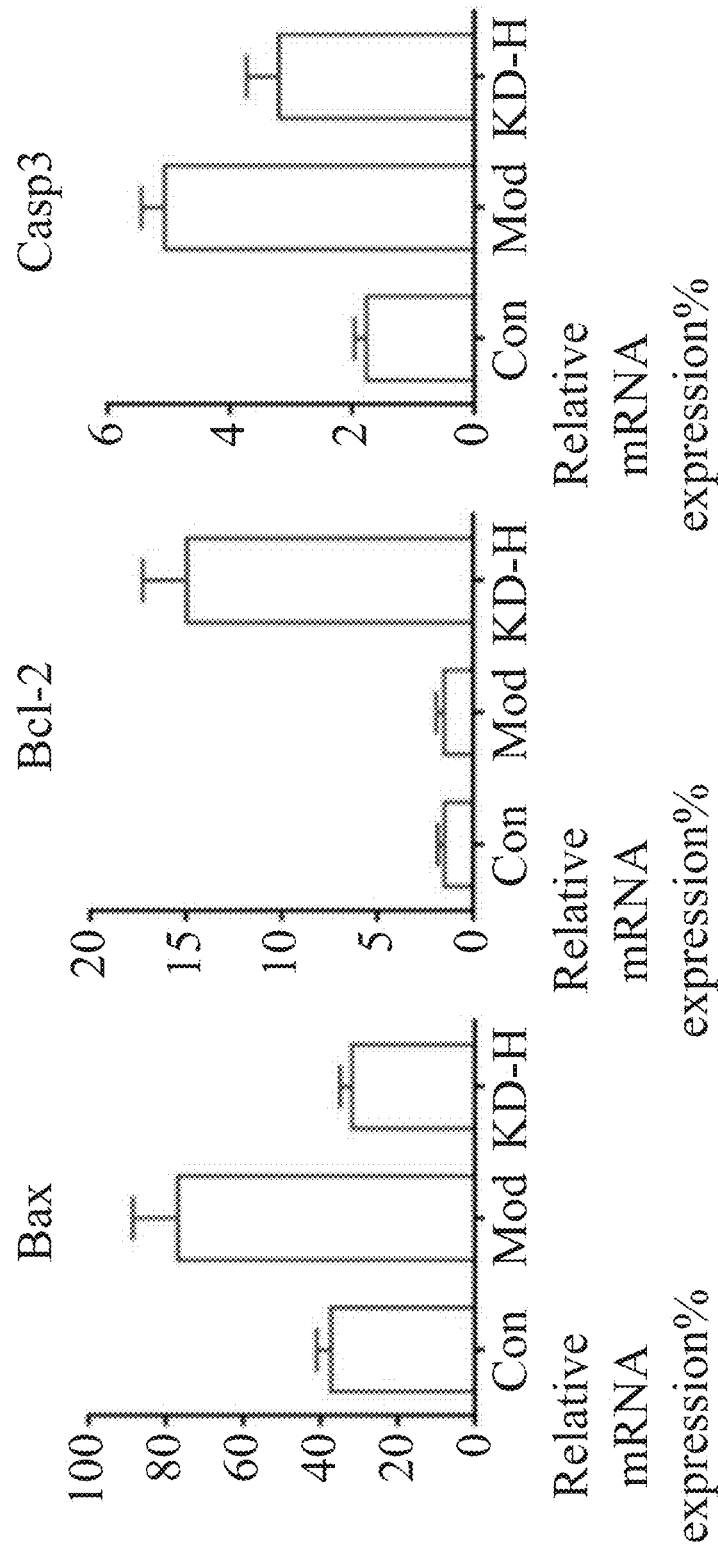
FIGS. 15J-15L: the expression of apoptosis-related genes in liver was detected by RT-qPCR. The results showed that compared with the normal group, the expression of proapoptotic gene Bax in the model group was significantly increased, the expression of anti-apoptotic gene Bcl-2 was decreased, and the expression of apoptotic marker gene Casp3 was also significantly increased. However, the KD high-dose group significantly increased the expression of anti-apoptotic gene Bcl-2, decreased the expression of pro-apoptotic gene Bax, reduced the expression of apoptotic marker gene Casp3.
Figure 15M:
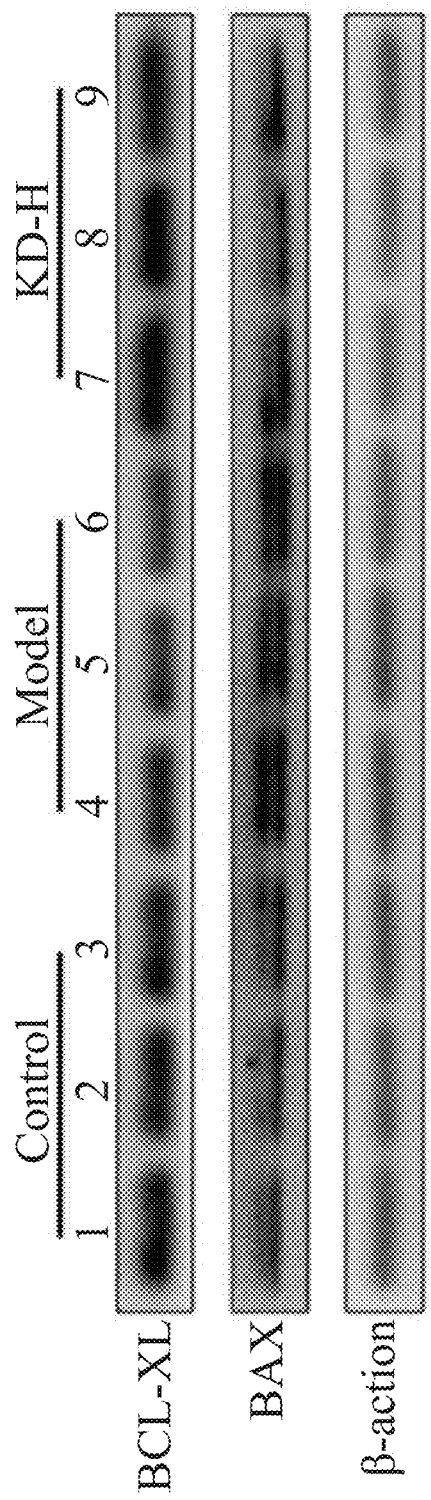
FIG. 15M: Western Blot was used to detect the expression of apoptosis-related proteins in the liver. In the model group, the content of proapoptotic protein BAX increased, while the expression of anti-apoptotic protein Bcl-xl decreased. After KD treatment, the expression of anti-apoptotic protein Bcl-xl was increased, and the proapoptotic protein BAX was inhibited, suggesting that KD had anti-apoptotic effect.
Figure 15N:
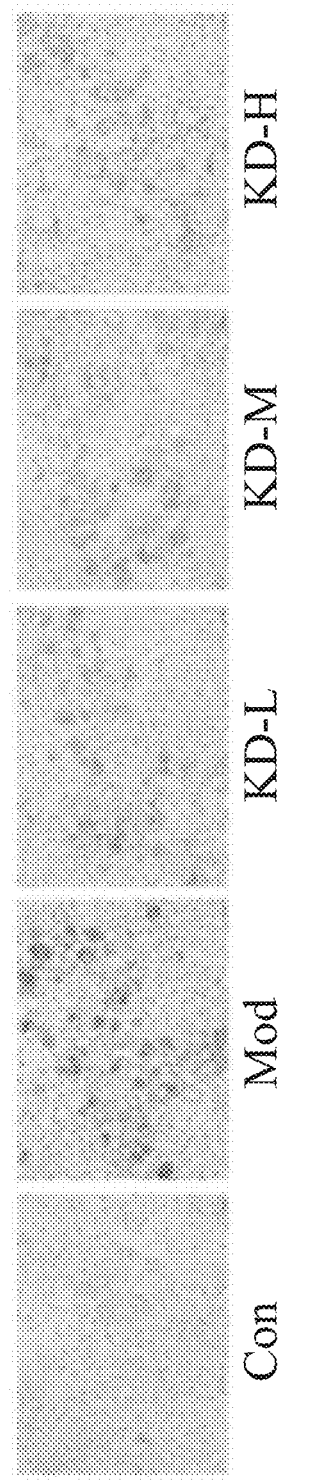
Figure 16A:
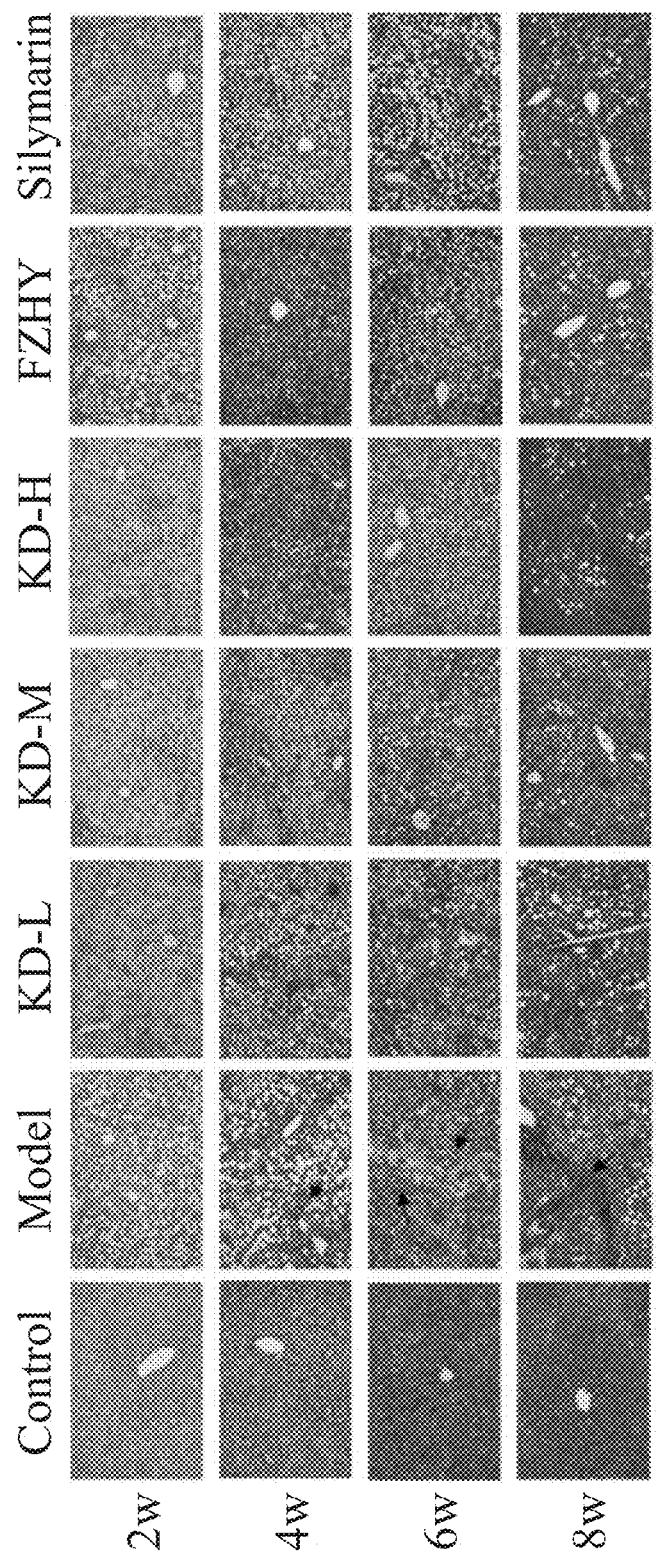
FIGS. 16A-16K show the effects of KD on liver fibrosis using Masson staining, ELISA Kit (HA, LN, C -IV, PCIII), RT-qPCR, ultrasonic instantaneous shear technique, Western blot and immunohistochemistry.
Figures 16B, 16C:
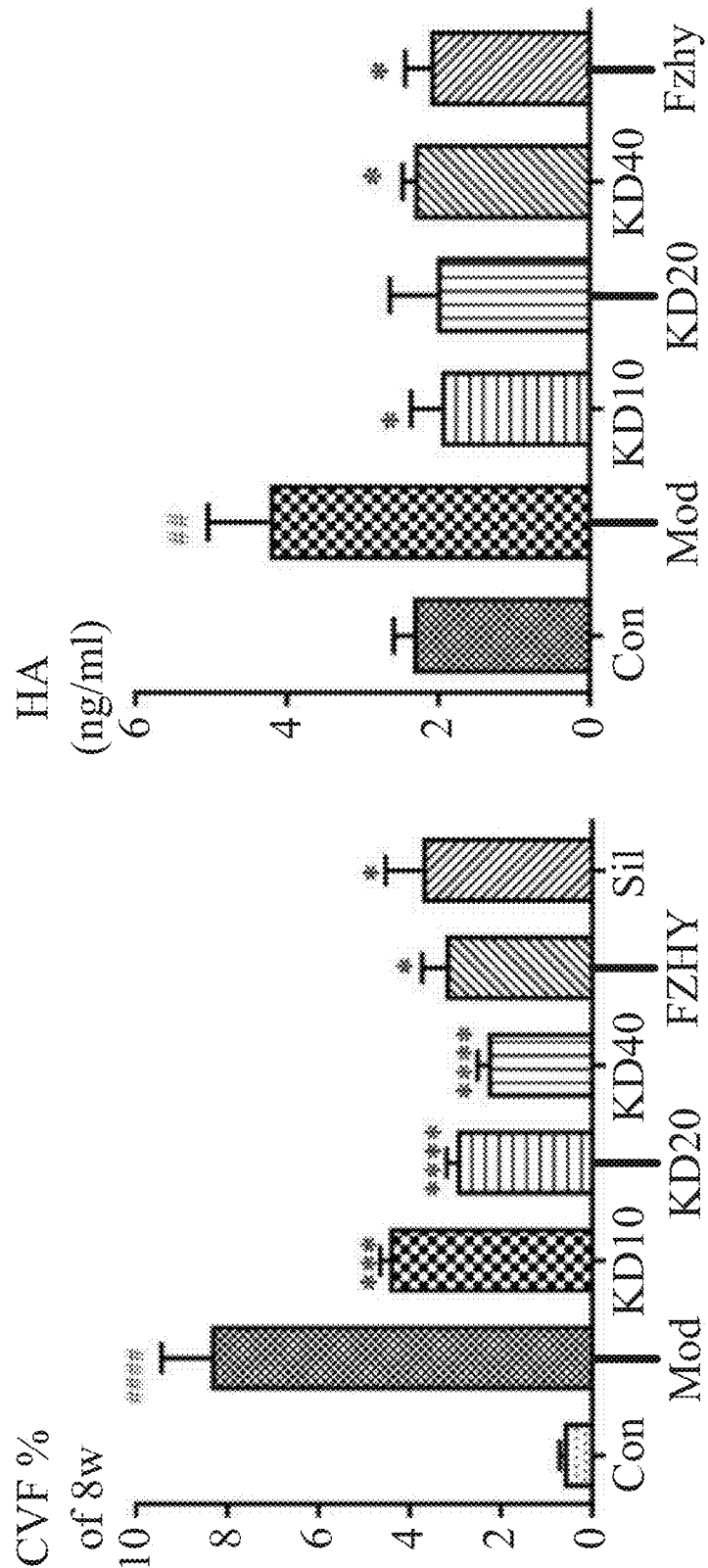
Figures 16D, 16E:
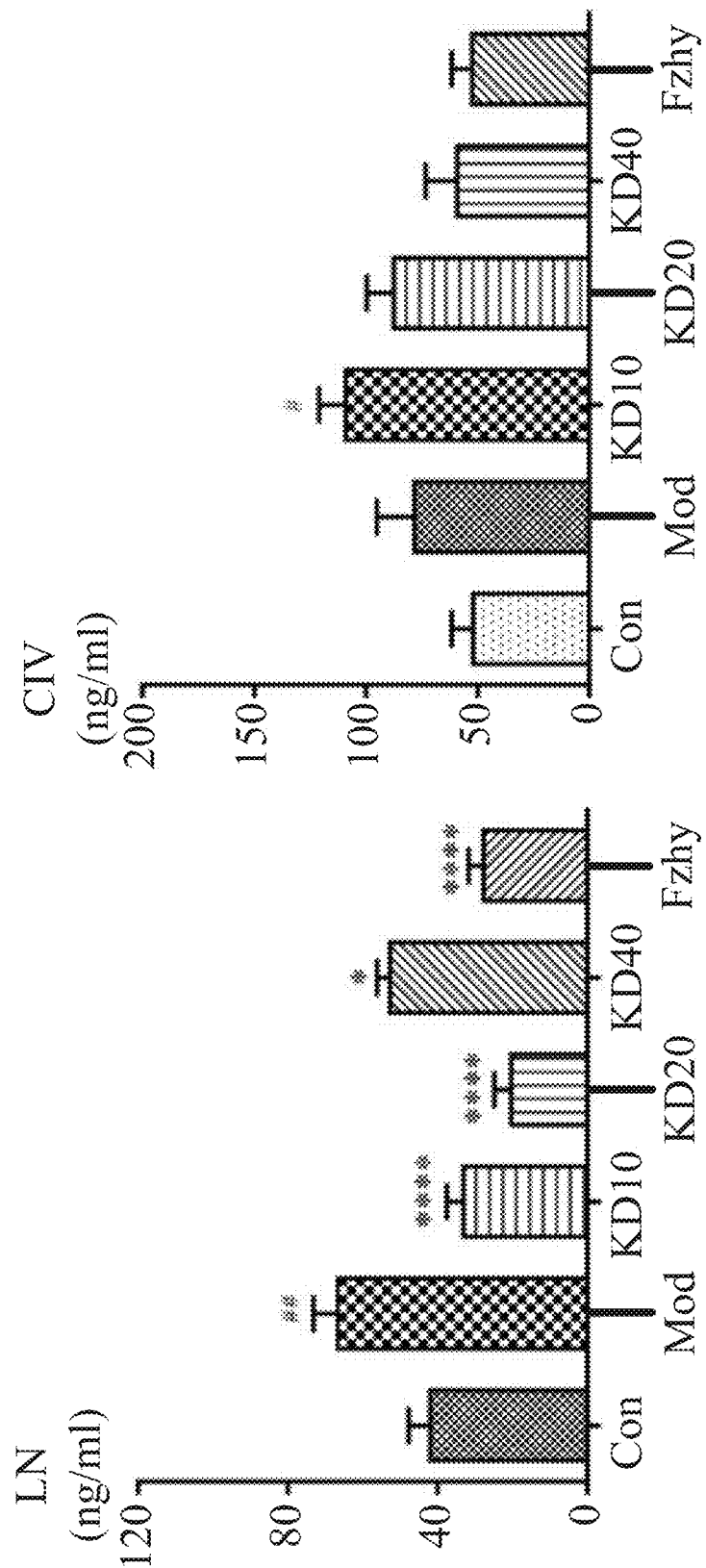
Figure 16F:
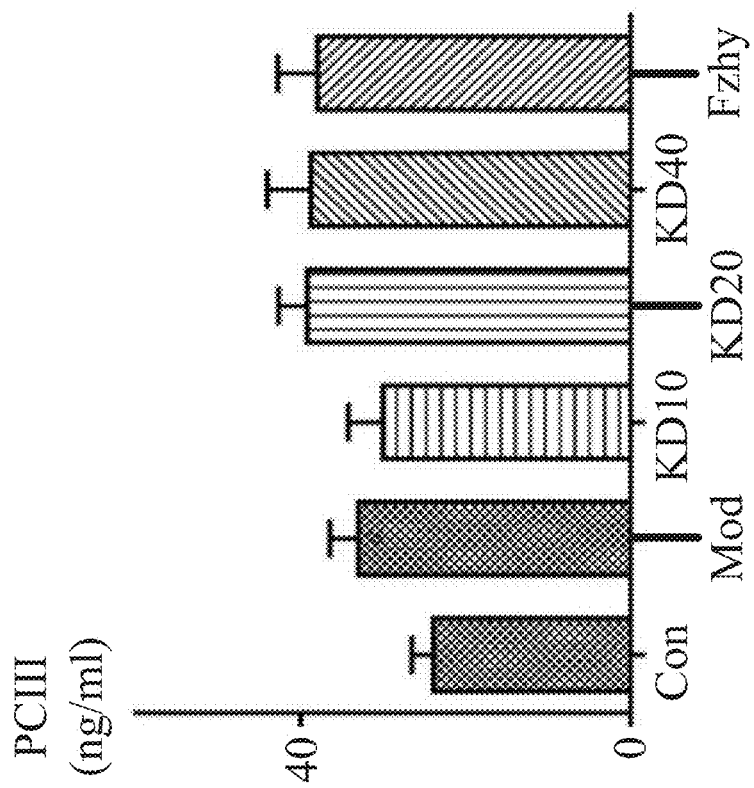
Figure 16G:
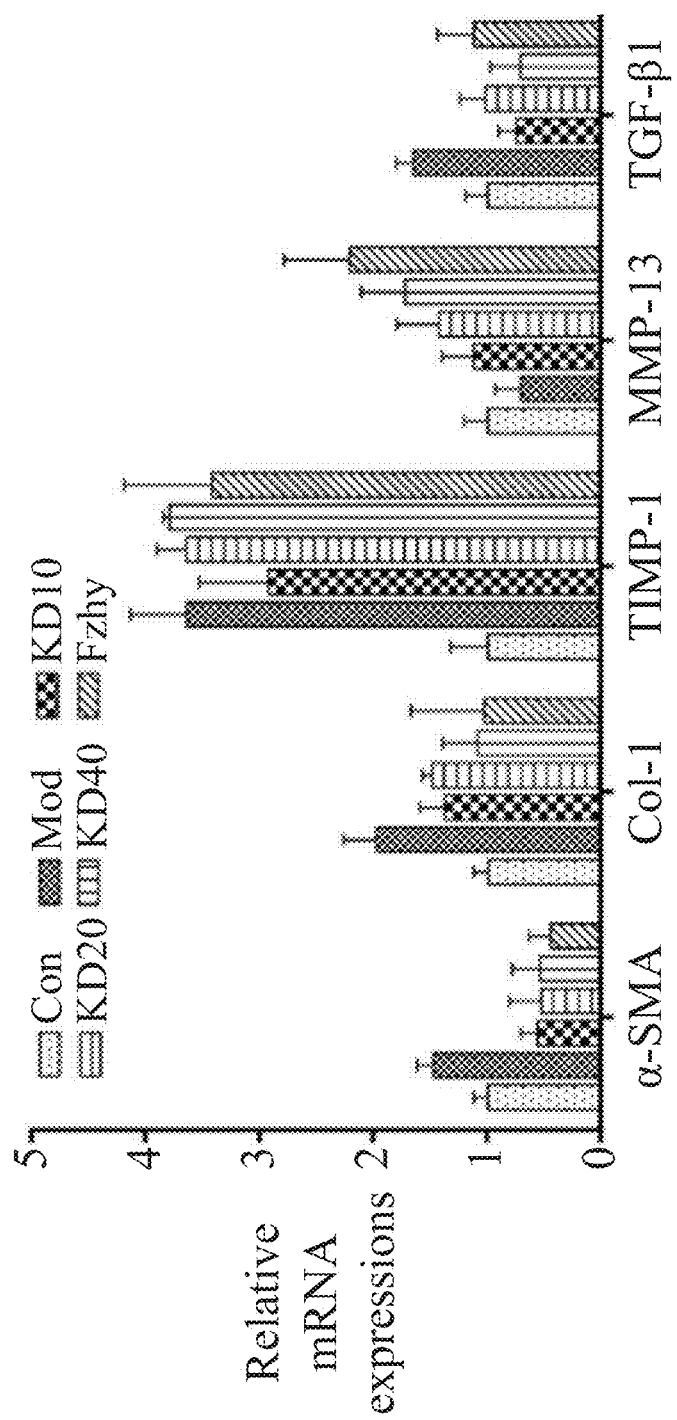
Figures 16H, 16I:
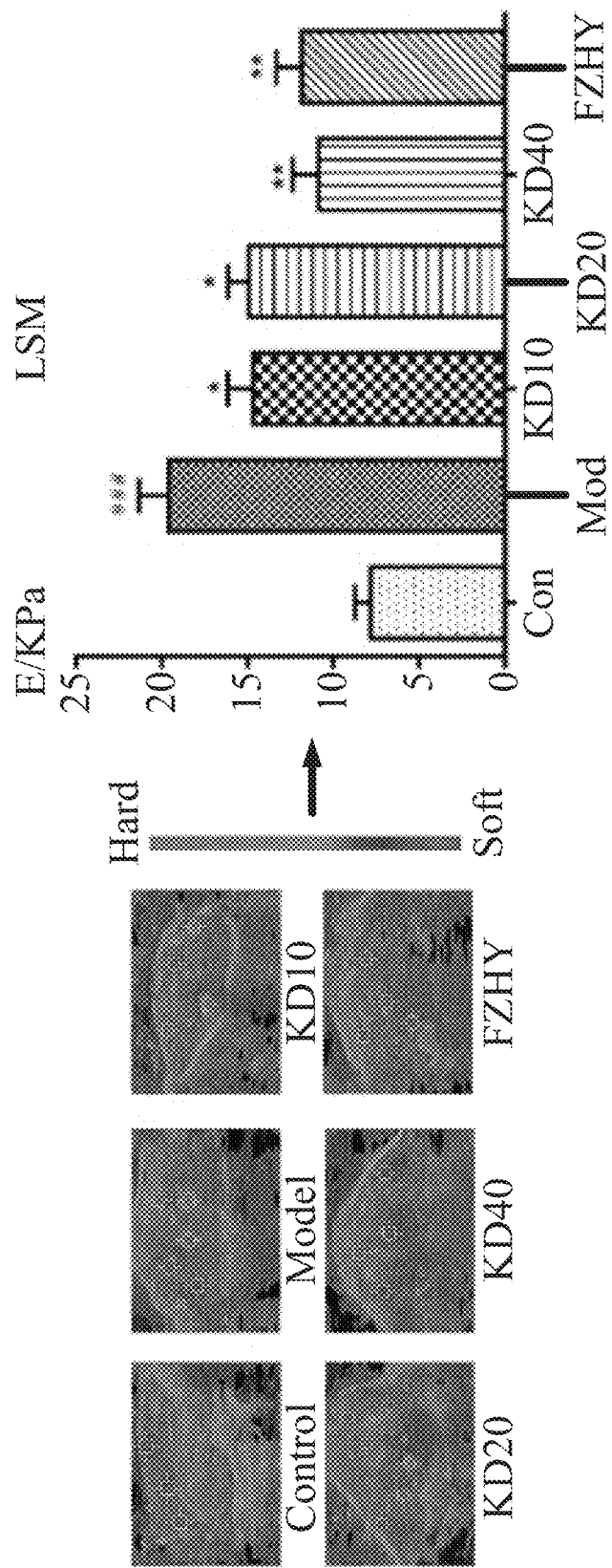

Nonalcoholic fatty liver (NAFL) was formed after 2 weeks' modeling, inflammatory lesions began to develop in the $4^{th}$ week, steatohepatitis (NASH) was formed in the $6^{th}$ week, and hepatic fibrosis gradually developed in the 8th week. (FIG. 14A). The results showed that different doses of KD could significantly reduce the ALT and AST levels in the serum, reduce liver coefficient, and improve liver function (FIGS. 11C, 11D, 11E). Liver oil red O staining showed that KD in the high dose group (40 mg/kg KD), the medium dose group (20 mg/kg KD) and the low dose group (10 mg/kg KD) significantly reduced liver fat accumulation (FIGS. 14A-14B). FIGS. 14F, 14G, 14H, and 14I showed that the fat content in the liver of the NASH mice induced by MCD was significantly decreased in each KD group, and the lipid content was slightly increased. HE staining results showed that the inflammatory lesions in the mice of the model group began in the $4^{th}$ week and progressed to NASH after 6 weeks (FIG. 15A). Compared with the normal control group, the contents of pro-inflammatory cytokines Il-6, Il-12p70, MCP-1, TNF-α and IFN-γ in the model group were significantly increased, while the content of the anti-inflammatory cytokine Il-10 was decreased. The contents of the pro-inflammatory cytokines in the serum of the KD group were decreased and the levels of the anti-inflammatory cytokine Il-10 were increased, thereby reducing the inflammatory response (FIGS. 15B, 15C, 15D, 15E, 15F and 15G). In the model group, the MDA expression increased, and the SOD activity decreased; the treatment with KD could reverse the oxidative stress injuries (FIGS. 15H-15I). In addition, KD could also reduce the expression of pro-apoptotic genes and proteins, and increase the expression of anti-apoptotic genes, thus reducing the apoptosis of liver cells (FIGS. 15J, 15K, 15L, 15M, 15N). Masson staining showed that after 8 weeks' MCD feed modeling, the mice began to develop hepatic fibrosis, and all the KD groups had inhibitory effect on the fiber formation (FIGS. 16A-16B). The development condition and the treatment potential of KD of liver fibrosis of the mice were detected by ultrasound detection of real-time shear wave elastography (SWE). The results of SWE shear wave velocity measurement showed that, the speed of the echo of the liver of the model group mice significant increased, indicating that the liver tissue was hard and the liver fibrosis was serious, while KD could significantly reduce the shear wave velocity and alleviate the liver fibrosis (FIGS. 16H, 16I).

Figure 16J:
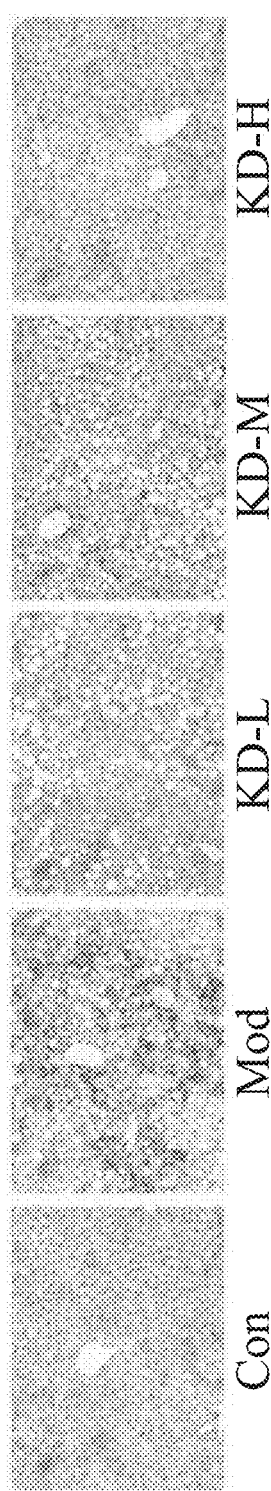
Figure 16K:
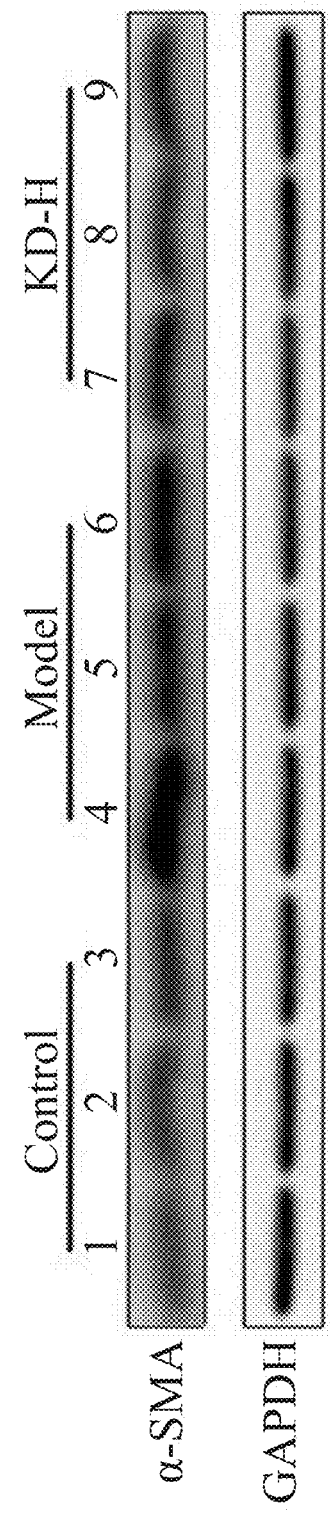
Figure 17:
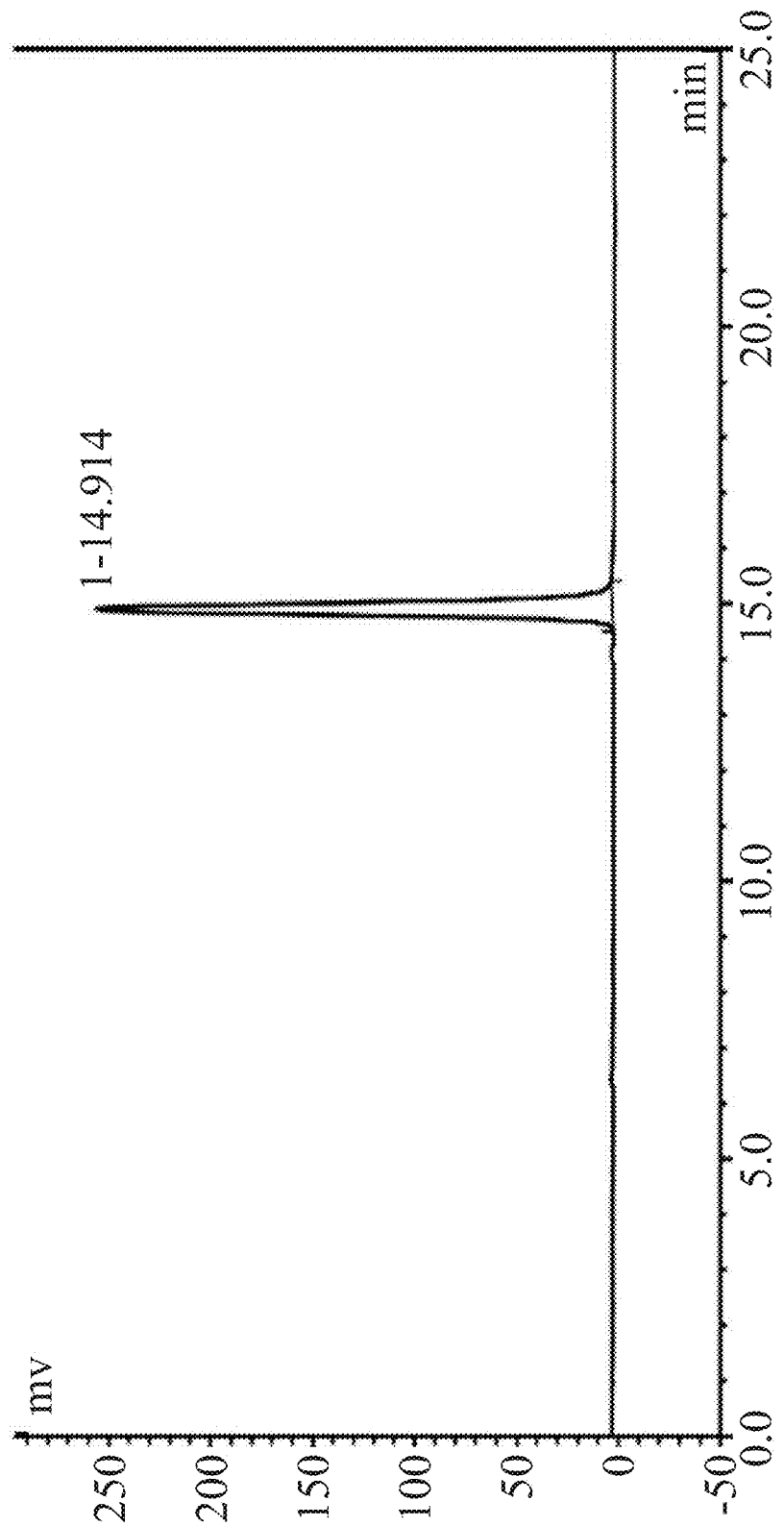
FIG. 17 shows the purity chromatogram of kinsenoside measured by HPLC.

The content of "four indexes of liver fibrosis (HA, LN, col -IV and PCIII)" in the serum of the mice was detected by ELISA kit. It was found that the four indexes of the model group were significantly higher than that of the normal control group, and each dose group of KD could reduce the content of HA and LN in varying degrees (FIGS. 16C, 16D, 16E, 16F). qPCR detected the expression of fibrosis marker genes in liver tissues, and the results also showed that, KD could effectively inhibit the expression of α-smooth muscle actin (α-SMA), collagen I (Col I), tissue inhibitor of metalloproteinase-1 (TIMP-1) and transforming growth cytokine-β (TGF-β) in the liver of the mice, and increase the expression of matrix metalloproteinase-13 (MMP-13) (FIG. 16G). Western blot assay and immunohistochemical assay showed that the expression of the fibrotic marker protein-SMA could be reduced in each KD dose group (FIGS. 16J-16K).

The therapeutic effect of KD was dose-dependent, and its effect was similar to that of the drugs silymarin and Fuzheng Huayu capsule, and was better than that of the drugs in some indexes. At the same time, the mice of the negative control group were administered with KD, and the expression of ALT, AST, and other normal functions were not affected.

Conclusion: KD has a good therapeutic effect on MCD-induced NASH, which can effectively reduce liver fat accumulation, improve liver injury, reduce inflammatory infiltration, improve liver function and oxidative stress injury, and reduce the expression of fibrosis marker genes to prevent the progression of NASH to liver fibrosis.

In summary, the compound can effectively prevent the development of a variety of liver diseases, reduce liver damage in the body, improve liver function and oxidative stress damage, reduce liver fat accumulation, decrease the secretion of inflammatory cytokine, decrease the expression of proapoptotic cytokine and fibrosis marker gene, and can be used as a drug for the treatment of liver diseases.

It will be obvious to those skilled in the art that changes and modifications may be made, and therefore, the aim in the appended claims is to cover all such changes and modifications.

What is claimed is:

1. A method for treatment of a liver disease, the method comprising administering kinsenoside to a patient in need thereof, wherein the liver disease is nonalcoholic fatty liver disease induced by methionine choline deficiency (MCD) diet.

2. The method of claim 1, wherein a daily usage amount of the kinsenoside is 60 mg/d-3 g/d.

3. A method for treatment of a liver disease, the method comprising administering kinsenoside to a patient in need thereof, wherein the liver disease is cholestatic liver injury.

4. The method of claim 3, wherein a daily usage amount of the kinsenoside is 60 mg/d-3 g/d.

* * * * *